(12) United States Patent
Lu et al.

(10) Patent No.: US 7,446,210 B2
(45) Date of Patent: Nov. 4, 2008

(54) FACTOR XA COMPOUNDS

(75) Inventors: Tianbao Lu, Churchville, PA (US); Tho V. Thieu, Ambler, PA (US); Yu-Kai Lee, Exton, PA (US); Daniel J. Parks, Downingtown, PA (US); Thomas P. Markotan, Morgantown, PA (US); Wenxi Pan, Glenmore, PA (US); Karen L. Milkiewicz, Exton, PA (US); Mark R. Player, Phoenixville, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/257,208

(22) Filed: Oct. 24, 2005

(65) Prior Publication Data

US 2006/0199809 A1 Sep. 7, 2006

Related U.S. Application Data

(60) Provisional application No. 60/622,156, filed on Oct. 26, 2004.

(51) Int. Cl.
| | |
|---|---|
| C07D 207/00 | (2006.01) |
| C07D 213/00 | (2006.01) |
| C07D 231/00 | (2006.01) |
| C07D 231/54 | (2006.01) |
| C07D 239/02 | (2006.01) |
| C07D 241/04 | (2006.01) |
| C07D 265/28 | (2006.01) |
| C07D 295/00 | (2006.01) |
| C07D 487/00 | (2006.01) |

(52) U.S. Cl. ...................... 548/358.1; 544/98; 544/298; 544/383; 546/1; 548/356.1; 548/400

(58) Field of Classification Search ........................ None
See application file for complete search history.

(56) References Cited

U.S. PATENT DOCUMENTS

| 5,444,038 A | * | 8/1995 | James et al. ................ 504/253 |
| 7,067,507 B2 | * | 6/2006 | Pulley et al. ................ 514/183 |
| 2003/0114448 A1 | | 6/2003 | Zhang et al. |

FOREIGN PATENT DOCUMENTS

| WO | WO 95/29189 A1 | 11/1995 |
| WO | WO 99/33800 A1 | 7/1999 |
| WO | WO 00/01389 A1 | 1/2000 |
| WO | WO 02/051831 A1 | 4/2002 |
| WO | WO 02/48159 A1 | 6/2002 |
| WO | WO 03/044014 A1 | 5/2003 |
| WO | WO 2004/002405 A2 | 1/2004 |
| WO | WO 2004/002477 A1 | 1/2004 |
| WO | WO 2004/050636 A1 | 6/2004 |
| WO | WO 2004/056815 A1 | 7/2004 |
| WO | WO 2004/058743 A1 | 7/2004 |

OTHER PUBLICATIONS

McQueen, M. Clinica Chimica Acta, 2002, 315 (1-2), 5-15.*
Chi et al. Expert Opinion on Investigational Drugs, 1997, 6(11), 1591-1605).*
PCT International Search Report, PCT/US05/38182, May 23, 2006.
H. Theo Cuypers, et al., *Sulfhydryl Content of Bovine Eye Lens Leucine Aminopeptidase: Determination of The Reactivity of The Sulfhydryl Groups of The Zinc Metalloenzyme, of The Enzyme Activated by $Mg^{2+}$, $Mn^{2+}$, and $Co^{2+}$, and of The Metal-Free Apoenzyme*, Journal of Biological Chemistry, vol. 257, No. 12, 1982, pp. 7086-7091.
Alan J. Barrett, *Proteinase Inhibitors: Potential Drugs,?* Biochemistry Department, Strangeways Laboratory, Cambridge CB1, 4RN, UK), pp. 219-229, 1980.
Carlo Tapparelli, et al., *Synthetic Low-molecular Weight Thrombin Inhibitors: Molecular Design and Pharmacological Profile*, TiPS, Oct. 1992, vol. 14, pp. 366-376.
J. Lefkovits, et al., *Direct Thrombin Inhibitors in Cardiovascular Medicine*, Journal AHA, 1994; 90; pp. 1522-1536.
L. A. Harker, *Strategies for Inhibiting The Effects of Thrombin, Blood Coagulation and Fibrinolysis*, vol. 5, Suppl 1, 1994, pp. S47-S58.
Shaun R. Coughlin, *Molecular Mechanisms of Thrombin Signaling*, Seminars in Hematology, vol. 31, No. 4, 1994, pp. 270-277.
Goran Claeson, *Synthetic Peptides and Peptidomimetics as Substrates and Inhibitors of Thrombin and Other Proteases in The Blood Coagulation System*, Blood Coagulation and Fibrinolysis, vol. 5, 1994, pp. 411-436.
Susan Elodi, et al., *Optimization of Conditions for The Catalytic Effect of The Factor Ixa—Factor VIII Complex: Probable Role of The Complex in The Amplification of Blood Coagulation*, Thrombosis Research 15; Pergamon Press Ltd. 1979, pp. 617-629.

* cited by examiner

*Primary Examiner*—James O. Wilson
*Assistant Examiner*—Noble Jarrell
(74) *Attorney, Agent, or Firm*—Laura Donnelly

(57) ABSTRACT

The present invention is directed to novel compounds of Formula I:

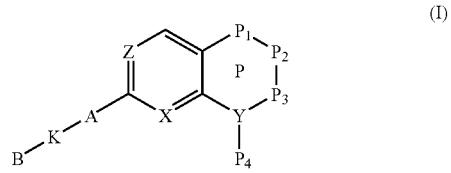

and forms and pharmaceutical compositions thereof, and the use thereof as inhibitors of Factor Xa.

13 Claims, No Drawings

FACTOR XA COMPOUNDS

CROSS REFERENCE TO RELATED APPLICATIONS

This present application claims benefit of U.S. Provisional Patent Application Ser. No. 60/622,156 filed Oct. 26, 2004, which is incorporated herein by reference in its entirety and for all purposes.

FIELD OF THE INVENTION

The present invention relates to novel compounds that function as enzyme inhibitors, and particularly to a new class of potent and selective inhibitors of Factor Xa. The present invention also relates to the novel compounds, their pharmaceutically acceptable salts, and pharmaceutically acceptable compositions thereof which are useful as potent and selective inhibitors of blood coagulation in mammals and methods for using these inhibitors as therapeutic agents for disease states in mammals characterized by coagulation disorders.

BACKGROUND OF THE INVENTION

Proteases are enzymes that cleave proteins at single, specific peptide bonds. Proteases can be classified into four generic classes: serine, thiol or cysteinyl, acid or aspartyl, and metalloproteases. (Cuypers et al., J. Biol. Chem. 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in Enzyme Inhibitors as Drugs, Sandler, ed., University Park Press, Baltimore, (1980)). Additional proteases such as plasmin, C-1 esterase, C-3 convertase, urokinase, plasminogen activator, acrosin, and kallikreins play key roles in the normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, Factor Xa and kallikreins.

The serine protease thrombin occupies a central role in hemostasis and thrombosis, and as a multifactorial protein, induces a number of effects on platelets, endothelial cells, smooth muscle cells, leukocytes, the heart, and neurons. (Tapparelli et al., Trends in Pharmacological Sciences 14:366-376 (1993); Lefkovits and Topol, Circulation 90(3): 1522-1536 (1994); Harker, Blood Coagulation and Fibrinolysis 5 (Suppl 1):S47-S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, Seminars in Hematology 31(4):270-277 (1994)), and autoamplifies its own production through a feedback mechanism. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, blood lines and stents.

Factor Xa is another serine protease in the coagulation pathway. Factor Xa associates with Factor Va and calcium on a phospholipid membrane thereby forming a prothrombinase complex. This prothrombinase complex then converts prothrombin to thrombin. (Claeson, Blood Coagulation and Fibrinolysis 5:411-436 (1994); Harker, Blood Coagulation and Fibrinolysis 5 (Suppl 1):S47-S58 (1994)). Inhibitors of Factor Xa are thought to offer an advantage over agents that directly inhibit thrombin since direct thrombin inhibitors still permit significant new thrombin generation (Lefkovits and Topol, Circulation 90(3):1522-1536 (1994); Harker, Blood Coagulation and Fibrinolysis 5 (Suppl 1):S47-S58 (1994)) because one molecule of Factor Xa may be able to generate up to 138 molecules of thrombin (Elodi et al., Thromb. Res. 15 (617-619 (1979)).

Several specific inhibitors of Factor Xa have been reported. Both synthetic and protein inhibitors of Factor Xa have been identified, and these include, for example, antistasin ("ATS") and tick anticoagulant peptide ("TAP"). ATS, which is isolated from the leech, *Haementerin officinalis*, contains 119 amino acids and has a Ki for Factor Xa of 0.05 nM. TAP, which is isolated from the tick, *Ornithodoros moubata*, contains 60 amino acids and has a Ki for Factor Xa of about 0.5 nM.

ATS and TAP have not been developed clinically. One major disadvantage of these two inhibitors is that administration of the required repeated doses causes the generation of neutralizing antibodies, thus limiting their potential clinical use. Moreover, the sizes of TAP and ATS render oral administration impossible, further restricting the number of patients able to benefit from these agents.

A specific inhibitor of Factor Xa would have substantial practical value in the practice of medicine. In particular, a Factor Xa inhibitor would be effective under circumstances where the present drugs of choice, heparin and related sulfated polysaccharides, are ineffective or only marginally effective. Thus, there exists a need for a low molecular weight, Factor Xa-specific blood clotting inhibitor that is effective, but does not cause unwanted side effects.

Low molecular weight, Factor Xa-specific blood clotting inhibitors, have been described in International Application WO 9529189. Indole derivatives as low molecular weight, Factor Xa-specific blood clotting inhibitors have been proposed in International Application 99338000.

WO 2004058743 discloses substituted nitrogen-containing heterobicycles and uses thereof as Faxtor Xa inhibitors.

WO 2004050636 discloses imidazole derivatives as Factor Xa inhibitors.

WO 2004056815 discloses pyrazole derivatives as Factor Xa inhibitors.

WO 2003044014 discloses indole-2 carboxamides as Faxtor Xa inhibitors.

WO 2002051831 discloses oxybenzamide derivatives as Factor Xa inhibitors.

WO 2002046159 discloses guanidine and amidine derivatives as Factor Xa inhibitors.

WO 2004002477 discloses 2-(phenyl)-2H-pyrazole-3-carboxylic-acid-N-4-(thioxo-heterocyclyl)-phenyl-amide derivatives and corresponding imino-heterocyclyl derivatives as Factor Xa inhibitors.

WO 2004002405 discloses amino-bicyclic pyrazinones and pyridinones as Factor Xa inhibitors.

However, it is desirable that such inhibitors have advantageous pharmacological properties, for instance high stability in plasma and liver and high selectively versus other serine proteases. A need continues to exist for non-peptidic compounds that are potent and selective protease inhibitors, and which possess greater bioavailability and fewer side effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states. In particular there continues to be a need for compounds that selectively inhibit Factor Xa.

BRIEF DESCRIPTION OF THE INVENTION

In accordance with the present invention, novel derivatives are provided which are inhibitors of the enzyme Factor Xa.

In addition, in accordance with the present invention, a method for preventing, inhibiting or treating cardiovascular diseases associated with thromboses is provided, wherein a novel derivative of the invention is administered in a therapeutically effective amount to inhibit Factor Xa.

SUMMARY OF THE INVENTION

A first aspect of the present invention is directed to novel compounds of Formula I.

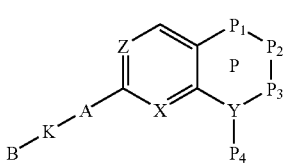

(I)

X is selected from CH, COH, COCH$_3$, N, CF or NO;
Z is selected from CH or N;
A and B are independently selected from ethenyl, ethynyl, aryl, heteroaryl, 3-8 numbered carbocycle or 5-8 numbered heterocycle, each of which can be optionally substituted with 1, 2, 3 or 4 R groups;
K is selected from a bond, ethenyl, ethynyl, NR', O, S, SO$_2$ or CO;
one of Y, P$_1$, P$_2$ or P$_3$ is a bond;
Ring P is selected from:

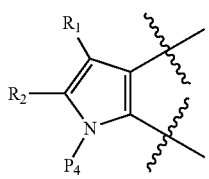 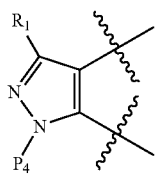

-continued

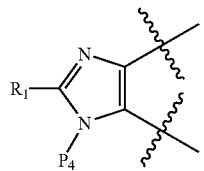 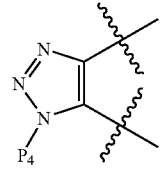

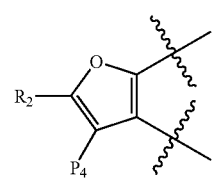 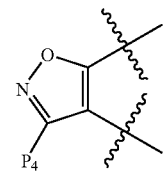

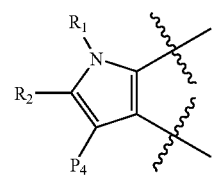 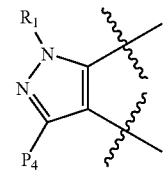

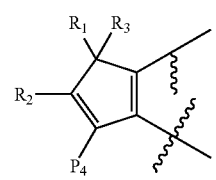 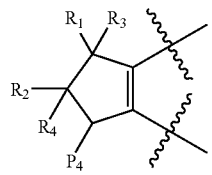

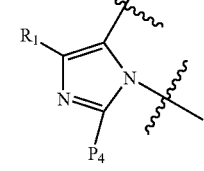 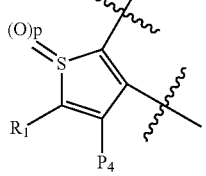

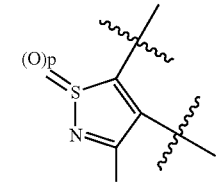 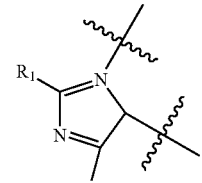

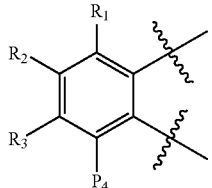 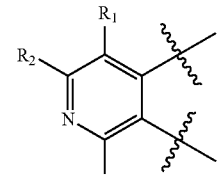

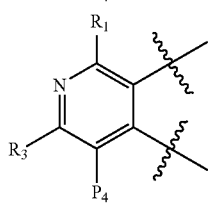 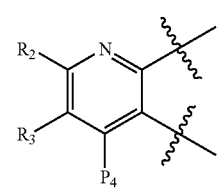

-continued
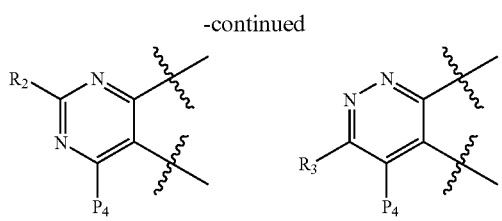
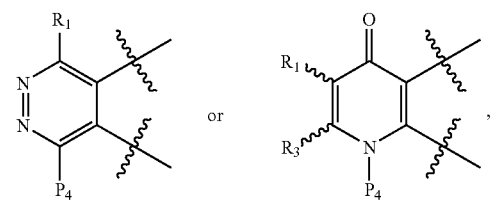 or
wherein p is independently selected from 0, 1 or 2;
P$_4$ is selected from:
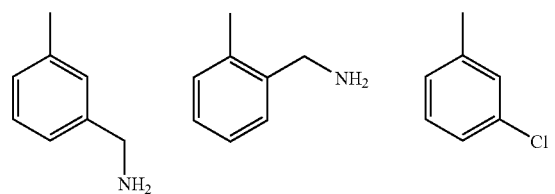
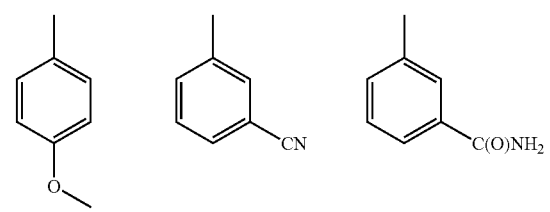
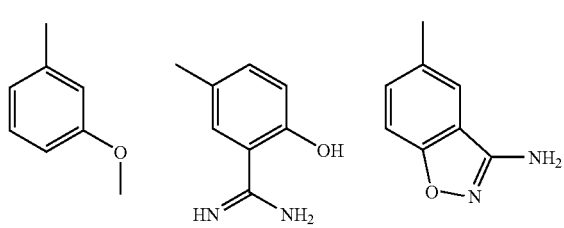
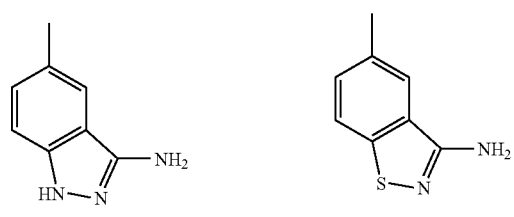
-continued
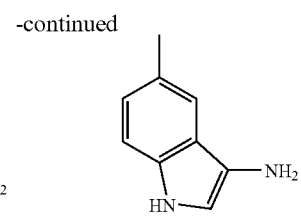
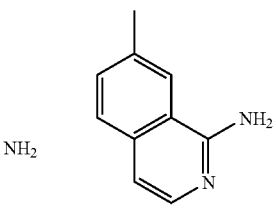
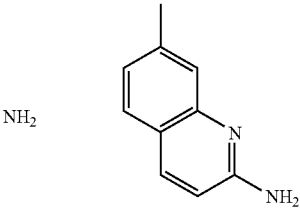
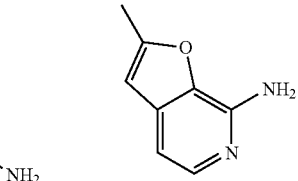
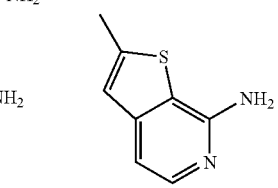
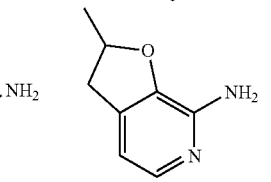
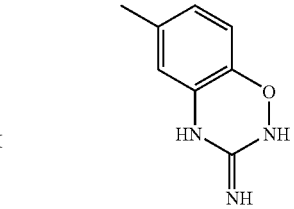
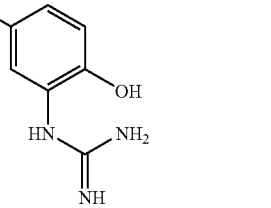

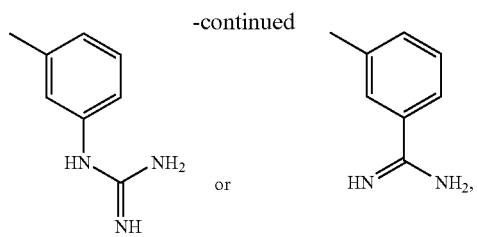

wherein $P_4$ is optionally substituted with 1, 2, 3 or 4 R groups;

$R_1$, $R_2$, and $R_3$ are independently selected from hydrogen, halogen, alkyl, haloalkyl, haloalkoxy, alkenyl, alkynyl, cycloalkyl, $NCH_2R$, $OCH_2R$, $SCH_2R$, $S(O)_pCH_2R$, $C(O)NR$, $OC(O)NR$, $NR^aC(O)NR^aCH_2R$, $NR^aC(O)OCH_2R$, $NR^aC(O)CH_2R$, hydroxyalkyl, cyano, nitro, trifluoromethyl or $-CO_2R$;

provided that $R_1$ forms other than an N-halo, N—N, N—S, N—O, or N—CN bond;

R is selected from hydrogen, halogen, alkyl, alkenyl, alkynyl, cycloalkyl, hydroxy, alkoxy, haloalkyl, haloalkoxy, hydroxyalkyl, cyano, nitro, trifluoromethyl, $-CO_2R^x$, $-CH_2OR^x$ or $-OR^x$, $R^x$ is selected from hydrogen, $C_{1-6}$ alkyl; optionally substituted alkyl, optionally substituted cycloalkyl, optionally substituted aryl or optionally substituted heteroaryl,
  wherein optionally substituted alkyl, cycloalkyl, aryl and heteroaryl are each optionally substituted with one, two, three or four substituents selected from halogen, hydroxy, amino, mono or dialkyl amino, cyano, nitro, ester, acid or ether;

R' is selected from hydrogen, optionally substituted alkyl, optionally substituted alkenyl, optionally substituted alkynyl, optionally substituted cycloalkyl, optionally substituted $C_{6-10}$aryl, optionally substituted $C_{6-10}$ arylalkyl, optionally substituted heteroaryl or optionally substituted heteroaryl-alkyl,
  wherein optionally substituted alkyl, alkenyl, alkynyl, cycloalkyl, $C_{6-10}$aryl, the $C_{6-10}$aryl portion of $C_{6-10}$ arylalkyl, heteroaryl and the heteroaryl portion of heteroaryl-alkyl are each optionally substituted with one, two, three or four substituents selected from halogen, hydroxy, carboxy, amino, monoalkylamino, dialkylamino, cyano, nitro, ester, acid or ether; and $R^a$ is selected from hydrogen, $C_{1-4}$alkyl or $C_{6-10}$aryl.

An example of the present invention includes compounds of Formula (I) wherein, Ring P is:

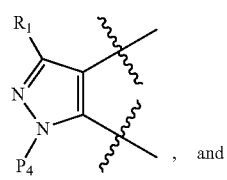

$R_1$ is selected from alkyl, haloalkyl, C(O)NR or hydroxyalkyl.

Another example of the present invention includes compounds of Formula (I) wherein, Ring P is:

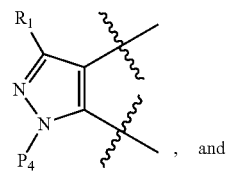

$P_4$ is selected from:

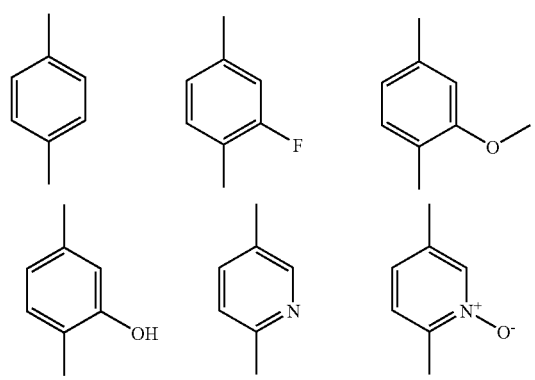

An example of the present invention includes compounds of Formula (I) wherein, A is selected from aryl, heteroaryl, 3-8 numbered carbocycle or 5-8 numbered heterocycle.

Another example of the present invention includes compounds of Formula (I) wherein, A is selected from:

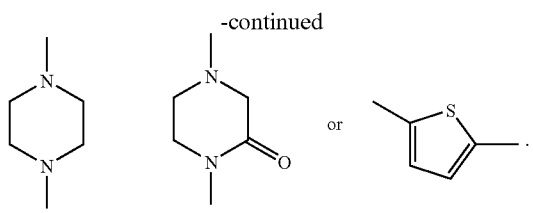

An example of the present invention includes compounds of Formula (I) wherein, K is selected from a bond, ethynyl or NR'.

An example of the present invention includes compounds of Formula (I) wherein, B is selected from aryl, heteroaryl, 3-8 numbered carbocycle or 5-8 numbered heterocycle.

Another example of the present invention includes compounds of Formula (I) wherein, B is selected from:

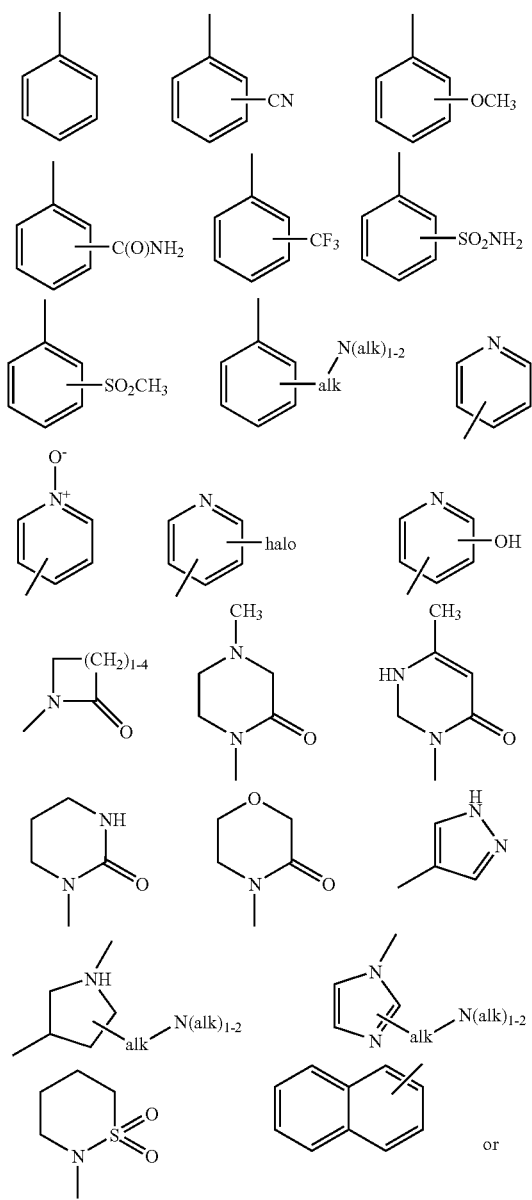

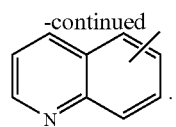

A second aspect of the present invention is directed to pharmaceutical compositions comprising at least one compound of Formula I, or a pharmaceutically acceptable form thereof, and one or more pharmaceutically acceptable excipients.

A third aspect of the present invention is directed to a method of inhibiting Factor Xa, comprising contacting the Factor Xa with or more compounds of Formula I.

A fourth aspect of the invention is directed to a method of inhibiting the effects of Factor Xa, comprising contacting an animal with a composition comprising a pharmaceutically effective amount of at least one compound of Formula I, or a pharmaceutically acceptable form thereof, and one or more pharmaceutically-acceptable excipients.

A fifth aspect of the present invention is directed to a method of treating a Factor Xa associated disorder. The method comprises contacting an animal with a pharmaceutically effective amount of at least one compound of Formula I, or a pharmaceutically acceptable form thereof, and one or more pharmaceutically acceptable excipients.

A sixth aspect of the present invention is directed to describe Factor Xa compounds as inhibitors of Factor Xa.

A seventh aspect of the present invention is to describe Factor Xa compounds that are useful at low dosages as inhibitors of Factor Xa. This therefore leads to a further aspect of compounds having extremely low cytotoxicity.

An eighth aspect of the present invention is directed to methods of synthesizing compounds of Formula I.

These and other aspects and advantages of the invention, which will become apparent in light of the detailed description below, are achieved through use of the compounds of this invention.

DETAILED DESCRIPTION OF THE INVENTION

The present invention provides a compound of Formula I and pharmaceutically acceptable forms thereof:

$$\text{(I)}$$

X is selected from CH, COH, COCH$_3$, N, CF or NO;
Z is selected from CH or N;
A and B are independently selected from ethenyl, ethynyl, aryl, heteroaryl, 3-8 numbered carbocycle or 5-8 numbered heterocycle, each of which can be optionally substituted with 1, 2, 3 or 4 R groups;
K is selected from a bond, ethenyl, ethynyl, NR', O, S, SO$_2$ or CO;
one of Y, P$_1$, P$_2$ or P$_3$ is a bond;
Ring P is selected from:

-continued
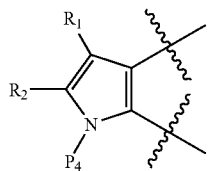 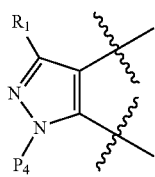 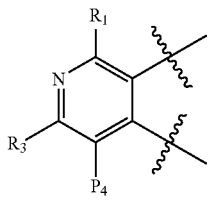 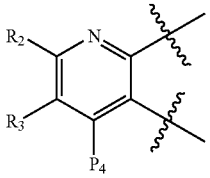
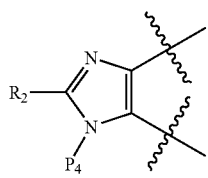 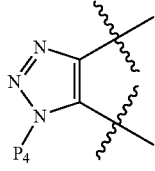 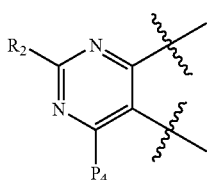 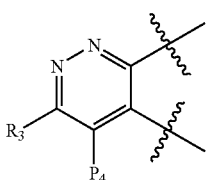
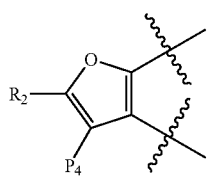 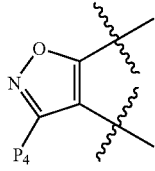 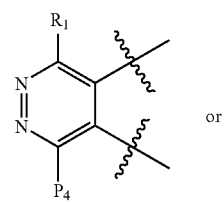 or 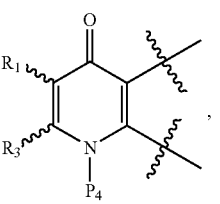,
wherein p is independently selected from 0, 1 or 2,
$P_4$ is selected from:
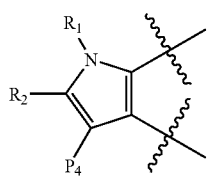 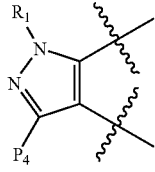 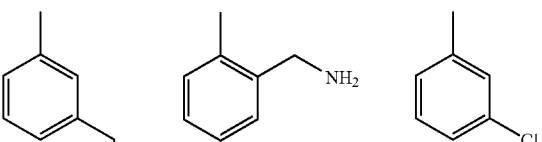
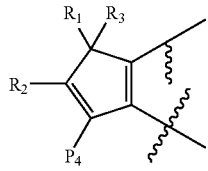 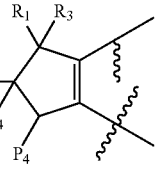 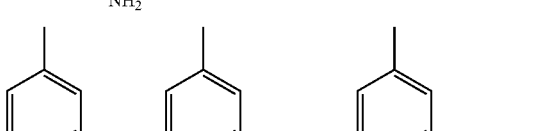
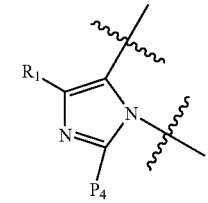 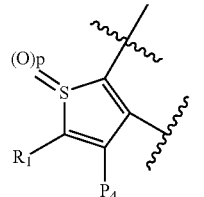 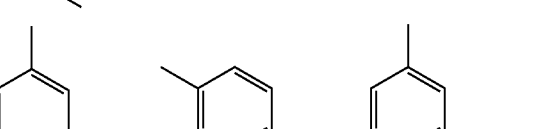
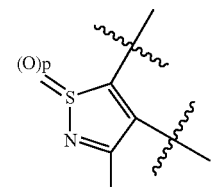 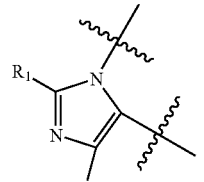 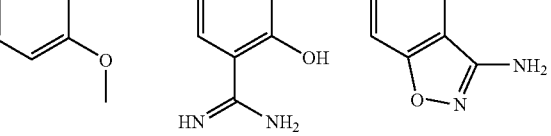
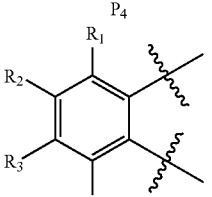 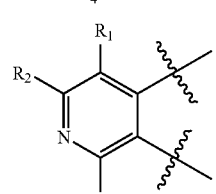 

-continued

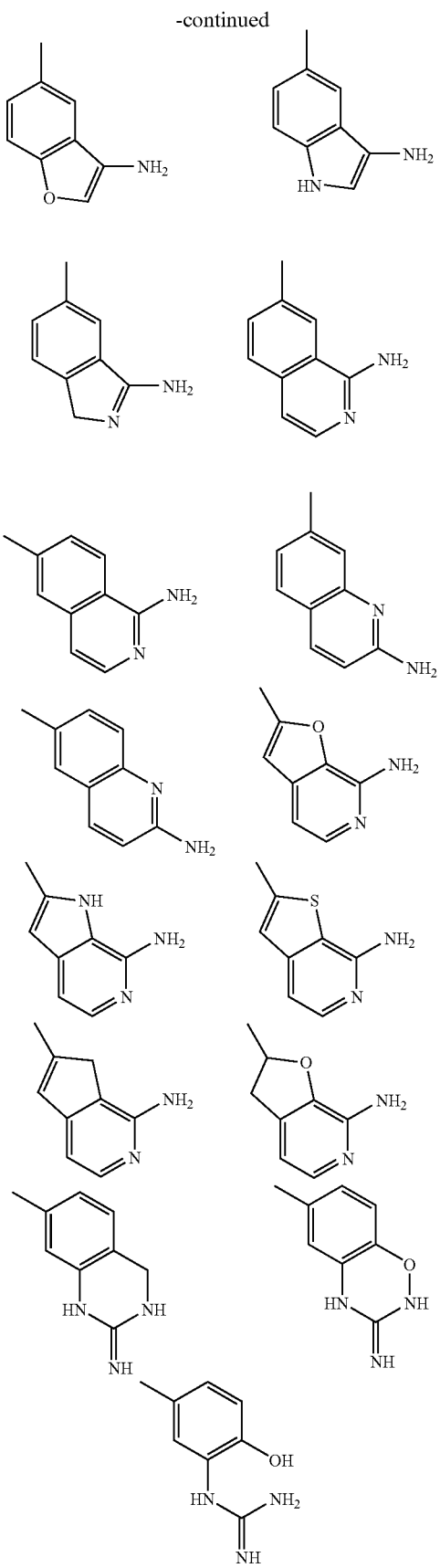
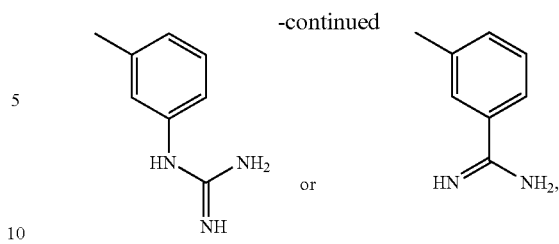

wherein $P_4$ is optionally substituted with 1, 2, 3 or 4 R groups;

$R_1$, $R_2$, and $R_3$ are independently selected from hydrogen, halogen, alkyl, haloalkyl, haloalkoxy, alkenyl, alkynyl, cycloalkyl, $NCH_2R$, $OCH_2R$, $SCH_2R$, $S(O)_pCH_2R$, $C(O)NR$, $OC(O)NR$, $NR^aC(O)NR^aCH_2R$, $NR^aC(O)OCH_2R$, $NR^aC(O)CH_2R$, hydroxyalkyl, cyano, nitro, trifluoromethyl or —$CO_2R$;

provided that $R_1$ forms other than an N—halo, N—N, N—S, N—O, or N—CN bond;

R is selected from hydrogen, halogen, alkyl, alkenyl, alkynyl, cycloalkyl, hydroxy, alkoxy, haloalkyl, haloalkoxy, hydroxyalkyl, cyano, nitro, trifluoromethyl, —$CO_2R^x$, —$CH_2OR^x$ or —$OR^x$, $R^x$ is selected from hydrogen, $C_{1-6}$ alkyl; optionally substituted alkyl, optionally substituted cycloalkyl, optionally substituted aryl or optionally substituted heteroaryl, wherein optionally substituted alkyl, cycloalkyl, aryl and heteroaryl are each optionally substituted with one, two, three or four substituents selected from halogen, hydroxy, amino, mono or dialkyl amino, cyano, nitro, ester, acid or ether;

R' is selected from hydrogen, optionally substituted alkyl, optionally substituted alkenyl, optionally substituted alkynyl, optionally substituted cycloalkyl, optionally substituted $C_{6-10}$aryl, optionally substituted $C_{6-10}$ arylalkyl, optionally substituted heteroaryl or optionally substituted heteroaryl-alkyl, wherein optionally substituted alkyl, alkenyl, alkynyl, cycloalkyl, $C_{6-10}$aryl, the $C_{6-10}$aryl portion of $C_{6-10}$ arylalkyl, heteroaryl and the heteroaryl portion of heteroaryl-alkyl are each optionally substituted with one, two, three or four substituents selected from halogen, hydroxy, carboxy, amino, monoalkylamino, dialkylamino, cyano, nitro, ester, acid or ether; and $R^a$ is selected from hydrogen, $C_{1-4}$alkyl or $C_{6-10}$aryl.

Chemical Definitions

The following definitions apply to the terms as used throughout this specification, unless otherwise limited in specific instances.

The terms "alkyl" or "alk," as employed herein alone or as part of another group, includes both straight and branched chain hydrocarbons containing 1 to 20 carbons, preferably 1 to 12 carbons, more preferably 1 to 8 carbons in the normal chain.

Examples include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the various additional branched chain isomers thereof.

The term "lower alkyl" includes both straight and branched chain hydrocarbons containing 1 to 4 carbons.

The term "alkenyl" as employed herein alone or as part of another group includes both straight and branched hydrocarbons having one or more double bonds, preferably one or two, and being of 2 to 20 carbons, preferably 2 to 12 carbons, and more preferably 2 to 8 carbons in the normal chain. Examples include ethenyl, propenyl and the like.

The term "alkynyl" as employed herein alone or as part of another group includes both straight and branched hydrocarbons having one or more triple bonds, preferably one or two, and being of 2 to 20 carbons, preferably 2 to 12 carbons, and more preferably 2 to 8 carbons in the normal chain. Examples include ethynyl, propynyl and the like.

The term "alkoxy," as employed herein alone or as part of another group, means an "alkyl" groups as defined above bonded to an oxygen, of the formula —O-alkyl.

The term "alkylthio," as employed herein above or as part of another group, means an "alkyl" groups as defined above bonded to a sulfur, of the formula —S-alkyl.

The terms "substituted alkyl," "substituted lower alkyl," "substituted alkenyl" or "substituted alkynyl," refer to such groups as defined above having any number of substituents as allowed by available valences.

The term "amino," as employed herein alone or as part of another group, means a radical of the formula —$NH_2$. The terms "mono or dialkyl amino," "monoalkylamino" or "dialkylamino," as employed herein alone or as part of another group, mean a radical of the formula —NH-alkyl or —N(alkyl)$_2$.

The terms "ester," "acid" or "ether," as employed herein alone or as part of another group, refer to radicals of the formula —C(O)O-alkyl, —C(O)OH or —O-alkyl, respectively, or linking groups of the formula —C(O)O— or —O—. Similarly, the term "alkoxycarbonyl," as employed herein alone or as part of another group, refers to an ester radical of the formula —C(O)O-alkyl.

The term "halo" refers to chloro, bromo, fluoro and iodo.

The terms "haloalkyl" or "haloalkoxy" refer to an alkyl or alkoxy group, respectively, as defined above substituted with any number of halo substituents as allowed by available valences. Typically, the alkyl or alkoxy group has one, two or three halo substituents, for example: trifluoromethyl.

The terms "hydroxyalkyl" or "hydroxyalkoxy" refer to an alkyl or alkoxy group, respectively, as defined above substituted with any number of hydroxy substituents as allowed by available valences.

The terms "cycloalkyl" or "carbocycle," as employed herein alone or as part of another group, refer to a saturated or partially unsaturated (containing 1 or 2 double bonds and/or 1 or 2 triple bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons forming the rings.

Examples include cyclopropyl, cyclobutyl, cyclopentyl, cyclohexyl, cycloheptyl, cyclooctyl, cyclodecyl, cyclododecyl, cyclohexenyl, cyclopentenyl, cyclohexenyl, cycloheptenyl, cyclooctenyl, cyclohexadienyl, cycloheptadienyl and the like.

Also included within the definition of "cycloalkyl" are such rings fused to an aryl, cycloheteroalkyl or heteroaryl ring and bridged multicyclic rings containing 5 to 20 carbons, preferably 6 to 12 carbons, and 1 or 2 bridges.

Further included within the definition of "cycloalkyl" are such groups having one, two or three substituents selected from alkyl, substituted alkyl, halo, hydroxy, amino, mono or dialkyl amino, alkoxycarbonyl, alkoxy, aryl, aryloxy, arylthio, heteroaryl or heterocyclyl.

The term "aryl," as employed herein alone or as part of another group, refers to an unsaturated cyclic ring radical such as phenyl, indenyl, azulenyl, 1-naphthyl, 2-naphthyl, anthracenyl and the like. Specifically included within the term is a $C_{6-10}$aryl ring selected from phenyl, 1-naphthyl, 2-naphthyl and the like.

The terms "heterocyclyl," "heterocycle" or "cycloheteroalkyl," whether used alone or as part of a substituent group, mean a saturated or partially unsaturated cyclic ring radical derived by the removal of one hydrogen atom from a single carbon atom of the ring system and in which one or more ring carbon atoms are a heteroatom selected from N, O, S, SO or $SO_2$. Embodiments include monocyclic or bicyclic rings wherein 1, 2, 3 or 4 members of the ring are a nitrogen atom, or 0, 1, 2 or 3 members of the ring are nitrogen atoms and 1 member is an oxygen or sulfur atom.

Typical heterocyclyl radicals include, and are not limited to, dihydro-1H-pyrrole (including 2-pyrrolinyl or 3-pyrrolinyl), pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, pyran, tetrahydropyranyl, tetrahydrothiopyranyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furyl, tetrahydro-thienyl, tetrahydro-pyranyl, tetrahydro-pyridazinyl, 1,3-benzodioxol-5-yl, 2,3-dihydro-1,4-benzodioxin-6-yl and the like.

The term "heteroaryl," whether used alone or as part of a substituent group, means an unsaturated cyclic ring radical derived by the removal of one hydrogen atom from a single carbon atom of the ring system and in which one or more ring carbon atoms are a heteroatom selected from N, O, S, SO or $SO_2$.

Typical heteroaryl radicals include, and are not limited to, furyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzoxazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "heteroaryl-alkyl," whether used alone or as part of a substituent group, refers to an alkyl radical, as defined above, substituted with any number of heteroaryl substituents as allowed by available valences. Typically, the alkyl group has one heteroaryl substituent.

Compound Forms

The term "forms" and "forms thereof" means that the compounds of the present invention may exist in various salt, stereoisomer, crystalline, solvate, ester, prodrug or active metabolite forms. The present invention encompasses all such compound forms, including active compounds in the form of essentially pure enantiomers, racemic mixtures and tautomers.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

The compounds of Formula I can be prepared as salts, in particular pharmaceutically acceptable salts.

If the compounds of Formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, with saturated or unsaturated dicarboxylic acids, for example oxalic, malonic, succinic, maleic, fumaric, phthalic or terephthalic acid, with hydroxycarboxylic acids, for example ascorbic, glycolic, lactic, malic, tartaric or citric acid, with amino acids, (for example aspartic or glutamic acid or lysine or arginine), or benzoic acid, or with organic sulfonic acids, such as ($C_1$-$C_4$)-alkyl- or aryl-sulfonic acids which are unsubstituted or substituted, for example by halogen, for example methane- or p-toluene sulfonic acid.

Corresponding acid addition salts can also be formed if the compounds of Formula I have an additional basic center. The compounds of Formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of Formula I include monohydrochloride, hydrogensulfate, methanesulfonate, phosphate or nitrate.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of Formula I can exist in enantiomeric or diastereomeric forms or in mixtures thereof. The processes for preparation can utilize racemates, enantiomers or diastereomers as starting materials. When enantiomeric or diastereomeric products are prepared, they can be separated by conventional methods for example, chromatographic or fractional crystallization.

Furthermore, compounds of the invention may have one or more polymorph or amorphous crystalline forms. Said forms are included in the scope of the invention. In addition, some of the compounds may form solvates with water (i.e., hydrates) or common organic solvents. Said solvates are encompassed within the scope of this invention.

Therapeutic Use

The present invention includes a method for inhibiting Factor Xa activity with one or more compounds of formula (I).

The compounds of the present invention are inhibitors of the activated coagulation serine protease known as Factor Xa and thus are useful to maintain the fluidity of blood. Additionally, the compounds of the present invention are useful for the treatment or prophylaxis of Factor Xa associated disorders.

As used herein, the term "Factor Xa disease, disorder or condition" refers to any disease, disorder or condition that may be prevented, partially alleviated or cured by the administration of a Factor Xa inhibitor.

An example or the present invention is a method for use of one or more compounds of formula (I) as a therapeutic agent for treating, preventing or ameliorating a Factor Xa associated disease, disorder or condition in a subject in need thereof comprising administering to the subject an effective amount of one or more compounds of formula (I) or a pharmaceutical composition thereof.

Another example or the present invention includes the use of a compound of formula (I) for the manufacture of a medicament for treating any of the diseases, disorders or conditions in any of the methods disclosed herein.

Accordingly, the present invention is directed to a method for treating, preventing or ameliorating a Factor Xa associated disease, disorder or condition in a subject in need thereof comprising administering to the subject an effective amount of one or more compounds of formula (I) or a pharmaceutical composition thereof.

The method includes administering to the subject an effective amount of a compound of formula (I) or composition thereof in the form of a medicament. Consequently, the invention encompasses the use of the compound of formula (I) as a medicament.

The term "treating, preventing or ameliorating" includes, and is not limited to, facilitating the eradication of, inhibiting the progression of or promoting stasis of a Factor Xa associated disorder.

The term "administering," with respect to the methods of the present invention, refers to a means for treating, ameliorating or preventing a disease, disorder or condition as described herein with a compound specifically disclosed or a compound or prodrug thereof, which would obviously be included within the scope of the invention albeit not specifically disclosed for certain of the instant compounds.

Such methods include prophylactically or therapeutically administering an effective amount of one or more compounds of formula (I) or a composition or medicament thereof at different times during the course of a therapy or concurrently in a combination form. Prophylactic administration can occur prior to the manifestation of symptoms characteristic of a disease or disorder such that the disease or disorder is prevented or, alternatively, delayed in its progression. The instant invention is therefore to be understood as embracing all such regimes of simultaneous or alternating treatment and the term "administering" is to be interpreted accordingly.

The term "prodrug" refers to a metabolic precursor of a compound of formula (I) or pharmaceutically acceptable form thereof. In general, a prodrug is a functional derivative of a compound which may be inactive when administered to a subject but is readily convertible in vivo into an active metabolite compound.

The term "active metabolite" refers to a metabolic product of a compound that is pharmaceutically acceptable and effective. Conventional procedures for the selection and preparation of suitable prodrug derivatives are described, for example, in "Design of Prodrugs", ed. H. Bundgaard, Elsevier, 1985.

The term "subject" as used herein, refers to a patient, such as an animal, preferably a mammal, most preferably a human, who has been the object of treatment, observation or experiment and is at risk of (or susceptible to) developing a Factor Xa associated disease, disorder or condition or having a Factor Xa associated disease, disorder or condition.

The term "effective amount" refers to that amount of active compound or pharmaceutical agent that elicits the biological or medicinal response (such as inhibiting Factor Xa activity) in a tissue system, animal or human, that is being sought by a researcher, veterinarian, medical doctor, or other clinician, which includes treating, preventing or ameliorating the symptoms of the disease, disorder or condition being treated.

The effective amount of a compound of formula (I) exemplified in such a method is from about 0.001 mg/kg/day to about 300 mg/kg/day or has an $IC_{50}$ (50% inhibition concentration) against Factor Xa activity in a range of about 25 µM or less, of about 10 µM or less, of about 1 µM or less, of about 0.5 µM or less, of about 0.25 µM or less or of about 0.1 µM or less.

The term "composition" refers to a product containing a compound of the present invention (such as a product comprising the specified ingredients in the specified amounts, as well as any product which results, directly or indirectly, from such combinations of the specified ingredients in the specified amounts).

The term "medicament" refers to a product for use in treating, preventing or ameliorating a Factor Xa associated disease, disorder or condition.

The term "pharmaceutically acceptable" refers to molecular entities and compositions that are of sufficient purity and quality for use in the formulation of a composition or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

The methods of the present invention further include administering to the subject an effective amount of a combination product comprising one or more compounds of formula (I) or a composition or medicament thereof and at least one other therapeutic agent at different times during the course of a therapy or concurrently as a combination product.

Such a combination product may advantageously facilitate administering to the subject an amount of an agent or a compound of formula (I) that is either or both reduced relative to the amount which would be given in the absence of the other.

Therefore, it is contemplated that the compounds of this invention can be administered to the subject before, during or after the time a particular therapeutic agent is administered Thus, the compounds of the present invention are useful in the treatment or prevention of various Factor Xa associated disorders including: thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequences of surgery, interventional cardiology or immobility; thromboembolic consequences of medication (such as oral contraceptives, hormone replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

The compounds of the present invention may additionally be useful as diagnostic agents and adjuncts. For example, the present compounds may be useful in maintaining whole and fractionated blood in the fluid phase such as required for analytical and biological testing. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

The compounds of the present invention may be used in combination with each other, or with other Factor Xa inhibitors. Additionally, the present compounds may be used in combination with one or more of various other therapeutic agents, including: anti-arrhythmic agents; anti-hypertensive agents; anti-platelet agents, anti-thrombotic and/or anti-thrombolytic agents; calcium channel blockers (L-type and T-type); cardiac glycosides; diuretics, mineralocorticoid receptor antagonists; phosphodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors, Examples of suitable anti-hypertensive agents for use in combination with the compounds of the present invention include: alpha adrenergic blockers; beta adrenergic blockers; calcium channel blockers (e.g. diltiazem, verapamil, nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat and gemopatrilat); and nitrates.

Examples of suitable anti-platelet agents for use in combination with the compounds of the present invention include: GPIIb/IIIa blockers (e.g., abciximab, roxifiban, eptifibatide, tirofiban); P2Y$_{12}$ antagonists (e.g., clopidogrel, ticlopidine, CS-747); thromboxane receptor antagonists (e.g., ifetroban); aspirin; and PDE-III inhibitors (e.g., dipyridamole) with or without aspirin.

Examples of suitable anti-thrombotic and/or anti-thrombolytic agents for use in combination with the compounds of the present invention include: tissue plasminogen activator (natural or recombinant), tenecteplase (TNK), and lanoteplase (nPA); Factor VIIa inhibitors; Factor Xa inhibitors; thrombin inhibitors (such as hirudin and argatroban); PAI-1 inhibitors (i.e., inactivators of tissue plasminogen activator inhibitors); alpha2-antiplasmin inhibitors; streptokinase; urokinase and prourokinase; and anisoylated plasminogen streptokinase activator complex.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diuretics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include spironolactone and eplirinone.

Examples of suitable phosphodiesterase inhibitors for use in combination with the compounds of the present invention include: PDE III inhibitors (such as cilostazol) and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., Glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-coagulants for use in combination with the compounds of the present invention include heparins (e.g., unfractionated and low molecular weight heparins such as enoxaparin and dalteparin).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epithilones, cisplatin, and carboplatin.

Examples of suitable anti-ulcer and gastroesophageal reflux disease agents for use in combination with the compounds of the present invention include famotidine, ranitidine, and omeprazole.

The various other therapeutic agents described above may be employed in the same dosage form with the compound of Formula I or in different dosage forms, in dosages and regimens as generally known in the art or in the PDR.

The compounds of the present invention may act in a synergistic fashion with one or more of the above agents to prevent re-occlusion following a successful thrombolytic therapy and/or reduce the time to reperfusion. The compounds of the present invention may also allow for reduced doses of the thrombolytic agent to be used and therefore minimize potential hemorrhagic side effects.

The compounds of the present invention may also inhibit other serine proteases, for example, thrombin, Factor VIIa, urokinase-type plasminogen activator (urokinase), tryptase and/or trypsin. As a result, these compounds may additionally be useful as angiogenesis inhibitors in the treatment of cancer, as anti-inflammatory agents particularly in the treatment of chronic asthma and in the treatment or prevention of allergic rhinitis, rheumatoid arthritis, inflammatory bowel disease, psoriasis, and conjunctivitis and in the treatment or prevention of pancreatitis.

Pharmaceutical Compositions

An example of the present invention includes a pharmaceutical composition comprising an admixture of one or more compounds of formula (I) and/or one or more pharmaceutically acceptable forms thereof and one or more pharmaceutically acceptable excipients.

The pharmaceutically acceptable forms for a compound of formula (I) include a pharmaceutically acceptable salt, ester, prodrug or active metabolite of a compound of formula (I).

Pharmaceutical compositions according to the invention may, alternatively or in addition to a compound of formula I, comprise as an active ingredient a pharmaceutically acceptable salt of a compound of formula I or a prodrug or pharmaceutically active metabolite of such a compound or salt.

The present invention further includes the use of a process for making the composition or medicament comprising mixing one or more of the instant compounds and an optional pharmaceutically acceptable carrier; and, includes those compositions or medicaments resulting from such a process. Contemplated processes include both conventional and unconventional pharmaceutical techniques.

The composition or medicament may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition or medicament may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation.

Compositions or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Furthermore, compositions or medicaments can be administered in intranasal form via topical use of suitable intranasal vehicles, or via transdermal routes, using, e.g., those forms of transdermal skin patches well known to those of ordinary skill in that art.

Advantageously, a compound of formula (I) may be administered in a single daily dose, or the total daily dosage may be administered in divided doses of two, three or four times daily. Alternatively, the composition or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing the composition or medicament contains an effective amount of the active ingredient necessary to be therapeutically or prophylactically effective as described above.

The compounds of the invention or a composition or medicament thereof can be administered orally or parenterally (such as subcutaneously or intravenously), as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. The composition or carrier will contain about 5 to about 500 mg per unit of dosage of a compound or mixture of compounds. They may be compounded in conventional matter with a physiologically acceptable vehicle or carrier, excipient, binder, preservative, stabilizer, flavorant, etc., as called for by accepted pharmaceutical practice.

For oral administration, the composition or medicament is preferably in the form of a tablet or capsule containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

Optimal dosages will vary depending on factors associated with the particular subject being treated (e.g., age, weight, diet and time of administration), the severity of the condition being treated, the compound being employed, the mode of administration and the strength of the preparation. The use of either daily administration or post-periodic dosing may be employed.

General Synthetic Methods

Schemes I to III outline the synthetic steps to produce compounds of Formula I. The schemes illustrate but are not limited to the preparation of the compounds of Examples 1-95.

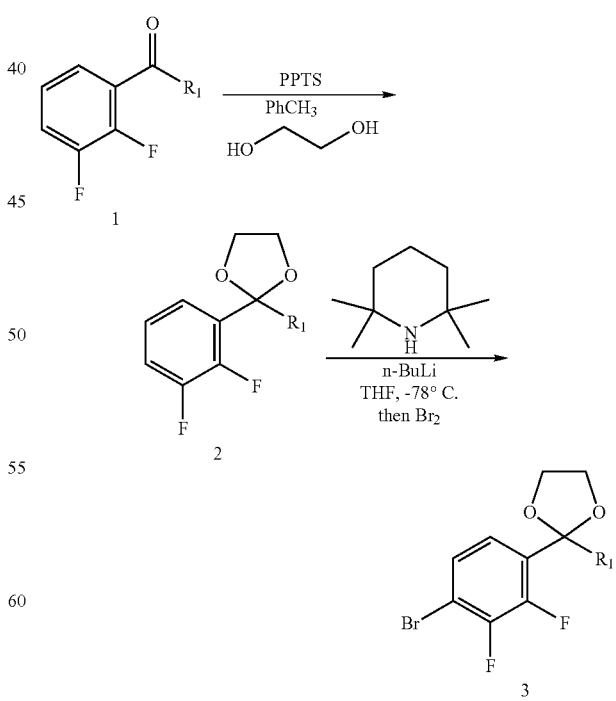

The 2,3-difluoroacetophene compound 1 was first protected with 1,2-dihydroxyethane in the presence of an acid, such as pyridinium p-toluenesulfonate (PPTS) and a suitable solvent, such as toluene, to give the compound 2. The compound 2 was then lithiated with a base, such as n-butyllithium in the presence of an additive, such as 2,2,6,6-tetramethylpiperidine in a solvent such as tetrahydrofuran (THF) at −78° C. and then bromine was added to convert to the brominated compound 3.

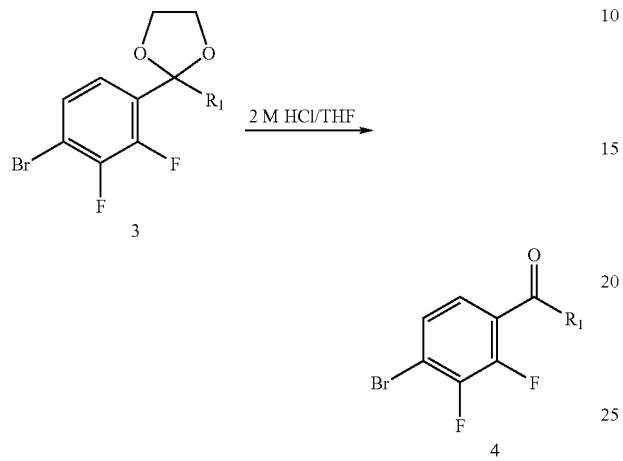

The protecting group was then removed under acidic conditions, such as by adding HCl, in a suitable solvent, such as THF to produce the compound 4.

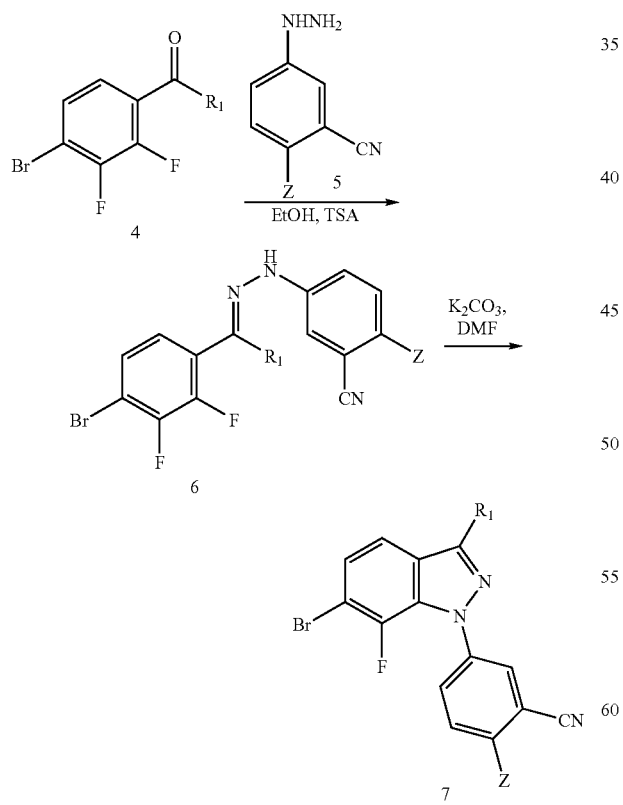

Treatment of 4 with hydrazine 5 catalyzed by an acid, such as p-toluenesulfonic acid, in a solvent, such as ethanol to give compound 6 which was then cyclized to 7 in a basic condition, such as potassium carbonate, and a solvent, such as dimethylformamide (DMF).

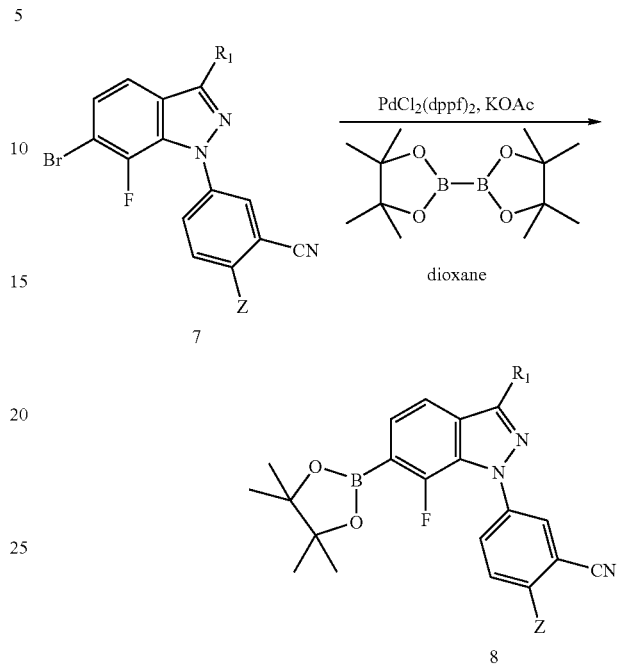

Conversion 7 to the boronate 8 was accomplished by the treatment with bis(pinacolato)diboron in the presence of potassium acetate in dioxane.

Scheme II

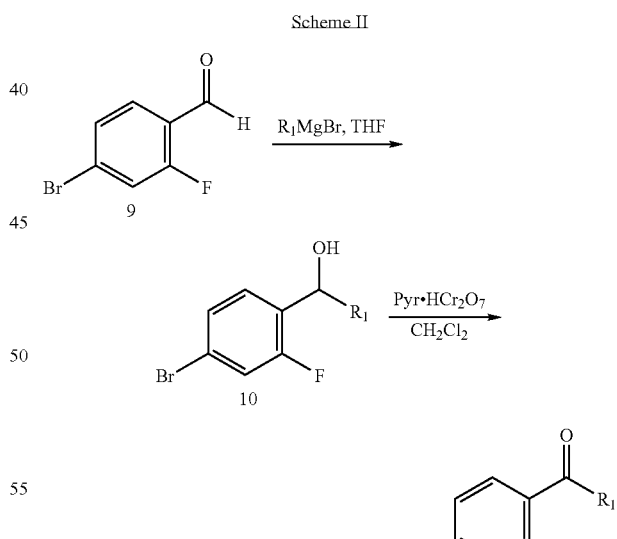

4-bromo-2-fluorobenzene 9 was treated with a methylating agent, such as methyl magnesium bromide, in a suitable solvent, such as tetrahydrofuran (THF) to produce the alcohol 10, which in turn oxidized to the ketone 11 in the present of oxidizing reagent, such as pyridinium dichromate, and a solvent, such as methylene chloride.

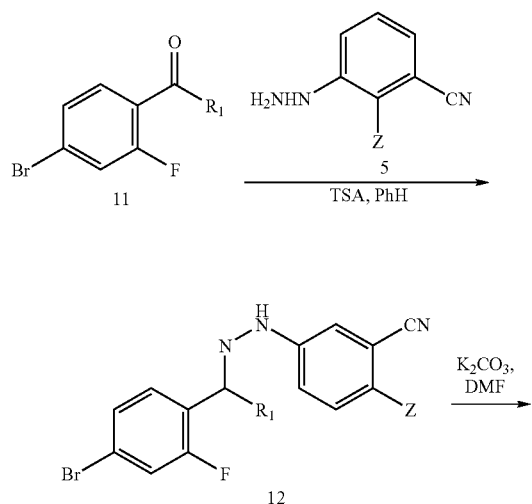

Treatment of 11 with the hydrazine 5 catalyzed by an acid, such as p-toluenesulfonic acid, in a solvent, such as ethanol to give the compound 12 which was then cyclized to 13 in basic conditions, such as potassium carbonate, and a solvent, such as dimethylformamide.

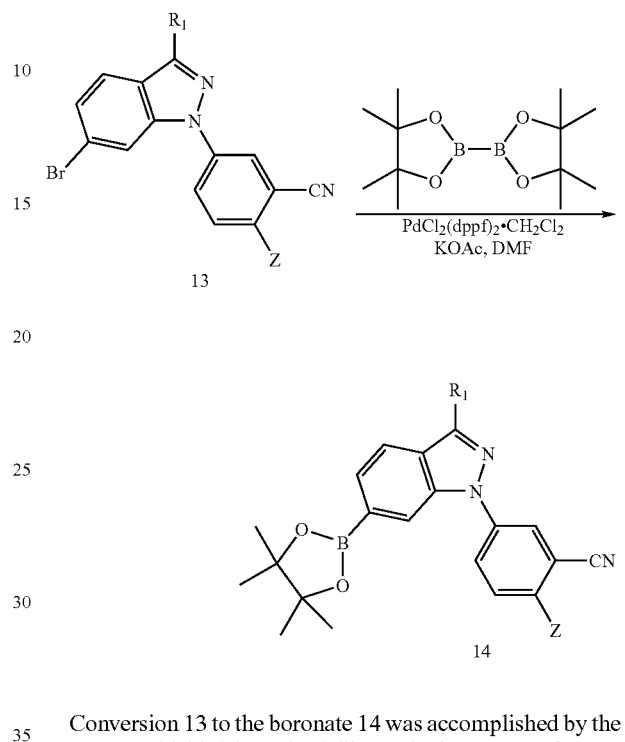

Conversion 13 to the boronate 14 was accomplished by the treatment with bis(pinacolato)diboron in the present of potassium acetate in dioxane.

SCHEME III

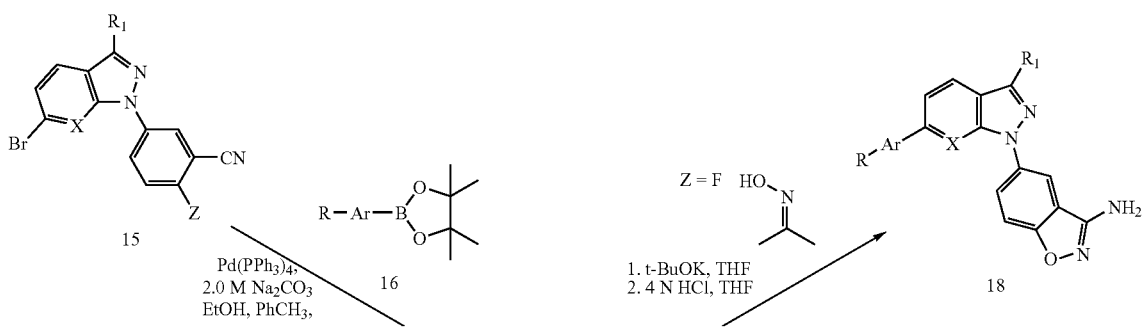

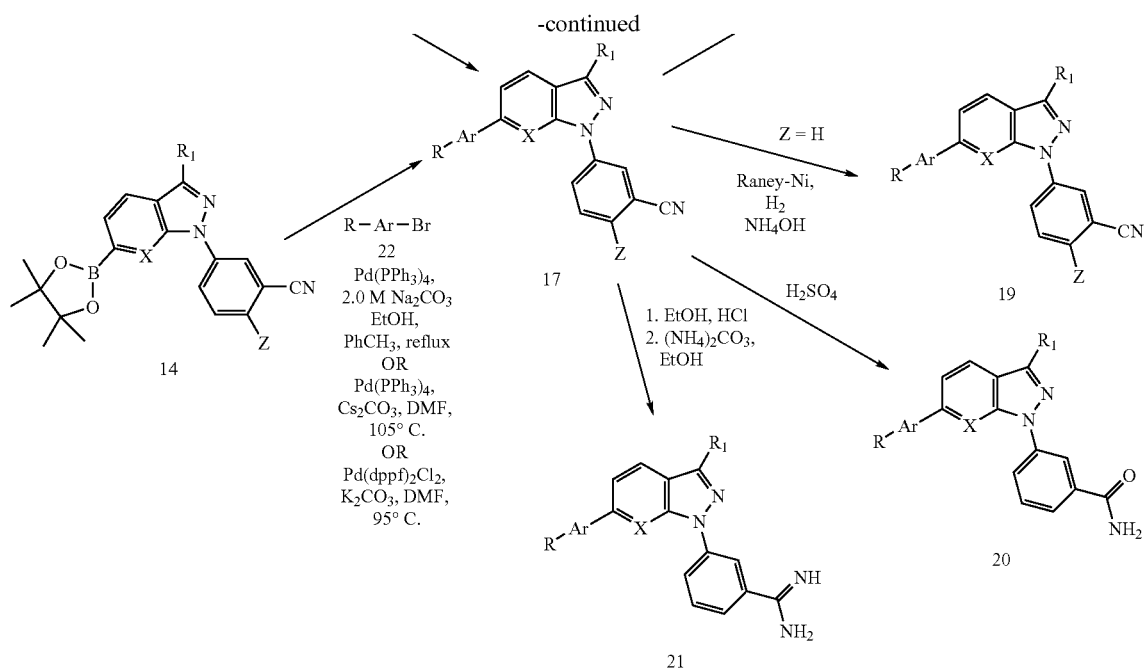

The compound 15 (wherein X=CH, COMe or CF) was treated with the substituted aryl boronates 16 in the present of a catalyst, such as tetrakis (triphenylphosphine)palladium(0), a base, such as sodium carbonate in a suitable solvent or solvent system, such as toluene and ethanol to afford the indazole 17.

Alternatively, the boronate 14 was treated with substituted aryl halides 22 in a suitable catalytic system and solvent system, such as tetrakis(triphenylphosphine) palladium(0) in the presence of sodium carbonate in ethanol and toluene, or tetrakis(triphenylphosphine) palladium(0) in the presence cesium carbonate in dimethylformamide, or dichloro[1,1'-bis (diphenylphosphino)ferrocene]palladium(II) in the presence of potassium carbonate in dimethylformamide to yield the indazole 17.

The indazole 17 (wherein Z is hydrogen) could be treated with acetone oxime, in the presence of a base, such as potassium t-butoxide in a suitable solvent, such as THF and then treated with an acid, such hydrochloric acid in a suitable solvent, such as tetrahydrofuran to afford the aminobenzoisoxazole 18.

The indazole 17 (wherein Z is hydrogen) could be treated with a catalyst, such as Raney nickel, in the presence of a base, such as ammonium hydroxide in a suitable solvent, such as ethanol under a hydrogen atmosphere to yield the amine 19.

Alternatively, the indazole 17 could be treated with an acid, such as sulfuric acid to produce the amide 20.

Furthermore, the indazole 17 could be treated with an acid, such as hydrogen chloride in a suitable solvent, such as ethanol and then treated with an ammonia source, such as ammonium carbonate in a suitable solvent, such as ethanol to afford the amidine 21.

Specific Synthetic Methods

The following working Examples represent preferred embodiments of the present invention.

EXAMPLE 1

1-{4-[1-(3-Amino-benzo[a]isoxazol-5-yl)-7-fluoro-3-methyl-1H-indazol-6-yl]-3-fluoro-phenyl}-1H-pyridin-2-one

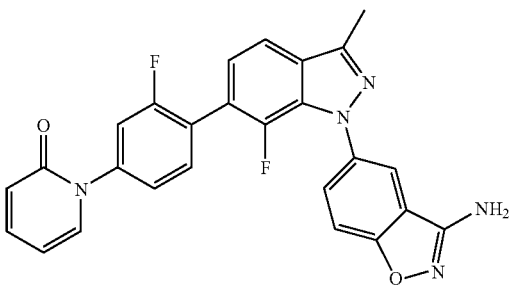

1. Synthesis of 2-Fluoro-5-hydrazino-benzonitrile: To a 200 ml round bottom flask with magnetic stirrer, 5-amino-2-fluorobenzonitrile (5.50 g, 40 mmoles), concentrated HCl (30 ml), and water (30 ml) were added. The mixture was cooled to 0 degree Celsius. NaNO$_2$ (4.80 g, 70 mmoles) in H$_2$O (20 ml) was added drop wise keeping the temperature below 5 degree Celsius. The mixture was stirred for 30 minutes at 0 degree Celsius. To a solution of SnCl$_2$×2H$_2$O (22.5 g, 100 mmoles) in H$_2$O (40 ml) and HCl (10 ml) stirring in a 500 ml Erlenmeyer, the resulting diazonium salt was added at 0 degree Celsius. The reaction mixture was stirred at 0 degree Celsius for 2 hours. The solid was filtered and washed with water (50 ml). The resulting aqueous was basified to pH 8, and extracted with CH$_2$Cl$_2$ (3×200 ml). The combined organic was washed with Brine, dried over Na$_2$SO$_4$, and filtered. The solvent was removed under vacuum to afford an orange solid. The solid was purified via column chromatography with Hexanes/EtOAc (1/1) as eluent to give a yellow solid (1.80 g, 38% yield). ¹H-NMR (400 MHz, CDCl₃): δ 3.64 (br s, 2H), 5.31 (br s, 1H), 7.02-7.06 (m, 2H), 7.01 (dd, J=5.14 Hz, 2.57 Hz, 1H).

2. Synthesis of 1-(4-Bromo-3-fluoro-phenyl)-1H-pyridin-2-one: To a 15 ml round bottom flask equipped with magnetic stirrer and argon inlet, 2-hydroxy-pyridine (100 mg, 1 mmole), 4-bromo-3-fluoro-iodobenzene (430 mg, 1.47 mmoles), CuI (31 mg, 0.016 mmole), Cs₂CO₃ (0.653 mg, 2 mmoles) were added. The reaction flask was purged with argon for 15 minutes. MF (2 ml) was added. The reaction mixture was then heated to 125 degree Celsius for 18 hours. The reaction was partitioned with EtOAc (20 ml), and filtered through Celite. The solvent was then removed under vacuum to give a semi solid. The desired product (100 mg, 37% yield) was isolated via column chromatography with Hexanes/EtOAc (7/3) as eluent. ¹H-NMR (400 MHz, CDCl₃): δ 6.28 (dt, J=6.94 Hz, 1.22 Hz, 1H), 6.68-6.70 (m, 1H), 7.09-7.12 (m, 1H), 7.22-7.31 (m, 2H), 7.40-7.43 (m, 1H), 7.70 (dd, J=8.36 Hz, 7.34 Hz, 1H).

3. Synthesis of 2-(2,3-Difluoro-phenyl)-2-methyl-[1,3]dioxolane: To a 300 ml round bottom flask equipped with stir bar, Dean-Stark trap, and argon inlet, 1(2,3-difluorophenyl) ethanone (10.00 g, 64 mmoles), benzene (100 ml), ethylene glycol (10 ml), and p-toluenesulfonic acid (2.00 g, 10.5 mmoles)were added, respectively. The mixture was heated to reflux for 24 hours. Benzene was then removed under vacuum. The resulting oil was dissolved in EtOAc (500 ml), and washed with NaHCO₃ then Brine. The organic layer was dried over Na₂SO₄, filtered and stripped to afford 12.20 g of oil (95% yield). ¹H-NMR (400 MHz, CDCl₃): δ 3.82-3.92 (m, 2H), 4.06-4.16(m, 2H), 7.01-7.08(m, 1H), 7.09-7.17(m, 1H), 7.24-7.30(m, 1H).

4. Synthesis of 1-(2,3-Difluoro-4-iodo-phenyl)ethanone: To a 3-neck round bottom flask equipped with magnetic stirrer, addition funnel and argon inlet, 2.5M n-BuLi (20 ml, 50 mmoles) and THF (60 ml) were added. The mixture was cooled to −78 degree Celsius. 2,2,6,6-tetramethylpiperidine (7.13 g, 50 mmoles) in THF (20 ml) was added drop wise. The reaction was stirred for half hour. 2-(2,3-Difluoro-phenyl)-2-methyl-[1,3]dioxolane (10.00 g, 50 mmoles) in THF (20 ml) was added drop wise to the reaction mixture with slight exotherm to −70 degree Celsius. The reaction was stirred for one hour at −78 degree Celsius. Iodine (30.00 g/118 mmoles) in THF (30 ml) was added drop wise at −78 degree Celsius. The reaction was allowed to warm to room temperature. Saturated Na₂SO₃ (50 ml) was added. The reaction mixture was extracted with EtOAc (3×100 ml). The combine organic was washed with Brine, dried over Na₂SO₄, and filtered. The resulting EtOAc was removed under vacuum to afford 14.8 g of oil. The oil was dissolved in THF (20 ml) and 3M HCl (40 m). The mixture was heated to 50 degree Celsius for 3 hours, and stirred at room temperature overnight. The organic layer was separated. The aqueous was extracted with CH₂Cl₂ (3×100 ml). The combine organic was washed with Brine, dried over Na₂SO₄, and filtered. The CH₂Cl₂ was removed under vacuum to afford a sticky solid. The sticky solid was washed with Hexanes (3×50 ml) to afford yellow solid (9.04 g, 64% yield). ¹H-NMR (400 MHz, CDCl₃): δ 2.65 (d, J=4.93 Hz, 3H), 7.38-7.45(m, 1H), 7.57-7.63 (m, 1H).

5. Synthesis of 2-Fluoro-5-(7-fluoro-6-iodo-3-methyl-indazol-1-yl)-benzonitrile: To a 100 ml round bottom flask equipped with magnetic stirrer, condenser, and argon inlet, 1-(2,3-Difluoro-4-iodo-phenyl)ethanone (600 mg, 2.1 mmoles), 2-Fluoro-5-hydrazino-benzonitrile (320 mg, 2.1 mmoles), p-toluenesulfonic acid (20 mg, 0.1 mmole) and EtOH (20 ml) were added. The solution was heated to reflux for 3 hours. EtOH was removed under vacuum to afford a solid. The solid was triturated with Hexanes/Et₂O (95/5). The resulting solid was filtered to give a yellow solid (830 mg, 2 mmoles). The solid was then treated with K₂CO₃ (2.78 g, 2 mmoles) and MF (3 ml). The reaction was heated to 100 degree Celsius for 2 hours. The reaction was partitioned with EtOAc (150 ml) and H₂O (30 ml). The organic layer was separated, washed with Brine, dried over Na₂SO₄, and filtered. The solvent was then removed under vacuum to afford a solid. The solid was further purified via column chromatography with Hexanes/EtOAc (8/2) as eluent to give a yellow solid (320 mg, 38% yield). ¹H-NMR (400 MHz, CDCl₃): δ 2.62 (s, 3H), 7.30-7.42 (m, 3H), 7.80-7.91 (m, 2H).

6. Synthesis of 2-Fluoro-5-(7-fluoro-3-methyl-6-(4,4,5,5-tetramethyl-[[1,3,2]dioxaborolan-2-yl)-indazol-1-yl]-benzonitrile: To a 50 ml round bottom flask equipped with magnetic stirrer, condenser, and argon inlet, 2-Fluoro-5-(7-fluoro-6-iodo-3-methyl-indazol-1-yl)-benzonitrile (200 mg, 0.5 mmoles), bis(pinacolato)diboron (190 mg, 0.75 mmole), dichloro[1,1']-bis(diphenylphosphino)ferrocene]palladium (II) dichloromethane adduct (41 mg, 0.05 mmole), and KOAc (147 mg, 1.5 mmoles) were added. The round bottom flask was purged with argon for 15 minutes. Anhydrous dioxane (15 ml) was added. The reaction mixture was heated to 120 degree Celsius for 24 hours. The reaction was allowed to cool to room temperature. The solid was filtered and washed with anhydrous methanol. The organic solvent was removed under vacuum to give a dark solid. The desired product (180 mg, 90% yield) was isolated via column chromatography with Hexanes/EtOAc (8/2) as eluent. ¹H-NMR (400 MHz, CDCl₃/CD₃ID): δ 1.50 (s, 12H), 2.74 (s, 3H), 7.23-8.08 (m, 5H).

7. Synthesis of 2-Fluoro-5-{7-fluoro-6-[2-fluoro-4-(2-oxo-2H-pyridin-1-yl)-phenyl]-3-methyl-indazol-1-yl}-benzonitrile: To a 5 ml round bottom flask equipped with magnetic stirrer, condenser, and argon inlet, 1-(4-Bromo-3-fluoro-phenyl)-1H-pyridin-2-one (17 mg, 0.06 mmole), 2-Fluoro-5-(7-fluoro-3-methyl-6-(4,4,5,5-tetramethyl-[1,3,2]dioxaborolan-2-yl)-indazol-1-yl]-benzonitrile (25 mg, 0.063 mmole), dichloro[1,1']-bis(diphenylphosphino)ferrocene]palladium (II) dichloromethane adduct (5.4 mg, 0.0066 mmole), K₂CO₃ (35 mg, 0.25 mmole) were added. The reaction mixture was purged with argon for 10 minutes. MF (2 ml) was added. The reaction was heated to 100 degree Celsius for 16 hours. The reaction was partitioned with EtOAc (15 ml), and filtered through Celite. The solvent was then removed under vacuum to give a semi solid. The desired product (4.2 mg) was isolated via column chromatography with Hexanes/EtOAc (3/7) as eluent. ¹H-NMR (400 MHz, CDCl₃): δ 2.68 (s, 3H), 6.32-6.41 (m, 1H), 6.61-6.67 (m, 1H), 7.03-7.22 (m, 5H), 7.28-7.40 9 m, 3H), 7.50-7.56 (m, 2H).

8. Synthesis of 1-{4-[1-(3-Amino-benzo[a]isoxazol-5-yl)-7-fluoro-3-methyl-1H-indazol-6-yl]-3-fluoro-phenyl}-1H-pyridin-2-one (TDP-677561-0-1): To a 5 ml round bottom flask equipped with magnetic stirred, and argon inlet, oxime acetone (1 mg, 0.013 mmole), and anhydrous THF (1 ml) were added. KO-t-Bu (1.7 mg, 0.013 mmole) was then added to the reaction mixture, and stirred at room temperature for 10 minutes. 2-Fluoro-5-{7-fluoro-6-[2-fluoro-4-(2-oxo-2H-pyridin-1-yl)-phenyl]-3-methtly-indazol-1-yl}-benzonitrile (4.2 mg, 0.01 mmole) in anhydrous THF (0.5 ml) was added to the reaction mixture, and heated to 50 degree Celsius for 2 hours. The reaction was cooled to room temperature. THF was removed under vacuum to afford a solid. The solid was partitioned with EtOH (2 ml) and 3M HCl (1 ml). The mixture was then heated to 80 degree Celsius for 2 hours. The reaction mixture was concentrated to dryness under high vacuum. The desired product (1.4 mg, 24% yield) was obtained via reverse phase high pressure liquid chromatography (HPLC). ¹H-NMR (400 MHz, CDCl₃): δ 2.69 (s, 3H), 6.37 (dt, J=6.73 Hz, 1.43 Hz, 1H), 6.75-6.80 (m, 1H), 7.20-7.33 (m, 2H), 7.27-7.33 (m, 2H), 7.39-7.42 (m, 1H), 7.46-7.62 (m, 4H), 7.76 (t, J=2.24 Hz, 1H), 7.78-7.83 (m, 1H); Mass spectrum (LCMS, ESI pos.) calcd. for $C_{26}H_{17}F_2N_5O_2$: 470.4 (M+H). Found: 470.1

EXAMPLE 2

3-[7-Fluoro-3-methyl-6-(4-pyridin-2-yl-piperazin-1-yl)-indazol-1-yl]-benzylamine

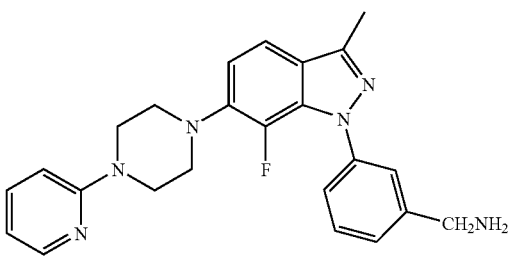

1. 3-Hydrazino-benzonitrile: To a 1 L round bottom flask with magnetic stirrer, 3-aminobenzonitrile (16.11 g, 135 mmoles), concentrated HCl (210 ml), water (210 ml) were added. The mixture was cooled to 0 degree Celsius. NaNO₂ (16.75 g, 240 mmoles) in H₂O (60 ml) was added drop wise keeping the temperature below 5 degree Celsius. The mixture was stirred for 30 minutes at 0 degree Celsius. To a solution of SnCl₂×2H₂O (63.10 g, 280 mmoles) in H₂O (150 ml) and HCl (50 ml) stirring in a 2L Erlenmeyer, the resulting diazonium salt was added at 0 degree Celsius. The reaction mixture was stirred at 0 degree Celsius for 2 hours. The solid was filtered and washed with water (50 ml). The resulting aqueous was basified to pH 9, and extracted with CH₂Cl₂ (3×200 ml). The combined organic was washed with Brine, dried over Na₂SO₄, and filtered. The solvent was removed under vacuum to afford an orange solid. The solid was purified via column chromatography with Hexanes/EtOAc (1/1) as eluent to give a yellow solid (8.84 g, 49% yield). $^1$H-NMR (400 MHz, CDCl₃): δ 3.62 (br s, 2H), 5.40 (br s, 1H), 7.01-7.05 (m,1H), 7.66-7.101 (m, 1H), 7.14-7.16 (m, 1H), 7.27-7.32 (m, 1H).

2. 1-Pyridin-2-yl piperazine: To a 5 ml round bottom flask equipped with magnetic stirrer, condenser, and argon inlet, 2-bromopyridine (320 mg, 2.0 mmole), piperazine (520 mg, 6.0 mmoles), Pd₂ (dba)₃ (46 mg, 0.050 mmole), BINAP (31 mg, 0.10 mmole), NaO-t-Bu (277 mg, 2.8 mmole) were added. The reaction mixture was purged with argon for 10 minutes. Toluene (2.0 ml) was added. The reaction mixture was heated to reflux for 18hrs. The reaction was partitioned with EtOAc, and filtered through Celite. The solvent was then removed under vacuum. The desired product (74 mg, 36% yield) was isolated via column chromatography with CH₂Cl₂/MeOH saturated with NH₃ (9/1) as eluent. $^1$H -NMR (400 MHz, CDCl₃): δ 3.30-3.09 (m, 4H), 3.51-3.59 (m, 4H), 6.64-6.71 (m, 2H), 7.50-7.55 (m, 1H), 8.22-8.27 (m, 1H).

3. 3-(7-Fluoro-6-iodo-3-methyl-indazol-1-yl)-benzonitrile: To a 100 ml round bottom flask equipped with magnetic stirrer, condenser, and argon inlet, 1-(2,3-difluoro-4-iodophenyl)ethanone (4.50 g, 16 mmoles), 3-hydrazino-benzonitrile (2.23 g, 16.7 mmoles), p-toluenesulfonic acid (310 mg, 16.3 mmole) and EtOH (50 ml) were added. The solution was heated to reflux for 3 hours. EtOH was removed under vacuum to afford a solid. The solid was triturated with Hexanes/Et₂O (95/5). The resulting solid was filtered to give a yellow solid (6.40 g, 16 mmoles). The solid was then treated with K₂CO₃ (2.23 g, 16 mmoles) and MF (16 ml). The reaction was heated to 100 degree Celsius for 16 hours. The reaction was partitioned with H₂O (30 ml). The precipitate was filtered, washed with water, and dried under high vacuum to afford a yellow solid (3.70 g, 61% yield). $^1$H-NMR (400 MHz, CDCl₃): δ 2.62 (s, 3H), 7.27 (d, J=8.35 Hz, 1H), 7.52 (dd, J=8.36 Hz, 4.71 Hz, 1H), 7.52-7.67 (m, 2H), 7.80-7.86 (m, 1H), 7.91 (br s, 1H).

4. 3-[7-Fluoro-3-methyl-6-(3',4',5',6'-tetrahydro-2'H-[2,4']bipyridinyl-1'-yl)-indazol-1-yl-benzonitrile: To a 5 ml round bottom flask equipped with magnetic stirrer, condenser, and argon inlet, 3-(7-fluoro-6-iodo-3-methyl-indazol-1-yl)-benzonitrile (189 mg, 0.5 mmole), 1-pyridin-2-yl piperazine (180 mg, 1.1 mmole), Pd₂ (dba)₃ (23 mg, 0.025 mmole), BINAP (31 mg, 0.050 mmole), NaO-t-Bu (69 mg, 0.70 mmole) were added. The reaction mixture was purged with argon for 10 minutes. Toluene (0.5 ml) was added. The reaction mixture was heated to reflux for 18 hrs. The reaction was partitioned with EtOAc, and filtered through Celite. The solvent was then removed under vacuum. The desired product (74 mg, 36% yield) was isolated via column chromatography with Hexanes/EtOAc (7/3) as eluent. $^1$H-NMR (400 MHz, CDCl₃): δ 2.62 (s,3H), 3.33 (t, J=4.93 Hz, 4H), 3.77 (t, J=4.93 Hz, 4H), 6.67-6.71 (m, 1 Hz), 6.74 (d, J=8.79 Hz, 1H), 7.03 (dd, J=8.36 Hz, 6.64 Hz, 1H), 7.44 (d, J=8.57 Hz, 1H), 7.52-7.57 (m, 1H), 7.58-7.65 (m, 2H), 7.86-7.91 (m, 1H), 7.93-7.96 (m, 1H), 8.24-8.26 (m, 1H).

5. 3-[7-Fluoro-3-methyl-6-(4-pyridin-2-yl-piperazin-1-yl)-indazol-1-yl]-benzylamine: To a 500 ml par bottle, 3-[7-fluoro-3-methyl-6 (3',4',5',6'-tetrahydro-2'H-[2,4']bipyridinyl-1'-yl)-indazol-1-yl-benzonitrile (74 mg, 0.18 mmole), NH₄OH (0.2 ml, 5.1 mmoles), Raney's nickel (10 mg), EtOH (10 ml) were added. The reaction mixture was evacuated and purged with hydrogen three times. The reaction was shaken under hydrogen atmosphere at 50 Psi for 4 hours. The reaction was filtered through celite, and, washed with EtOH. The solvent was removed under vacuum. The desired product (40 mg, 54% yield) was obtained via column chromatography with CH₂Cl₂/MeOH (9/1) as eluent. $^1$H-NMR (400 MHz, CDCl₃): δ 2.60 (s, 3H), 3.27 (t, J=4.93 Hz, 4H), 3.72 (t, J=4.93 Hz, 4H), 3.96 (br s, 2H), 6.66 (dd, J=6.86 Hz, 4.93 Hz, 1H), 6.70 (d, J=8.57 Hz, 1H), 6.97 (dd, J=8.79 Hz, 6.43 Hz, 1H), 7.30-7.35 (m, 1H), 7.37-7.47 (m, 3H), 7.50-7.58 (m, 2H), 8.22 (dd, J=8.79 Hz, 4.71 Hz, 1.71 Hz, 1H). Mass spectrum (LCMS, ESI pos.) calcd. for C₂₄H₂₅FN₆: 417.4 (M+H). Found: 417.4.

EXAMPLE 3

1-(3-Amino-benzo[d]isoxazol-5-yl)-6-(2'-dimethylaminomethyl-3-fluoro-biphenyl-4-yl)-7-fluoro-1H-indazole-3-carboxylic acid amide

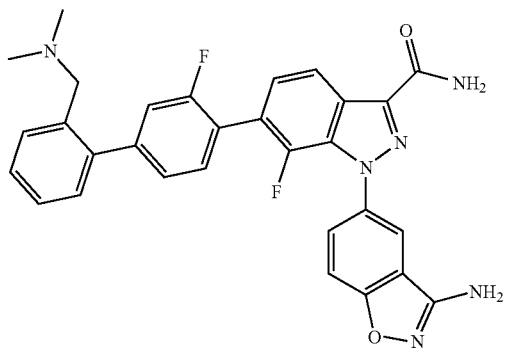

1. 2-(2,3-Difluoro-phenyl)-[1,3]dioxolane: To a solution of 10 g (70.4 mmol) of 2,3-difluoro-benzaldehyde (5.1 mL, 91.5 mmol) of ethylene glycol in 60 mL of benzene was added 1.77 g (7 mmol) of pyridinium p-toluenesulfonate. The resulted mixture was refluxed overnight using a Dean-Stark apparatus. The mixture was allowed to cool to room temperature. Cold water was added to the mixture. The two layers were separated and the aqueous layer was extracted with hexanes for three times. The organic layers were combined and washed with brine. The solution was dried with anhydrous sodium sulfate and filtered. The solvent was removed under reduced pressure to yield 12.9 g (99%) colorless liquid as the desired product. $^1$H-NMR (400 MHz, CDCl$_3$) δ 7.33-7.28 (m, 1H), 7.23-7.08 (m, 2H), 6.12 (s, 1H), 4.21-4.13 (m, 2H), 4.12-4.04 (m, 2H).

2. 2-(2,3-Difluoro-4-iodo-phenyl)-[1,3]dioxolane: To 90 mL of anhydrous THF at −78° C. under argon, 35 mL of 2.17 M n-BuLi was added slowly and then followed by 14 mL (83.2 mmol) of 2,2,6,6-tetramethylpiperidine. The resulted mixture was stirred at the same temperature for 0.5 h. Then the neat 2-(2,3-difluoro-phenyl)-[1,3]dioxolane was added dropwise to the solution at −78° C. The mixture was stirred at the same temperature for addition 2 h. A solution of 21 g (83 mmol) of iodine. in 50 mL of anhydrous THF was prepared and cooled to −78° C. The lithiated difluorobenzene solution was then transferred to the iodine solution at −78° C. using a cannula. The resulted mixture was allowed to warm up to room temperature over about 1.5 h. The mixture was then stirred at room temperature for addition 0.5 h. The brown solution was quenched by poured into a diluted solution of Na$_2$S$_2$O$_3$. The two layers were separated and the aqueous layer was extracted with ethyl acetate twice. The organic layers were combined and washed with brine. The solution was then dried with anhydrous sodium sulfate and filtered. The solvent was removed under reduced pressure to yield a pale orange liquid. $^1$H-NMR (400 MHz, CDCl$_3$) δ 7.49 (ddd, J=1.91, 5.31, 8.22 Hz, 1H), 7.05 (ddd, J=1.66, 6.43, 8.15 Hz, 1H), 6.02 (s, 1H), 4.14-4.07 (m, 2H), 4.06-3.99 (m, 2H).

3. 2,3-Difluoro-4-iodo-benzaldehyde: To a solution of 2-(2,3-difluoro-4-iodo-phenyl)-[1,3]dioxolane in 60 mL THF was added 60 mL of 3.6 N HCl and the mixture was refluxed overnight. The mixture was then was allowed to cool to room temperature. The THF was removed under reduced pressure in a rotovaporator. Yellow precipitate formed in the remaining aqueous solution. The precipitate was then filtered and rinsed with cold water and dried under vacuum. The dried solid was then triturated with 100 mL of hexanes for 15 min. The yellow solid was filtered and dried under vacuum. 14.7 g of yellow solid was obtained as the desired product. $^1$H-NMR (400 MHz, CDCl$_3$) δ 10.33 (s, 1H), 7.69 (dddd, J=0.60, 1.82, 5.04, 8.97 Hz, 1H), 7.42 (ddd, J=1.73, 6.07, 8.40 Hz, 1H).

4. (2,3-Difluoro-4-iodo-phenyl)-trimethylsilanyloxy-acetonitrile: To a solution of 5 g (18.7 mmol) 2,3-difluoro-4-iodo-benzaldehyde in 30 mL anhydrous THF at 0° C., 3 mL (22.3 mmol) of trimethylsilyl cyanide was added slowly to the solution. After the addition was completed, 50 mg of tetrabutylammonium fluoride hydrate was addition to the solution. The mixture was allowed to warm up to warm temperature in 2 h and TLC showed no starting material left. The solvent was removed under reduced pressure. An orange oil was obtained. $^1$H-NMR (400 MHz, CDCl$_3$) δ 7.63 (ddd, J=2.06, 5.33, 8.44 Hz, 1H), 7.22 (ddd, J=1.84, 6.41, 8.30 Hz, 1H), 5.72 (s, 1H), 0.28 (s, 9H).

5. (2,3-Difluoro-4-iodo-phenyl)-hydroxy-acetonitrile: To a solution of (2,3-difluoro-4-iodo-phenyl)-trimethylsilanyloxy-acetonitrile obtained in the previous step in 15 mL of THF, 9 mL of 3N HCl solution was added. The mixture was then heated to 65° C. (oil bath temperature) for 1 h. The mixture was allowed to cool to room temperature and diluted with 10 mL of water. The two layers were separated and the aqueous layer was extracted with ethyl acetate for three times. The organic layers were combined and washed with brine. The solution was then dried with anhydrous sodium sulfate and filtered. The solvent was removed under reduced pressure to yield a yellowish brown solid (5.76 g, quantitative, 2 steps). $^1$H-NMR (400 MHz, CDCl$_3$) δ 7.66 (ddd, J=2.04, 5.31, 8.35 Hz, 1H), 7.23 (ddd, J=1.75, 6.43, 8.39 Hz, 1H), 5.81 (s, 1H), 3.03 (br s, 1H).

6. 2-(2,3-Difluoro-4-iodo-phenyl)-2-hydroxy-acetamide: To a solution of 5.12 g (17.4 mmol) (2,3-difluoro-4-iodo-phenyl)-hydroxy-acetonitrile in 35 mL anhydrous 1,4-dioxane at 0° C. was added 3.5 mL of previously cooled concentrated HCl (0.2 mL of conc. HCl to every mmol of acetonitrile). Anhydrous hydrogen chloride gas was then bubbled to the solution at 0° C. for 30 min. The mixture was then allowed to stand without stirring and warm up to room temperature overnight (Caution: Pressure will build up as the solution warming up!). The orange solution was then poured into ice and cold 5 N NaOH solution was added slowly to mixture at 0° C. until the pH of the solution was 8. The pink solution was then extracted with ethyl acetate three times. The organic layers were combined and washed with brine. The solution was then dried with anhydrous sodium sulfate and filtered. The solvent was removed under reduced pressure to yield 1.95 g pink solid as the desired product. $^1$H-NMR (400 MHz, DMSO-d$_6$) δ 7.65 (ddd, J=1.61, 5.76, 8.29 Hz, 1H), 7.52 (br s, 1H), 7.42 (br s, 1H), 7.07 (ddd, J=1.38, 6.63, 8.29 Hz, 1H), 6.42 (d, J=5.15 Hz, 1H), 5.11 (d, J=5.12 Hz, 1H).

7. 2-(2,3-Difluoro-4-iodo-phenyl)-2-oxo-acetamide: To a solution of 5.15 g (16.4 mmol) of 2-(2,3-difluoro-4-iodo-phenyl)-2-hydroxy-acetamide in 300 mL of anhydrous acetonitrile, 20 g (230 mmol) of activated manganese(IV) oxide was added in one portion. The mixture was stirred at room temperature for 1 h. The mixture was then filtered through a well-packed pad of celite to remove most of the black solid. The filtrate was then filtered one more time on PTFE membrane filter to remove all the black solid. The solvent of the pale yellow filtrate was removed under reduced pressure to yield 3.43 g (67%) of pale yellow solid as the desired product. $^1$H-NMR (400 MHz, CDCl$_3$) δ 7.65 (ddd, J=1.86, 5.10, 8.44 Hz, 1H), 7.50 (ddd, J=1.80, 6.02, 8.43, 1H), 6.84 (br s, 1H), 5.75 (br s, 1H).

8. 2-Fluoro-5-hydrazino-benzonitrile: To a suspension of 4.94 g (36 mmol) of 2-amino-5-fluorobenzonitrile in 60 mL conc. HCl at −10° C. (salt/ice/water bath), a solution of 3.8 g (55 mmol) of sodium nitrite in 20 mL of water was added dropwise to the suspension. The temperature of the reaction should be kept below −5° C. After the addition was completed, the mixture was allowed to stirred at −10° C. for additional 0.5 h. At this point, most of the solid in the suspension should be dissolved. Then a suspension of 22 g (97 mmol) of tin(II) chloride dihydrate in 10 ml of conc. HCl and 10 mL of water was added slowly to the reaction mixture at −10° C. The reaction mixture became thick. The reaction was continued to stir at the same temperature for additional 0.5 h. Then the reaction was neutralized with cold 6.7 N NaOH solution at 0° C. After the addition of the base, a "thick" brown suspension might be formed. It is optional to filter the inorganic tin compounds formed since the filtration would require long time to be finished. Otherwise, the aqueous mixture was extracted with dichloromethane for four times (Note: emulsion might form at this point if the inorganic tin compound wasn't removed). The organic layers were combined and washed with brine. The solution was then dried with anhydrous sodium sulfate and filtered. After removal of the solvent under reduced pressure, 3.08 g of yellow solid was obtained as the crude product. The solid was then chromatographed on a silica gel column using ethyl acetate in dichloromethane (0% to 25%) as eluent. 2.12 g (39%) of yellow solid as the desired hydrazine. $^1$H-NMR (400 MHz, DMSO-d$_6$) δ 7.23 (t, J=9.04 Hz, 1H), 7.12 (br s, 1H), 7.09-7.04 (m, 2H), 4.13 (br s, 2H).

9. 2-[(3-Cyano-4-fluoro-phenyl)-hydrazono]-2-(2,3-difluoro-4-iodo-phenyl)-acetamide: To a solution of 3.43 g (11.1 mmol) of 2-(2,3-difluoro-4-iodo-phenyl)-2-oxo-acetamide in 100 mL anhydrous ethanol, 1.67 g (11.1 mmol) of 2-fluoro-5-hydrazino-benzonitrile and 110 mg (0.55 mmol) of p-toluenesulfonic acid monohydrate were added. The resulted mixture was refluxed for 4 h (oil temperature at 90° C.). Yellow precipitate was formed and the mixture was allowed to cool to room temperature. The orange suspension was then cooled to 0° C. with water/ice bath. The mixture was filtered and the pale yellow solid was rinsed with cold ethanol. The solvent of the filtrate was removed and the residue was triturated with cold ethanol. The mixture was filtered and the yellow solid obtained was combined with the first crop of solid to 3.63 g (74%) pale yellow solid as the desired product. The NMR indicated the yellow solid is a mixture of cis/trans isomer in a ratio of 1:2. The trans-isomer: $^1$H-NMR (400 MHz, DMSO-d$_6$) δ 12.35 (s, 1H), 7.92 (br s, 1H), 7.72-7.62 (m, 4H), 7.44 (t, J=9.07 Hz, 1H), 7.25 (ddd, J=1.52, 6.82, 8.34 H); (cis+trans): $^1$H NMR (400 MHz, DMSO-d$_6$) δ 12.35 (s), 9.98 (s), 8.11 (dd, J=2.87, 5.55 Hz)), 8.02 (br s), 7.92 (br s), 7.77-7.58 (m), 7.44 (t, J=9.10 Hz), 7.40 (t, J=9.10 Hz); 7.31 (br s), 7.25 (ddd, J=1.59, 7.07, 8.42 Hz), 6.95 (ddd, J=1.56, 6.09, 8.14 Hz).

10. 1-(3-Cyano-4-fluoro-phenyl)-7-fluoro-6-iodo-1H-indazole-3-carboxylic acid amide: To a solution of 3.63 g (8.2 mmol) of hydrazone (10) in 60 mL of anhydrous MF was added 1.3 g (9.4 mmol) of potassium carbonate. The mixture was then heated at 100° C. for 2 h. The mixture was allowed to cool to room temperature and then filtered through a pad of Celite. The solvent was removed under reduced pressure. The residue was triturated with dichloromethane overnight and filtered to yield 2.92 g of light brown solid. The solvent of the red filtrate was removed under reduced pressure. The residue was then triturated with cold ethyl acetate for 1 h and filtered to yield another 0.37 g of pale yellow solid. The solid was combined to give 3.28 g (95%) of pale yellow solid as the desired product. $^1$H-NMR (400 MHz, DMSO-d$_6$) δ 8.47 (dt, J=5.62, 2.67 Hz, 1H), 8.22 (ddt, J=4.70, 9.04, 2.87 Hz, 1H), 8.09 (br s, 1H), 7.90 (d, J=8.45 Hz, 1H), 7.81 (t, J=9.01 Hz, 1H), 7.72 (dd, J=5.00, 8.50 Hz, 1H), 7.70 (br s, 1H).

11. 1-(3-Cyano-4-fluoro-phenyl)-7-fluoro-6-(4,4,5,5-tetramethyl-[1,3,2]dioxaborolan-2-yl)-1H-indazole-3-carboxylic acid amide: To a mixture of 105 mg (0.24 mmol) of 1-(3-cyano-4-fluoro-phenyl)-7-fluoro-6-iodo-1H-indazole-3-carboxylic acid amide, 20 mg (0.024 mmol) of Pd(dppf)$_2$Cl$_2$, 90 mg (0.35 mmol) of bis(pinacolato)diboron, 70 mg (0.71 mmol) of potassium acetate under argon, 5 mL anhydrous 1,4-dioxane was added. The mixture was then heated at 110° C. (reflux) for 2 d. The mixture was then allowed to cooled to room temperature and filtered through a pad of Celite. The solvent of filtrate was removed under reduced pressure. The residue was then chromatographed on a silica gel column using 50% ethyl acetate in dichloromethane to yield 92 mg (88%) of light yellow solid as the desired product (The solid can be further purified by triturated with diethyl ether). $^1$H-NMR (400 MHz, DMSO-d$_6$) δ 8.47 (dt, J=5.59, 2.49 Hz, 1H), 8.21 (ddt, J=4.70, 9.06, 2.70 Hz, 1H), 8.10 (d, J=8.16 Hz, 1H), 8.07 (br s, 1H), 7.81 (t, J=9.01 Hz, 1H), 7.69 (br s, 1H), 7.54 (dd, J=4.33, 8.15 Hz, 1H), 1.32 (s, 12H).

12. 4'-Bromo-3'-fluoro-biphenyl-2-carbaldehyde: To a mixture of 500 mg (3.3 mmol) of 2-formylphenylboronic acid, 1.1 g (3.7 mmol) of 1-bromo-2-fluoro-4-iodobenzone, 200 mg (0.17 mmol) of tetrakis(triphenylphosphine)palladium (0) under argon was added 6 ml of anhydrous ethanol, 6 ml of anhydrous toluene and 7 ml of 2.0M sodium carbonate solution. The mixture was heated to 100° C. for 16 hrs. The mixture was allowed to cool and then partitioned between ethyl acetate and water. The aqueous layer was then extracted with ethyl acetate twice. The organic layers were combined, washed with brine and dried anhydrous sodium sulfate. The solvent was removed under reduced pressure. The crude residue was then chromatographed on a silica gel column using a gradient eluent of hexanes to ethyl acetate/hexanes (10%). A white solid (733 mg) was obtained after solvents were removed. $^1$H-NMR (400 MHz, CDCl$_3$) δ 10.00 (s, 1H), 8.04 (dd, J=1.24, 7.78 Hz, 1H), 7.70-7.64 (m, 2H), 7.56 (t, J=7.57, 1H), 7.42 (dd, J=0.69, 7.67 Hz, 1H), 7.19 (dd, J=2.01, 9.02 Hz, 1H), 7.06 (dd, J=1.98, 8.15 Hz, 1H).

13. (4'-Bromo-3'-fluoro-biphenyl-2-ylmethyl)-dimethylamine: To a mixture of 100 mg (0.36 mmol) of 4'-bromo-3'-fluoro-biphenyl-2-carbaldehyde 0.36 ml of 2.0 M dimethylamine in tetrahydrofuran solution in 10 mL of anhydrous MF, 114 mg (0.54 mmol) of sodium triacetoxyborohydride was added. The mixture was then stirred at room temp overnight. The solvents were then removed. The residue was then partitioned between water and ethyl acetate. The aqueous layer was extracted with ethyl acetate twice. The organic layers were combined, washed with brine and dried with anhydrous sodium sulfate. The solvent was removed under reduced pressure. A colorless residue (113 mg) was obtained. The mixture was used in the next step without further purification. $^1$H-NMR (400 MHz, CDCl$_3$) δ 7.66 (dd, J=7.95, 7.57 Hz, 1H), 7.58 (dd, J=7.42, 1.00 Hz, 1H), 7.46 (ddd, J=1.52, 7.44, 7.52 Hz, 1H), 7.43-7.39 (m, 2H), 7.32 (dd, J=1.40, 7.49 Hz, 1H), 7.19 (dd, J=1.84, 8.18 Hz, 1H), 3.38 (s, 2H), 2.27 (s, 6H).

14. 1-(3-Cyano-4-fluoro-phenyl)-6-(2'-dimethylaminomethyl-3-fluoro-biphenyl-4-yl)-7-fluoro-1H-indazole-3-carboxylic acid amide: To a mixture of 38 mg (0.09 mmol) of 1-(3-cyano-4-fluoro-phenyl)-7-fluoro-6-(4,4,5,5-tetramethyl-[1,3,2]dioxaborolan-2-yl)-1H-indazole-3-carboxylic acid amide, 27.6 mg (0.09 mmol of (4'-bromo-3'-fluoro-biphenyl-2-ylmethyl)-dimethyl-amine: 7 mg (0.01 mmol) of dichlorobis(triphenylphosphine) palladium(II) under argon was added 2 mL of anhydrous ME, 2 mL of anhydrous, MF and 0.36 mL of 2.0 sodium carbonate solution. The mixture was heated to 90° C. overnight. The mixture was then allowed to cool to room temperature and filtered through a pad of Celite. The solvent was then removed under reduced pressure. The residue was then partitioned between water and ethyl acetate. The aqueous layer was then extracted with ethyl acetate twice. The organic layers were combined, washed with brine and dried with anhydrous sodium sulfate. The residue was chromatographed on preparative TLC using 0.5% 7N ammonia in methanol solution in ethyl acetate as eluent to yield 27.2 mg of the desired product. $^1$H-NMR (400 MHz, CDCl$_3$) □ 8.35 (d, J=8.37 Hz, 1H), (dt, J=5.31, 2.63 Hz, 1H), 7.94 (m, 1H), 7.68 (d, J=12.01 Hz, 1H), 7.66 (dd, J=1.43, 11.99 Hz, 1H), 7.54 (d, J=7.26 Hz, 1H), 7.49-7.44 (m, 2H), 7.43-7.29 (m, 4H), 6.95 (s, 1H), 5.71 (s, 1H), 3.38 (s, 2H), 2.20 (s, 6H); Mass spectrum (LCMS, ESI pos.) calcd. for $C_{30}H_{22}F_3N_5O$: 526.2 (M+H). Found: 526.0.

15. 1-(3-Amino-benzo[d]isoxazol-5-yl)-6-(2'-dimethylaminomethyl-3-fluoro-biphenyl-4-yl)-7-fluoro-1H-indazole-3-carboxylic acid amide: To a mixture of 37.8 mg (0.072 mmol) of 1-(3-cyano-4-fluoro-phenyl)-6-(2'-dimethylaminomethyl-3-fluoro-biphenyl-4-yl)-7-fluoro-1H-indazole-3-carboxylic acid amide, 16 mg (0.22 mmol) of acetohydroxamic acid, 60 mg (0.43 mmol) of potassium carbonate, 4.9 mL of MF and 0.7 mL of water was added. The mixture was stirred at room temperature overnight. The reaction was then quenched with water. The mixture was extracted with ethyl acetate three time. The organic layers were combined, washed with brine and dried with anhydrous sodium sulfate. The residue was chromatographed on preparative TLC using 7N ammonia in methanol/ethyl acetate/dichloromethane (1:5:5) as eluent to yield 21.6 mg of the desired product. $^1$H-NMR (400 MHz, DMSO-$d_6$) δ 8.21 (d, J=8.42 Hz, 1H), 8.20 (t, J=2.00 Hz, 1H), 8.05 (br s, 1H) 7.93 (dt, J=8.87, 2.16 Hz, 1H), 7.65 (d, J=8.76 Hz, 1H) 7.65 (br s, 1H), 7.59 (t, J=7.90 Hz, 1H), 7.52 (dd, J=1.44, 11.49 Hz, 1H), 7.48 (dd, J=2.32, 13.89 Hz), 1H), 7.46 (d, J=13.97 Hz, 1H), 7.41-7.31 (m, 4H), 6.57 (s, 2H) 3.32 (s, 2H), 2.09 (s, 6H); Mass spectrum (LCMS, ESI pos.) calcd. for $C_{30}H_{24}F_2N_6O_2$: 539.2 (M+H).

Found: 539.1.

The following compounds were prepared in a manner analogous to Examples 1 or 2 or 3.

EXAMPLE 4

1-{4-[7-fluoro-1-(3methoxy-phenyl)-3-methyl-1H-indazol-6-yl]-phenyl}-piperidin-2-one

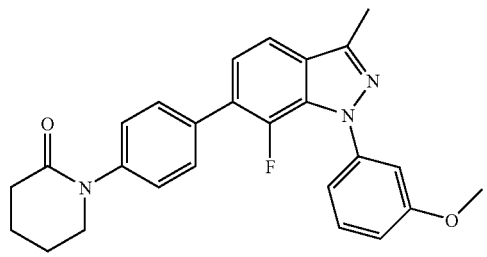

$^1$H-NMR (400 MHz, CDCl$_3$): δ 1.90-2.08 (m, 4H), 2.60 (t, J=6.21 Hz, 2H), 2.66 (s, 3H), 3.69 (t, J=5.79 Hz, 2H), 3.86 (s, 3H), 6.89-6.94 (m, 1H), 7.14-7.25 (m, 3H), 7.32-7.39 (m, 3H), 7.52 (d, J=8.14 Hz, 3H), 7.61 (dd, 2H). Mass spectrum (LCMS, ESI pos.) calcd. for $C_{26}H_{24}FN_3O_2$: 430.4 (M+H). Found: 430.3

EXAMPLE 5

3-{7-Fluoro-3-methyl-6-[4-(2-oxo-piperidin-1-yl)-phenyl]-indazol-1-yl}benzonitrile

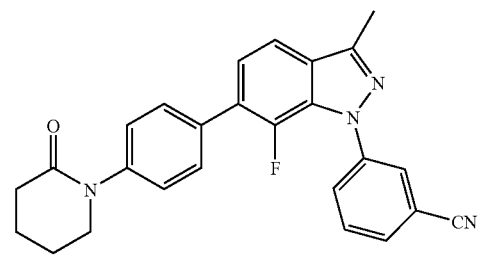

$^1$H-NMR (400 MHz, CDCl$_3$): δ 1.90-2.05 (m, 4H), 2.60 (t, J=6.42 Hz, 2H), 2.66 (s, 3H), 3.80 (t, J=5.78 Hz, 2H), 7.30 (dd, 1H), 7.35-7.41 (m, 2H), 7.51-7.66 (m, 5H), 7.84-7.91 (m, 1H), 7.93-7.98 (m, 1H). Mass spectrum (LCMS, ESI pos.) calcd. for $C_{26}H_{21}FN_4O$: 424.4 (M+H). Found: 424.3.

EXAMPLE 6

1-{4-[1-(3-Aminomethyl-phenyl)7-fluoro-1-3-methyl-1H-indazol-6-yl]-phenyl}-piperidin-2-one

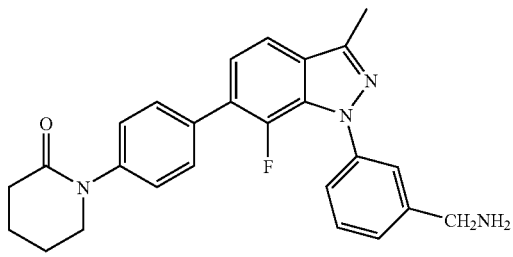

$^1$H-NMR (400 MHz, CDCl$_3$): δ 1.90-2.08 (m, 4H), 2.57 (t, J=6.21 Hz, 2H), 2.62 (s, 3H), 3.68 (t, J =5.78 Hz, 2H), 3.90-4.02 (br s, 2H) 7.22 (dd, 1H), 7.30-7.38 (m, 3H), 7.42 (t, J=7.71 Hz, 1H), 7.43-7.52 (m, 2H), 7.56-7.63 (m, 3H). Mass spectrum (LCMS, ESI pos.) calcd. for $C_{26}H_{25}FN_4O$: 429.2 (M+H). Found: 429.1

EXAMPLE 7

1-{4-[1-(3-Aminomethyl-phenyl)-7-fluoro-1-3-methyl-1H-indazol-6-yl]-phenyl}-pyrolidin-2-one

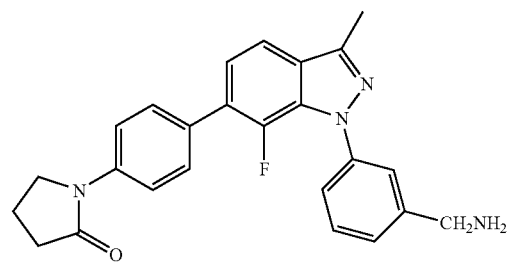

$^1$H-NMR (400 MHz, CD$_3$OD/CDCl$_3$): δ 2.16-2.30 (m, 2H), 2.50-2.80 (m, 5H), 3.80-4.10 (m, 4H), 7.20-7.38 (m, 2H), 7.40-7.80 (m, 8H). Mass spectrum (LCMS, ESI pos.) calcd. for $C_{25}H_{23}FN_4O$: 415.5 (M+H). Found: 415.1.

EXAMPLE 8

3-[7-Fluoro-3-methyl-6-(2'-trifluoromethyl-biphenyl-4-yl)-indazol-1-yl]-benzylamine

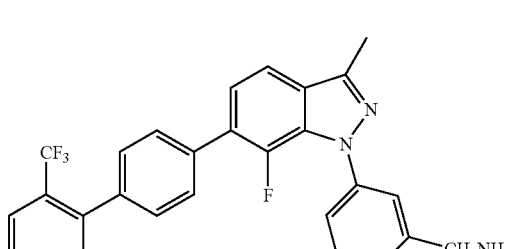

$^1$H-NMR (400 MHz, CDCl$_3$/CD$_3$OD): δ 2.68 (s, 3H), 3.95 (br s, 2H), 7.31-7.55 (m, 8H), 7.56-7.66 (m, 5H), 7.78 (d, 1H, J=7.68). Mass spectrum (LCMS, ESI pos.) calcd. for $C_{28}H_{21}F_4N_3$: 476.5 (M+H). Found: 476.0.

EXAMPLE 9

1-{4-[1-(3-Aminomethyl-phenyl)-7-fluoro-3-methyl-1H-indazol-6-yl]-phenyl}-azetidin-2-one

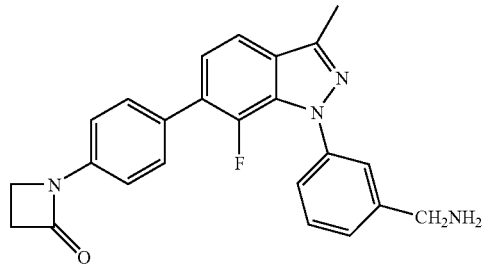

$^1$H-NMR (400 MHz, CDCl$_3$): δ 2.64 (s, 3H), 3.16 (t, J=4.42 Hz, 2H), 3.67 (t, J=4.42 Hz, 2H), 3.96 (br s, 2H), 7.21 (dd, J=8.14 Hz, 6.05 Hz, 1H), 7.31-736 (m, 1H), 7.40-7.60 (m, 8H). Mass spectrum (LCMS, ESI pos.) calcd. for C$_{24}$H$_{21}$FN$_4$O: 401.4 (M+H).
Found: 401.0.

EXAMPLE 10

3-[7-Fluoro-3-methyl-6-(4-pyridin-2-ylethynyl-phenyl)-indazol-1-yl]-benzylamine

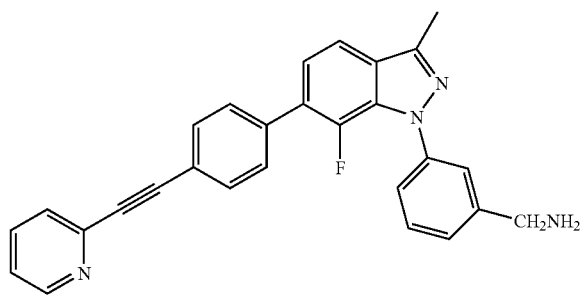

$^1$H-NMR (400 MHz, CDCl$_3$/CD$_3$OD): δ 2.66 (s, 3H), 4.23 (br s, 2H), 7.45 (dd, J=8.36 Hz, 4.93 Hz, 1H), 7.51-7.61 (m, 3H), 7.65-7.76 (m, 3H), 7.86-7.91 (m, 1H), 8.19-8.25 (m, 1H), 8.79-8.85 (m, 1H).

EXAMPLE 11

3-[7-Fluoro-3-methyl-6-(4-pyridin-3-ylethynyl-phenyl)-indazol-1-yl]-benzylamine

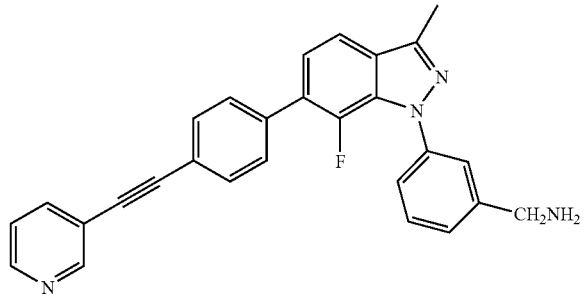

$^1$H-NMR (400 MHz, CDCl$_3$): δ 2.66 (s, 3H), 3.96 (br s, 2H), 7.25-7.38 (m, 3H), 7.43-7.51 (m, 3H), 7.56-7.61 (m, 1H), 7.85 (dt, J=7.93 Hz, 1.93 Hz, 1H), 8.57 (dd, J=4.93 Hz, 1.5 Hz, 1H), 8.80 (d, J=1.32 Hz, 1H).

EXAMPLE 12

3-[7-Fluoro-3-methyl-6-(4-quinolin-2-ylethynyl-phenyl)-indazol-1-yl]-benzylamine

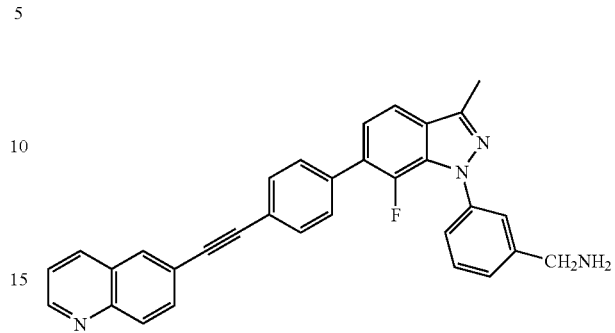

$^1$H-NMR (400 MHz, CDCl$_3$): δ 2.66 (s, 3H), 4.22 (br s, 2H), 7.20-7.28 (m, 6H), 7.31-7.40 (m, 1H), 7.50-7.72 (m, 5H), 7.80-7.92 (m, 1H), 8.17 (d, J=8.37 Hz, 1H), 8.17 (s, 1H), 8.72 (d, J=8.84 Hz, 1H), 8.84-8.92 (m, 1H). Mass spectrum (LCMS, ESI pos.) calcd. for C$_{32}$H$_{23}$FN$_4$: 483.5 (M+H). Found: 483.4.

EXAMPLE 13

3-[7-Fluoro-3-methyl-6-(4-naphthalen-2-ylethynyl-phenyl)-indazol-1-yl]-benzylamine

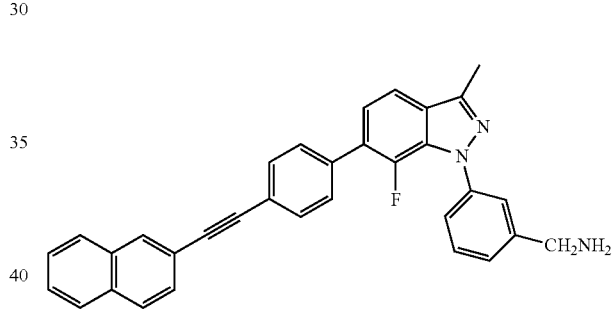

$^1$H-NMR (400 MHz, CDCl$_3$): δ 2.66 (s, 3H), 4.20 (br s, 2H), 7.20-7.28 (m, 6H), 7.30-7.40 (m, 1H), 7.51-7.65 (m, 4H), 7.68-7.73 (m, 1H), 7.94-8.00 (m, 1H), 8.20 (m, J=8.37 Hz, 1H), 8.35 (s, 1H), 8.72 (d, J=8.83 Hz, 1H), 8.84-8.91 (m, 1H), 9.14-9.21 (m, 1H).
Mass spectrum (LCMS, ESI pos.) calcd. for C$_{33}$H$_{24}$FN$_3$: 482.5 (M+H). Found: 482.5.

EXAMPLE 14

3-[7-Fluoro-3-methyl-6-(4-imidazol-1-yl-phenyl)-indazol-1-yl]-benzylamine

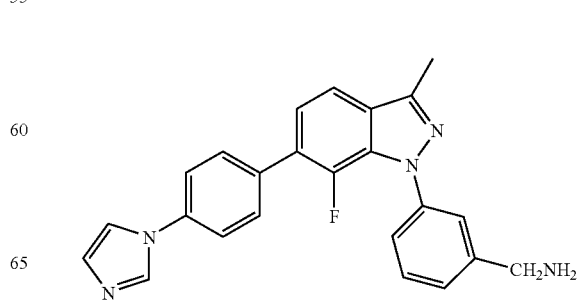

¹H-NMR (400 MHz, CDCl₃/CD₃OD): δ 2.75 (s, 3H), 3.96 (br s, 2H), 7.22 (s, 1H), 7.26 (dd, J=8.35 Hz, 6.00 Hz, 1H), 7.33-7.38 (m, 2H), 7.44-7.52 (m, 4H), 7.56-7.60 (m, 2H), 7.69-7.73 (m, 2H), 7.93 (br s, 1H). Mass spectrum (LCMS, ESI pos.) calcd. for $C_{24}H_{20}FN_5$: 398.4 (M+H). Found: 398.1.

EXAMPLE 15

6{4-1-(3-Aminomethyl-phenyl)-7-fluoro-3-methyl-1H-indazol]-phenylethynyl-benzothiazol-2-ylamine

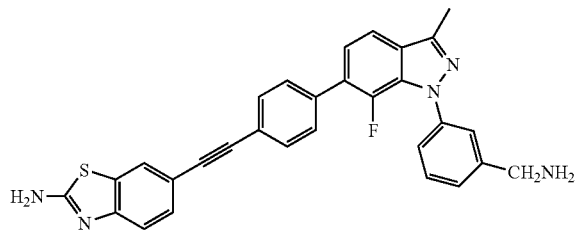

¹H-NMR (400 MHz, CDCl₃/CD₃OD): δ 2.68 (s, 3H), 3.98 (br s, 2H), 7.22 (br s, 1H), 7.26 (dd, J=8.36 Hz, 5.29 Hz, 1H) 7.37 (m, 2H), 7.44-7.52 (m, 4H), 7.56-7.60 (m, 2H), 7.69-7.74 (m, 2H), 7.93 (br s, 1H).

EXAMPLE 16

3-[7-Fluoro-3-methyl-6-(4-pyridin-2-yl-piperazin-1-yl)-indazol-1-yl]-benzylamide

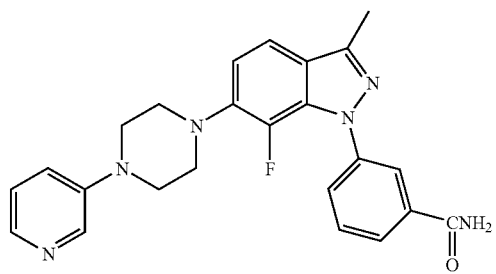

¹H-NMR (400 MHz, CDCl₃): δ 1.90 (br s, 2H), 2.62 (s, 3H), 3.30-3.44 (m, 8H), 7.01 (dd, J=8.57 Hz, 6.64 Hz, 1H), 7.18-7.28 (m, 2H), 7.44 (d, J=8.57 Hz, 1H), 7.57 (t, J=7.92 Hz, 1H), 7.74-7.80 (m, 1H), 7.83-7.86 (m, 1H), 8.04-8.08 (m, 1H), 8.13-8.18 (m, 1H), 8.38 (d, J=2.36 Hz, 1H). Mass spectrum (LCMS, ESI pos.) calcd. for $C_{24}H_{23}FN_6O$: 431.5 (M+H). Found: 431.2.

EXAMPLE 17

3-[7-Fluoro-3-methyl-6-(4-pyridin-3-yl-piperazin-1-yl)-indazol-1-yl]-benzylamine

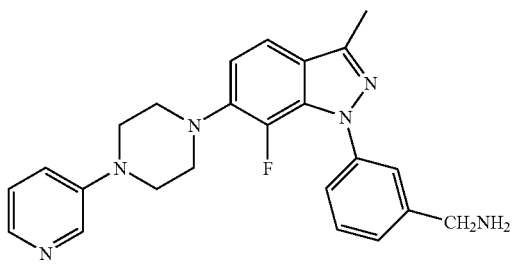

¹H-NMR (400 MHz, CDCl₃): δ 2.60 (s, 3H), 3.30-3.42 (m, 8H), 3.90 (br s, 2H), 6.98 (dd, J=8.39 Hz, 6.64 Hz, 1H), 7.19-7.25 (m, 2H), 7.30-7.34 (m, 1H), 7.40-7.47 (m, 3H), 7.49-7.58 (m, 1), 8.15 (br s, 1H), 8.35 (br s, 1H). Mass spectrum (LCMS, ESI pos.) calcd. for $C_{24}H_{25}FN_6$: 417.5 (M+H). Found: 417.1.

EXAMPLE 18

3-{7-Fluoro-6-[4-(3-methoxy-phenyl)-piperazin-1-yl)-3-methyl-indazol-1-yl]-benzylamine

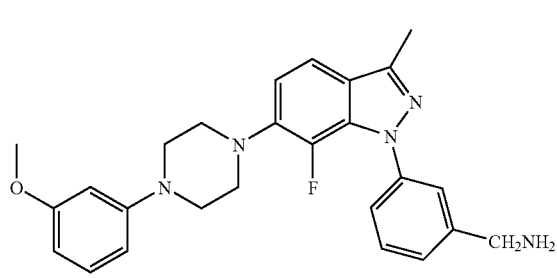

¹H-NMR (400 MHz, CDCl₃): δ 2.58 (s, 3H), 3.27-3.37 (m, 8H), 3.80 (s, 3H), 3.98 (br s, 2H), 6.45 (dd, J=8.60 Hz, 1.86 Hz, 1H), 6.52 (t, J=2.33 Hz, 1H), 6.59 (dd, J=9.07 Hz, 3.02 Hz, 1H), 6.97 (dd, J=8.60 Hz, 6.75 Hz, 1H), 7.20 (t, J=8.37 Hz, 1H), 7.30-7.35 (m, 1H), 7.37-7.46 (m, 3H), 7.54-7.58 (m, 1H). Mass spectrum (LCMS, ESI pos.) calcd. for $C_{26}H_{28}FN_5O$: 446.5 (M+H). Found: 446.0.

EXAMPLE 19

3-{7-Fluoro-6-[4-(3-fluoro-benzyl)-piperazin-1-yl)-3-methyl-indazol-1-yl]-benzylamine

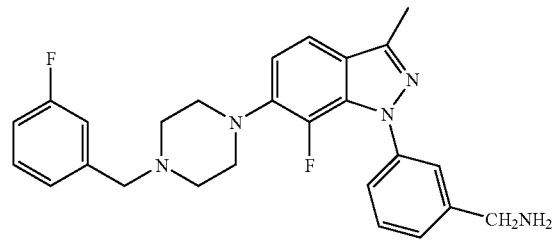

¹H-NMR (400 MHz, CDCl₃): δ 2.58 (s, 3H), 2.64 (t, J=4.90 Hz, 4H), 3.18 (t, J=4.90 Hz, 4H), 3.57 (s, 2H), 3.96 (br s, 2H), 6.90-6.99 (m, 2H), 7.08-7.13 (m, 2H), 7.25-7.33 (m, 3H), 7.37 (d, J=8.37 Hz, 1H), 7.41-7.45 (m, 1H), 7.52-7.56 (m, 1H). Mass spectrum (LCMS, ESI pos.) calcd. for $C_{26}H_{27}F_2N_5$: 448.5 (M+H). Found: 448.1

EXAMPLE 20

3-{7-Fluoro-6-[4-(3-methoxy-benzyl)-piperazin-1-yl)-3-methyl-indazol-1-yl]-benzylamine

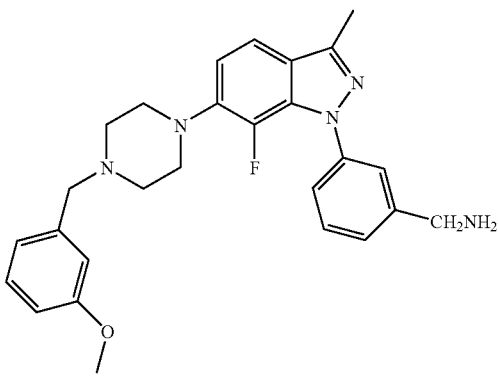

¹H-NMR (400 MHz, CDCl₃): δ 2.62 (s, 3H), 2.83 (t, J=5.58 Hz, 2H), 3.37 (s, 2H), 3.61 (s, 2H), 3.67 (t, J=5.58 Hz, 2H), 3.82 (s, 3H), 3.96 (s, 2H), 6.81-6.86 (m, 1H), 6.91-6.96 (m, 2H), 7.06 (dd, J=8.37 Hz, 5.81 Hz, 1H), 7.30-7.34 (m, 1H), 7.40-7.45 (m, 4H), 7.69-7.74 (m, 1H). Mass spectrum (LCMS, ESI pos.) calcd. for $C_{27}H_{30}FN_5O$: 460.5 (M+H). Found: 460.1.

EXAMPLE 21

1-[1-(3-Aminomethyl-phenyl)-7-fluoro-3-methyl-1H-indazol-6-yl]-4-pyridin-3-yl-piperazin-2-one

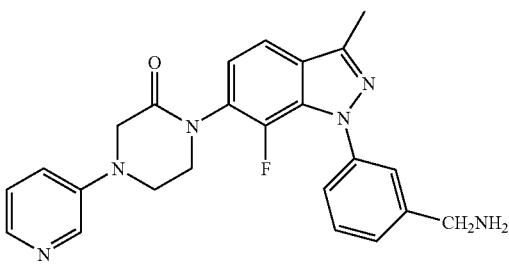

¹H-NMR (400 MHz, CDCl₃): δ 2.66 (s, 3H), 3.72 (t, J=4.71 Hz, 2H), 3.91 (t, J=4.71 Hz, 2H), 3.98 (s, 2H), 4.14 (s, 2H), 7.11 (dd, J=8.36 Hz, 5.79 Hz, 1H), 7.16-7.27 (m, 2H), 7.32-7.37 (m, 1H), 7.42-7.51 (m, 2H), 7.53-7.60 (m, 2H), 8.20 (d, J=3.86 Hz, 1H), 8.34-8.38 (m, 1H). Mass spectrum (LCMS, ESI pos.) calcd. for $C_{24}H_{23}FN_6O$: 431.5 (M+H). Found: 431.1.

EXAMPLE 22

1-[1-(3-Aminomethyl-phenyl)-7-fluoro-3-methyl-1H-indazol-6-yl]-4-(2-methyanesulfonyl-phenyl)-piperazine-2-one

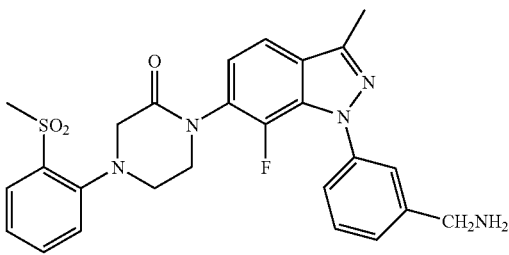

¹H-NMR (CDCl₃): δ 2.66 (s, 3H), 3.35 (s, 3H), 3.57 (s, 2H), 3.50-3.57 (m, 2H), 3.84-3.93 (m, 2H), 3.97-4.03 (m, 4H), 7.12 (dd, J=8.37 Hz, 5.81 Hz, 1H), 7.35-7.39 (m, 1H), 7.42-7.52 (m, 4H), 7.57 (d, J=8.37 Hz, 1H), 7.59-7.62 (m, 1H), 7.68-7.75 (m, 1H), 8.17 (dd, J=7.91 Hz, 1.40 Hz, 1H). Mass spectrum (LCMS, ESI pos.) calcd. for $C_{26}H_{26}FN_5O_3S$: 508.6 (M+H). Found: 508.1.

EXAMPLE 23

4-[1-(3-aminobenzo[a]isoxazol-5-yl)-7-fluoro-3-methyl-1H-indazol-6-yl]-3'-fluoro-biphenyl-2-sulfonic acid amide

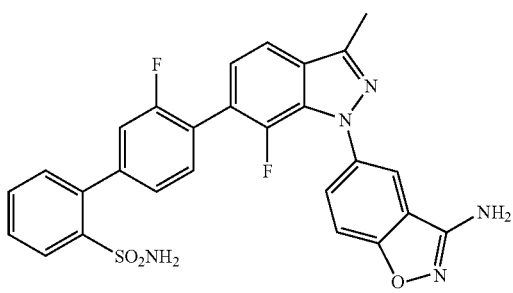

¹H-NMR (400 MHz, CD₃OD): δ 2.67 (s, 3H), 7.29-7.36 (m, 3H), 7.39 (dd, J=7.44 Hz, 1.16 Hz, 1H), 7.48-7.55 (m, 3H), 7.57 (dd, J=7.68 Hz, 1.63 Hz, 1H), 7.64 (dt, J=8.80 Hz, 1.16 Hz, 1H), 7.71 (d, J=8.37 Hz, 1H), 7.78 (td, J=8.84 Hz, 2.32 Hz, 1H), 8.00 (t, J=2.33 Hz, 1H), 8.13 (dd, J=1.16 Hz, 1H). Mass spectrum (LCMS, ESI pos.) calcd. for $C_{27}H_{19}F_2N_5O_3S$: 532.5 (M+H). Found: 532.1.

EXAMPLE 24

5-{6-[4-(2-Dimethylaminomethyl-imidazole-1-yl)-2-fluorophenyl]-7-fluoro-3-methyl-indazol-1-yl}benzo[a]isoxazol-3-ylamine

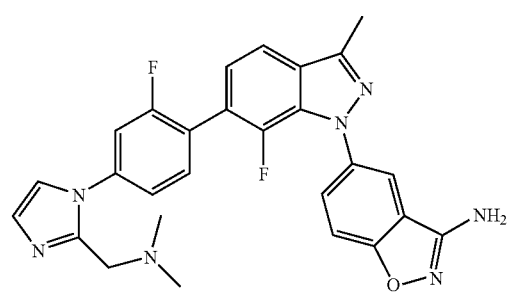

¹H-NMR (400 MHz, CDCl₃): δ 2.30 (s, 6H), 2.69 (s, 3H), 3.45 (s, 2H), 4.48 (br s, 2H), 7.12 (d, J=1.40 Hz, 1H), 7.16 (d, J=1.40 Hz, 1H), 7.21-7.26 (m, 1H), 7.45-7.56 (m, 3H), 7.61 (d, J=8.14 Hz, 1H), 7.70 (dd, J=8.84 Hz, 1.86 Hz, 1H), 7.75-7.81 (m, 2H). Mass spectrum (LCMS, ESI pos.) calcd. for $C_{27}H_{23}F_2N_7O$: 500.5 (M+H). Found: 500.1.

EXAMPLE 25

1-{4-[1-(3-Amino-benzo[a]isoxazol-5-yl)-7-fluoro-3-methyl-1H-indazol-6-yl]-3-fluoro-phenyl}-1H-pyridin-2-one

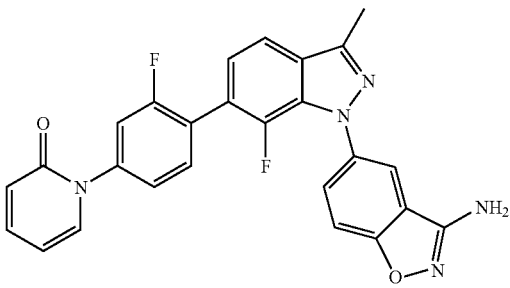

$^1$H-NMR (400 MHz, CDCl$_3$): δ $^1$H-NMR (CDCl$_3$): δ 2.69 (s, 3H), 6.37 (dt, J=6.73 Hz, 1.43 Hz, 1H), 6.75-6.80 (m, 1H), 7.20-7.33 (m, 2H), 7.27-7.33 (m, 2H), 7.39-7.42 (m, 1H), 7.46-7.62 (m, 4H), 7.76 (t, J=2.24 Hz, 1H), 7.78-7.83 (m, 1H); Mass spectrum (LCMS, ESI pos.) calcd. for C$_{26}$H$_{17}$F$_2$N$_5$O$_2$: 470.4 (M+H). Found: 470.1

EXAMPLE 26

1-{4-[1-(3-Amino-benzo[a]isoxazol-5-yl)-7-fluoro-3-trifluoromethyl-1H-indazol-6-yl]-3-fluoro-phenyl}-1H-pyridin-2-one

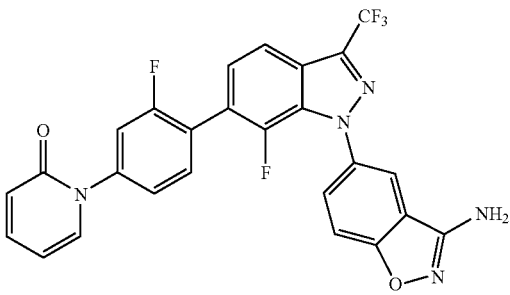

$^1$H-NMR (400 MHz, CDCl$_3$): δ 6.59 (dt, J=6.73 Hz, 1.22 Hz, 1H), 6.99 (d, J=9.18 Hz, 1H), 7.32-7.37 (m, 2H), 7.43 (dd, J=5.51 Hz, 2.86 Hz, 1H), 7.51 (dd, J=5.51 Hz, 1.43 Hz, 1H), 7.58-7.64 (m, 2H), 7.64-7.70 (m, 1H), 7.82-7.92 (m, 3H). Mass spectrum (LCMS, ESI pos.) calcd. for C$_{26}$H$_{14}$F$_5$N$_5$O$_2$: 524.4 (M+H). Found: 524.1.

EXAMPLE 27

1-(3-Amino-benzo[a]isoxazol-5-yl)-7-fluoro-6-[2-fluoro-4-(2-oxo-2H-pyridin-1-yl)-phenyl]-1H-indazole-3-carboxylic acid amide

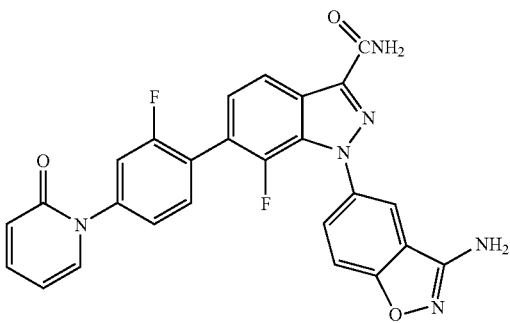

$^1$H-NMR (400 MHz, DDMSO-d$_6$) δ 6.36 (dt, J=6.73 Hz, 1.22 Hz, 1H), 6.52 (d, J=9.00 Hz, 1H), 6.58 (br s, 2H), 7.41-7.49 (m, 2H), 7.51-7.61 (m, 2H), 7.64-7.77 (m, 4H), 7.95 (dt, J=9.00 Hz, 2.25 Hz, 1H), 8.07 (br s, 1H), 8.21 (t, J=2.24 Hz, 1H), 8.24 (d, J=8.36 Hz, 1H). Mass spectrum (LCMS, ESI pos.) calcd. for C$_{26}$H$_{16}$F$_2$N$_6$O$_3$:498.4 (M+H). Found: 499.1.

EXAMPLE 28

1-(3-Amino-benzo[a]isoxazol-5-yl)-7-fluoro-6-(2-oxo-2H[1,3']-bipyridinyl-6'-yl)-1H-indazole-3-carboxylic acid amide

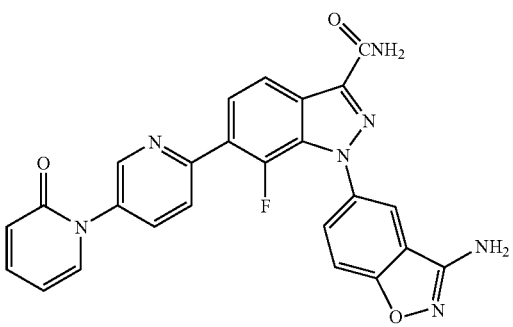

$^1$H-NMR (DMSO): δ 6.36 (dt, J=6.73 Hz, 1.22 Hz, 1H), 6.52 (d, J=9.00 Hz, 1H), 6.58 (br s, 2H), 7.41-7.49 (m, 2H), 7.51-7.61 (m, 2H), 7.64-7.77 (m, 4H), 7.94 (dt, J=9.00 Hz, 2.45 Hz, 1H), 8.07 (br s, 1H), 8.20 (t, J=2.24 Hz, 1H), 8.24 (d, J=8.36 Hz, 1H).

Mass spectrum (LCMS, ESI pos.) calcd. for C$_{25}$H$_{16}$FN$_7$O$_3$: 482.4 (M+H). Found: 482.1.

EXAMPLE 29

6'-[1-(3-Amino-benzo[a]isoxazol-5-yl)-7-fluoro-3-trifluoromethyl-1H-indazol-6-yl]-[1,3']bipyridinyl-2-one

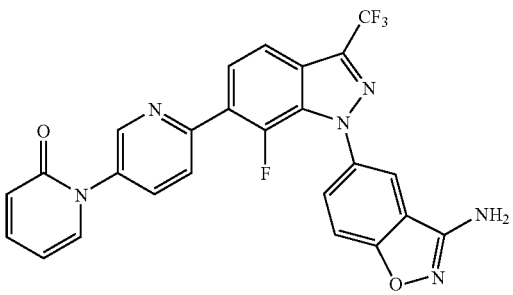

$^1$H-NMR (400 MHz, DDMSO-d$_6$) δ 6.40 (dt, J=6.94 Hz, 1.22 Hz, 1H), 6.52-6.57 (m, 1H), 6.62 (br s, 2H), 7.54-7.60 (m, 1H), 7.69 (d, J=8.98 Hz, 1H), 7.80 (dd, J=4.90 Hz, 2.04 Hz, 1H), 7.92 (d, J=8.36 Hz, 1H), 7.94-8.10 (m, 4H), 8.27 (t, J=1.63 Hz, 1H), 8.85 (d, J=2.45 Hz, 1H). Mass spectrum (LCMS, ESI pos.) calcd. for C$_{25}$H$_{14}$F$_4$N$_6$O$_2$: 507.4 (M+H). Found: 507.1.

EXAMPLE 30

6-{6-[1-(3-Amino-benzo[a]isoxazol-5-yl)-7-fluoro-3-trifluoromethyl-1H-indazol-6-yl]-pyridin-3-yl}-3-methyl-2,3-dihydro-1H-pyrimidin-4-one

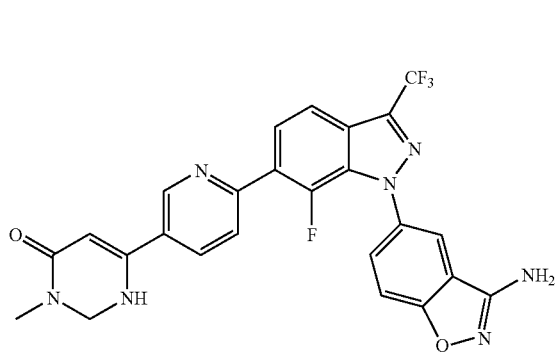

$^1$H-NMR (400 MHz, DDMSO-d$_6$) δ 3.35-3.42 (m, 5H), 6.60 (br s, 2H), 7.18 (br s, 1H), 7.68 (d, J=9.00 Hz, 1H), 7.88 (dd, J=7.75 Hz, 1.02 Hz, 1H), 7.98-8.06 (m, 3H), 8.25 (t, J=2.04 Hz, 1H), 8.53 (dd, J=6.12 Hz, 2.24 Hz, 1H), 8.61 (br s, 1H), 9.39 (dd, J=1.63 Hz, 0.82 Hz, 1H). Mass spectrum (LCMS, ESI pos.) calcd. for C$_{25}$H$_{17}$F$_4$N$_7$O$_2$: 524.4 (M+H). Found: 524.1.

EXAMPLE 31

(1-{4-[1-(3-Aminomethyl-phenyl)-7-fluoro-3-methyl-1H-indazol-6-yl]-3-fluoro-phenyl}-pyrrolidin-3-yl)-dimethyl-amine

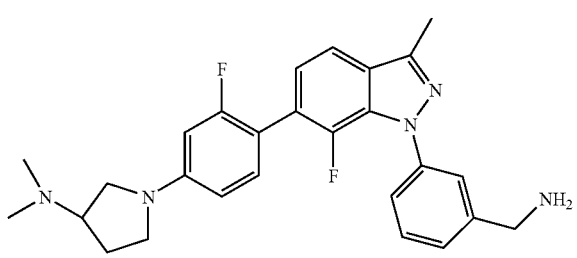

$^1$H-NMR (400 MHz, DDMSO-d$_6$) δ 7.67 (d, J =8.2 Hz, 1H), 7.58 (br s, 1H), 7.41 (m, 2H), 7.35 (d, J =6.9 Hz, 1H), 7.28 (m, 1H), 7.17 (dd, J=8.1 Hz, 5.5 Hz, 1H), 6.46 (m, 2H), 3.78 (s, 2H), 3.48 (dd, J=9.2 Hz, 7.6 Hz, 1H), 3.41 (m, 1H), 3.27 (m, 1H), 3.06 (t, J=8.7 Hz, 1H), 2.79 (m, 1H), 2.59 (s, 3H), 2.20 (s, 6H), 2.16 (m, 1H), 1.81 (m, 1H). Mass spectrum (LCMS, ESI pos.) calcd. for C$_{27}$H$_{30}$F$_2$N$_5$: 462.2 (M+H). Found: 462.1.

EXAMPLE 32

{4-[1-(3-Aminomethyl-phenyl)-7-fluoro-3-methyl-1H-indazol-6-yl]-3-fluoro-phenyl}-(1-methyl-1H-imidazol-2-ylmethyl)-pyridin-3-yl-amine

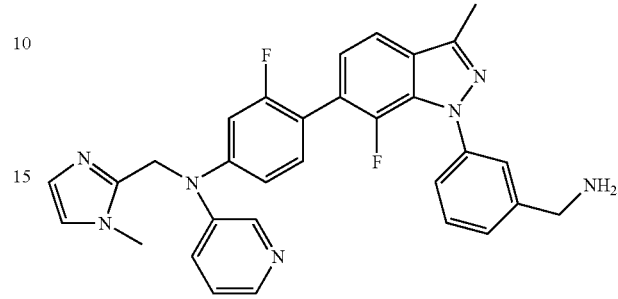

$^1$H-NMR (400 MHz, CDCl$_3$/CD$_3$OD) δ 8.36 (m, 1H), 8.29 (m, 1H), 7.86 (m, 1H), 7.54 (m, 7H), 7.18 (m, 1H), 6.86 (m, 3H), 4.97 (s, 2H), 3.94 (s, 2H), 3.61 (s, 3H), 2.66 (s, 3H). Mass spectrum (LCMS, ESI pos.) calcd. for C$_{31}$H$_{28}$F$_2$N$_7$: 536.2 (M+H). Found: 536.1.

EXAMPLE 33

1-{4-[1-(3-Aminomethyl-phenyl)-7-fluoro-3-methyl-1H-indazol-6-yl]-3-fluoro-phenyl}-piperazin-2-one

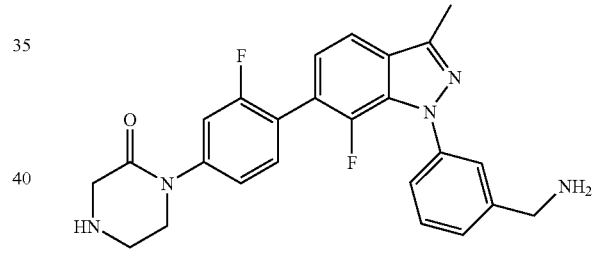

$^1$H-NMR (400 MHz, DMSO-d$_6$) δ 7.76 (m, 1H), 7.61 (m, 1H), 7.56 (t, J=8.3 Hz, 1H), 7.42 (m, 3H), 7.36 (m, 2H), 7.26 (m, 1H), 3.80 (s, 2H), 3.68 (t, J=5.0 Hz, 2H), 3.39 (m, 2H), 3.03 (t, J=5.2 Hz, 2H), 2.62 (s, 3H). Mass spectrum (LCMS, ESI pos.) calcd. for C$_{25}$H$_{24}$F$_2$N$_5$O: 448.2 (M+H). Found: 448.1.

EXAMPLE 34

3-{6-[4-(1,1-Dioxo-1λ$^6$-[1,2]thiazinan-2-yl)-phenyl]-7-fluoro-3-methyl-indazol-1-yl}-benzylamine

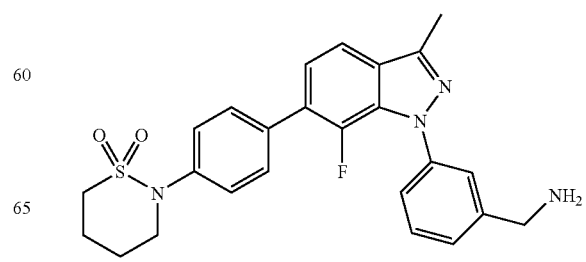

¹H-NMR (400 MHz, DMSO-d₆) δ 7.74 (d, J=8.3 Hz, 1H), 7.63 (m, 2H), 7.57 (br s, 1H), 7.43 (m, 3H), 7.37 (m, 2H), 3.79 (s, 2H), 3.70 (m, 2H), 2.60 (s, 3H), 2H), 1.83 (m, 2H), 1.27 (m, 2H). Mass spectrum (LCMS, ESI pos.) calcd. for $C_{25}H_{26}FN_4O_2S$: 487.2 (M+Na). Found: 487.7.

EXAMPLE 35

{4-[1-(3-Aminomethyl-phenyl)-7-fluoro-3-methyl-l1H-indazol-6-yl)]-3-fluoro-phenyl}-methyl-pyridin-4-yl-amine

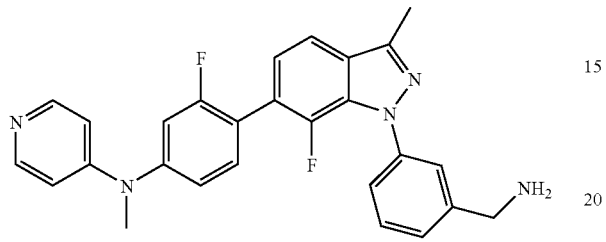

¹H-NMR (400 MHz, DMSO-d₆) δ 8.23 (d, J=5.7 Hz, 1H), 8.19 (m, 1H), 7.82 (m, 1H), 7.67 (m, 1H), 7.59 (m, 2H), 7.51 (m, 1H), 7.32 (m, 3H), 7.19 (m, 1H), 6.82 (m, 1H), 6.65 (m, 1H), 4.14 (s, 2H), 3.37 (s, 3H), 2.63 (s, 2H). Mass spectrum (LCMS, ESI pos.) calcd. for $C_{27}H_{24}F_2N_5$: 456.2 (M+H). Found: 456.2.

EXAMPLE 36

3-[7-Fluoro-6-(2-fluoro-4-pyridin-2-yl-phenyl)-3-methyl-indazol-1-yl]-benzylamine

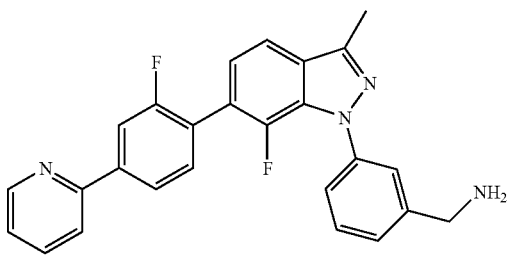

¹H-NMR (400 MHz, CDCl₃/CD₃OD) δ 8.70 (m, 1H), 7.85 (m, 4H), 7.60 (m, 5H), 7.45 (m, 1H), 7.29 (m, 1H), 4.06 (s, 2H), 2.71 (br s, 3H), 2.01 (s, 3H). Mass spectrum (LCMS, ESI pos.) calcd. for $C_{26}H_{21}F_2N_4$: 427.2 (M+H). Found: 427.0.

EXAMPLE 37

5-{6-[4-(2-Chloro-pyridin-3-yl)-2-fluoro-phenyl]-7-fluoro-3-trifluoromethyl-indazol-1-yl}-benzo[d]isoxazol-3-ylamine

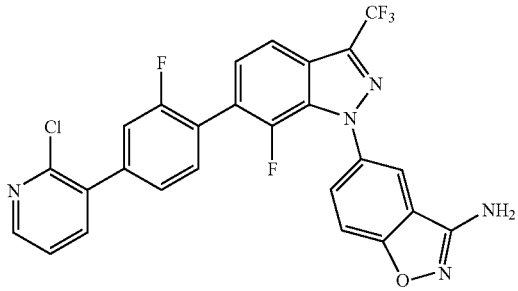

¹H-NMR (400 MHz, CDCl₃) δ 8.48 (dd, J=4.8 Hz, 2.0 Hz, 1H), 7.84 (m, 3H), 7.73 (dd, J=7.5 Hz, 2.0 Hz, 1H), 7.57 (m, 2H), 7.46 (m, 1H), 7.38 (m, 3H), 4.46 (s, 2H).

Mass spectrum (LCMS, ESI pos.) calcd. for $C_{26}H_{14}ClF_5N_5O$: 542.1 (M+H). Found: 542.2.

EXAMPLE 38

5-{7-Fluoro-6-[2-fluoro-4-(1-oxy-pyridin-2-yl)-phenyl]-3-trifluoromethyl-indazol-1-yl}-benzo[d]isoxazol-3-ylamine

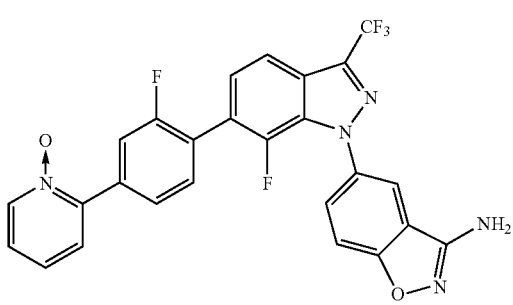

¹H-NMR (400 MHz, CDCl₃) δ 8.37 (dd, J=6.4 Hz, 1.0 Hz, 1H), 7.81 (m, 4H), 7.71 (dd, J=8.0 Hz, 1.7 Hz, 1H), 7.55 (m, 2H), 7.49 (dd, J=7.9 Hz, 2.0 Hz, 1H), 7.41 (dd, J=8.2 Hz, 5.4 Hz, 1H), 7.36 (td, J=7.7 Hz, 1.3 Hz, 1H), 7.30 (m, 1H), 4.49 (s, 2H). Mass spectrum (LCMS, ESI pos.) calcd. for $C_{26}H_{15}F_5N_5O_2$: 524.1 (M+H). Found: 524.1.

EXAMPLE 39

5-(7-Fluoro-6-{2-fluoro-4-[methyl-(1-methyl-pyrrolidin-3-yl)-amino]-phenyl}-3-trifluoromethyl-indazol-1-yl)-benzo[d]isoxazol-3-ylamine

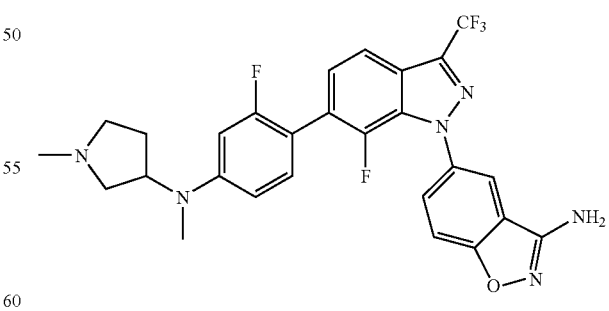

¹H-NMR (400 MHz, CDCl₃) δ 7.80 (m, 2H), 7.71 (dd, J=8.3 Hz, 1.2 Hz, 1H), 7.55 (d, J=9.5 Hz, 1H), 7.36 (m, 2H), 6.64 (m, 1H), 6.57 (m, 1H), 4.43 (s, 2H), 2.96 (s, 3H), 2.88 (m, 1H), 2.47 (m, 2H), 2.05 (m, 2H), 1.25 (m, 5H). Mass spectrum (LCMS, ESI pos.) calcd. for $C_{27}H_{24}F_5N_6O$: 543.2 (M+H). Found: 543.0.

EXAMPLE 40

1-{6-[1-(3-Amino-benzo[d]isoxazol-5-yl)-7-fluoro-3-trifluoromethyl-1H-indazol-6-yl]-pyridin-3-yl}-4-methyl-piperazin-2-one

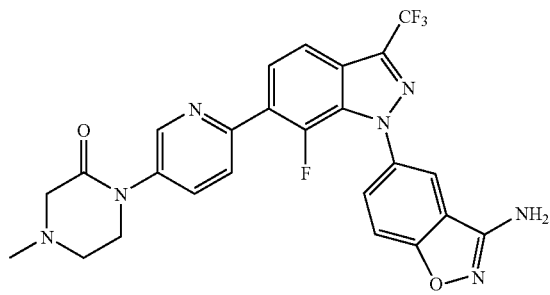

$^1$H-NMR (400 MHz, DMSO-d$_6$) δ 8.81 (s, 1H), 8.25 (s, 1H), 7.96 (m, 3H), 7.87 (d, J=8.2 Hz, 1H), 7.68 (d, J=8.9 Hz, 1H), 6.60 (s, 2H), 3.78 (m, 2H), 3.17 (m, 2H), 2.77 (m, 2H), 2.30 (s, 3H). Mass spectrum (LCMS, ESI pos.) calcd. for C$_{25}$H$_{20}$F$_4$N$_7$O$_2$: 526.2 (M+H). Found: 526.1.

EXAMPLE 41

1-(3-Amino-benzo[d]isoxazol-5-yl)-7-fluoro-6-[2-fluoro-4-(2-oxo-1,2-dihydro-pyridin-3-yl)-phenyl]-1H-indazole-3-carboxylic acid amide

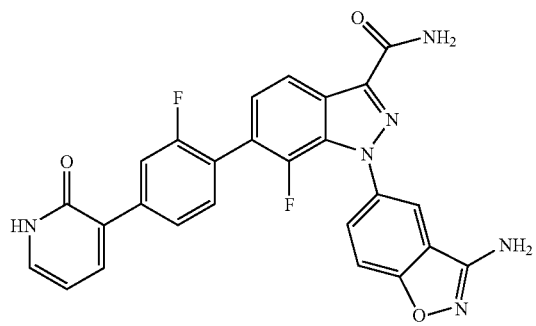

$^1$H-NMR (400 MHz, DMSO-d$_6$) δ 8.20 (m, 2H), 8.05 (m, 1H), 7.86 (m, 1H), 7.74 (m, 1H), 7.66 (m, 1H), 7.56 (m, 1H), 7.46 (m, 1H), 7.24 (s, 1H), 6.57 (m, 1H), 6.34 (m, 1H), 3.53 (m, 1H). Mass spectrum (LCMS, ESI pos.) calcd. for C$_{26}$H$_{17}$F$_2$N$_6$O$_3$: 499.1 (M+H). Found: 499.1.

EXAMPLE 42

1-{4-[1-(3-Amino-benzo[d]isoxazol-5-yl)-7-fluoro-3-trifluoromethyl-1H-indazol-6-yl]-3-fluoro-phenyl}-tetrahydro-pyrimidin-2-one

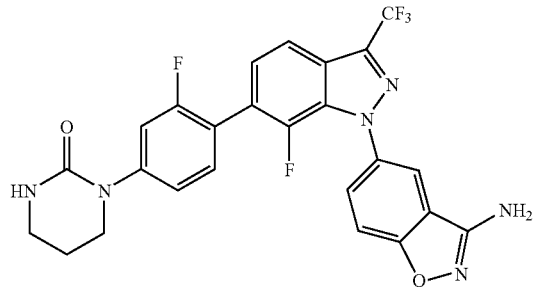

$^1$H-NMR (400 MHz, DMSO-d$_6$) δ 8.23 (s, 1H), 7.94 (m, 1H), 7.86 (d, J=8.4 Hz, 1H), 7.66 (d, J=8.8 Hz, 1H), 7.49 (m, 2H), 7.40 (dd, J=12.7 Hz, 2.0 Hz, 1H), 7.31 (dd, J=8.3 Hz, 2.0 Hz, 1H), 6.84 (s, 2H), 6.60 (m, 1H), 3.69 (m, 2H), 3.23 (m, 2H), 1.97 (m, 2H). Mass spectrum (LCMS, ESI pos.) calcd. for C$_{25}$H$_{18}$F$_5$N$_6$O$_2$: 529.1 (M+H). Found: 529.1.

EXAMPLE 43

1-(3-Amino-benzo[d]isoxazol-5-yl)-7-fluoro-6-[5-(3-oxo-morpholin-4-yl)-pyridin-2-yl]-1H-indazole-3-carboxylic acid amide; methanesulfonic acid salt

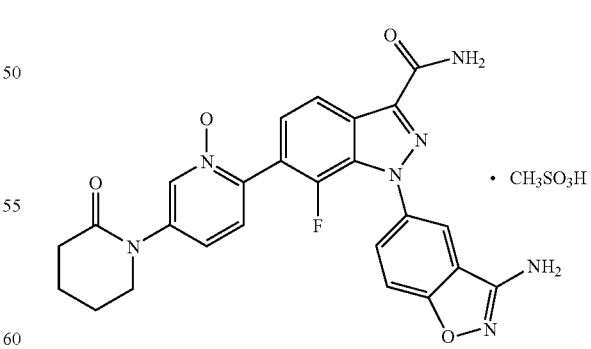

$^1$H-NMR (400 MHz, DMSO) δ 8.85 (d, J=2.5 Hz, 1H), 8.22-8.19 (m, 2H), 8.06 (br s, 1H), 8.02-7.86 (m, 4H), 7.69-7.66 (m, 2H), 4.27 (s, 2H), 4.03-4.01 (m, 2H), 3.87-3.85 (m, 2H), 2.32 (s, 3H). Mass spectrum (LCMS, ESI pos.) calcd. for C$_{24}$H$_{19}$FN$_7$O$_4$ (M+H): 488.1. Found: 488.2.

EXAMPLE 44

1-(3-amino-benzo[d]isoxazol-5-yl)-7-fluoro-6-(2-oxo-1'-oxy-3,4,5,6-tetrahydro-2H-[1,3!]bipyridinyl-6'-yl)-1H-indazole-3-carboxylic acid amide, methanesulfonic acid salt $^1$H-NMR (400 MHz, DMSO) δ 8.51 (d, J=1.4 Hz, 1H), 8.20-7.65 (m, 7H), 7.51-7.44 (m, 2H), 3.69 (t, J=5.9 Hz, 2H), 2.44 (t, J=6.5 Hz, 2H), 2.31 (s, 3H), 1.86-1.83 (m, 4H). Mass spectrum (LCMS, ESI pos.) calcd. for C$_{25}$H$_{21}$FN$_7$O$_4$ (M+H): 502.1. Found: 502.1.

EXAMPLE 45

1-(3-Amino-benzo[d]isoxazol-5-yl)-7-fluoro-6-[2-fluoro-4-(methyl-pyridin-2-yl-amino)-phenyl]-1H-indazole-3-carboxylic acid amide

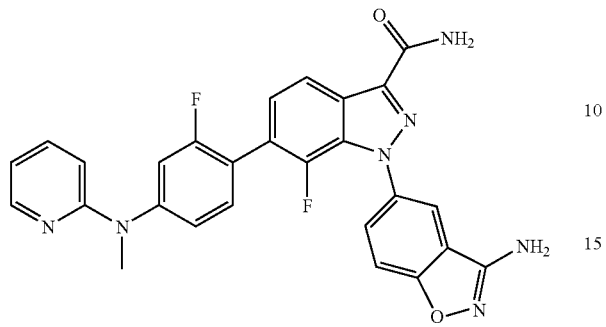

$^1$H-NMR (400 MHz, CDCl$_3$/drop of CD$_3$OD) δ 8.22-8.10 (m, 2H), 7.87-7.72 (m, 2H), 7.43-7.28 (m, 4H), 7.09-6.69 (m, 4H), 3.48 (s, 3H). Mass spectrum (LCMS, ESI pos.) calcd. for C$_{27}$H$_{20}$F$_2$N$_7$O$_4$ (M+H): 512.1. Found: 512.2.

EXAMPLE 46

1-[1-(3-Amino-benzo[d]isoxazol-5-yl)-7-fluoro-3-trifluoromethyl-1H-indazol-6-yl]-4-(2-oxo-1,2-dihydro-pyridin-3-yl)-piperazin-2-one; methanesulfonic acid salt

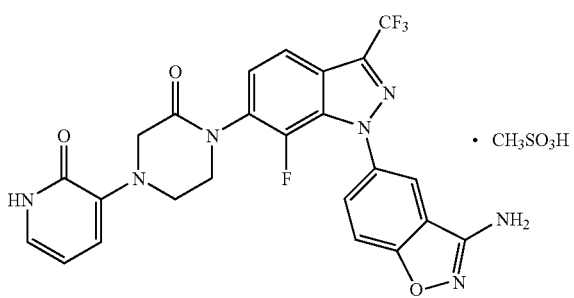

$^1$H-NMR (400 MHz, CDCl$_3$/drop of CD$_3$OD) δ 7.91-7.90 (m, 1H), 7.79-7.76 (m, 1H), 7.74-7.71 (m, 1H), 7.67-7.64 (m, 1H), 7.52-7.06 (m, 2H), 6.89 (d, J=7.4 Hz, 1H), 6.38-6.35 (m, 1), 3.90 (s, 2H), 3.82-3.80 (m, 2H), 3.71-3.68 (m, 2H), 2.82 (s, 3H).

Mass spectrum (LCMS, ESI pos.) calcd. for C$_{24}$H$_{18}$F$_4$N$_7$O$_3$ (M+H): 528.1. Found: 527.9.

EXAMPLE 47

1-{4-[1-(3-Aminobenzo[d]isoxazol-5-yl)-7-fluoro-3-trifluoromethyl-1H-indazol-6-yl]-3-fluorophenyl}-piperidin-2-one

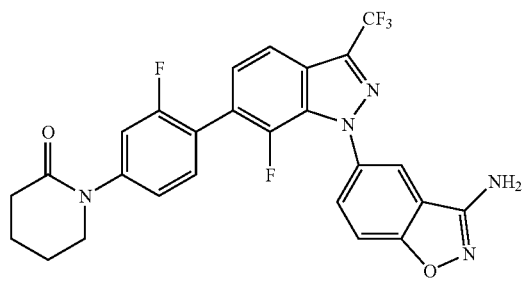

$^1$H-NMR (400 MHz, CDCl$_3$): 7.84 (t, J=2.2 Hz, 1H), 7.82-7.78 (m, 1H), 7.77 (dd, J=0.8, 8.6 Hz, 1H), 7.54 (d, J=8.9 Hz, 1H), 7.41 (t, J=8.3 Hz, 1H), 7.36 (dd, J=5.6, 8.4 Hz, 1H), 7.21-7.14 (m, 2H), 4.56 (br s, 2H), 3.69 (t, J=5.5 Hz, 2H), 2.59 (t, J=6.4 Hz, 2H), 2.04-1.94 (m, 4H). Mass Spectrum (LCMS, ESI, pos.) Calcd. for C$_{26}$H$_{19}$F$_5$N$_5$O$_2$: 528.15 (M+H). Found: 528.2.

EXAMPLE 48

1-{4-[1-(3-Amino-6-fluorobenzo[d]isoxazol-5-yl)-7-fluoro-3-methyl-1H-indazol-6-yl]-3-fluorophenyl}-piperidin-2-one

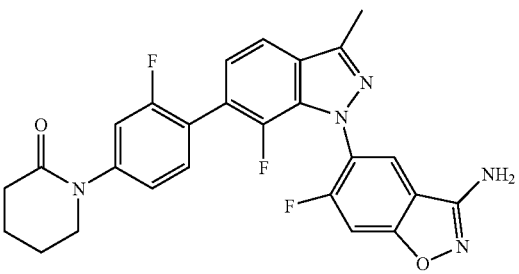

$^1$H-NMR (400 MHz, CDCl$_3$): 7.76 (d, J=6.9 Hz, 1H), 7.56 (d, J=8.3 Hz, 1H), 7.42 (t, J=8.3 Hz, 1H), 7.30 (d, J=9.2, Hz, 1H), 7.20 (dd, J=5.7, 7.8 Hz, 1H), 7.18-7.11 (m, 2H), 4.45 (br s, 2H), 3.68 (t, J=5.6 Hz, 2H), 2.67 (s, 3H), 2.59 (t, J=6.3 Hz, 2H), 2.01-1.91 (m, 4H). Mass Spectrum (LCMS, ESI, pos.) Calcd. for C$_{26}$H$_{21}$F$_3$N$_5$O$_2$: 492.16 (M+H). Found: 492.2.

EXAMPLE 49

1-{4-[1-(3-Amino-6-fluorobenzo[d]isoxazol-5-yl)-7-fluoro-3-trifluoro methyl-1H-indazol-6-yl]-3-fluorophenyl}-piperidin-2-one

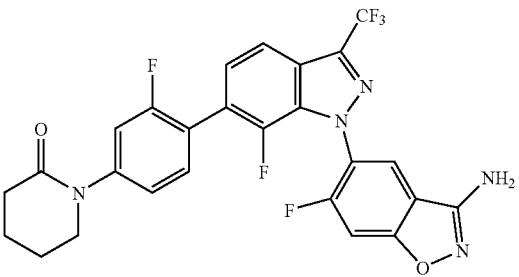

$^1$H-NMR (400 MHz, CDCl$_3$): 7.84 (d, J=6.8 Hz, 1H), 7.76 (dq, J=0.93, 8.5 Hz, 1H), 7.42 (t, J=8.0 Hz, 1H), 7.37 (ddd, J=0.6, 5.8, 8.5 Hz, 1H), 7.35 (d, J=9.1 Hz, 1H) 7.21-7.14 (m, 2H), 4.46 (br s, 2H), 3.69 (t, J=5.5 Hz, 2H), 2.59 (t, J=6.1 Hz, 2H), 2.01-1.89 (m, 4H). Mass Spectrum (LCMS, ESI, pos.) Calcd. for C$_{26}$H$_{18}$F$_6$N$_5$O$_2$: 546.14 (M+H).

Found: 546.2.

EXAMPLE 50

1-(4-[1-(3-Amino-6-methoxybenzo[d]isoxazol-5-yl)-7-fluoro-3-trifluoro methyl-1H-indazol-6-yl]-3-fluorophenyl}-piperidin-2-one

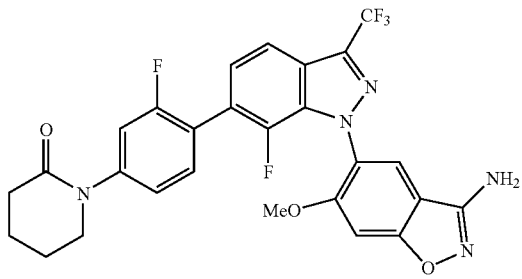

$^1$H-NMR (400 MHz, CDCl$_3$): 7.73 (d, J=8.8 Hz, 1H), 7.71 (s, 1H), 7.37 (t, J=8.3 Hz, 1H), 7.31 (dd, J=5.5, 8.3 Hz, 1H), 7.18-7.12 (m, 2H), 7.02 (s, 1H), 4.44 (br s, 2H), 3.83 (s, 3H), 3.68 (t, J=5.8 Hz, 2H), 2.59 (t, J=6.3 Hz, 2H), 2.02-1.91 (m, 4H). Mass Spectrum (LCMS, ESI, pos.) Calcd. for C$_{27}$H$_{21}$F$_5$N$_5$O$_3$: 558.16 (M+H). Found: 558.0.

EXAMPLE 51

1-(3-Aminobenzo[d]isoxazol-5-yl)-7-fluoro-6-[2-fluoro-4-(2-oxo-piperidin-1-yl)-phenyl]-1H-indazole-3-carboxamide

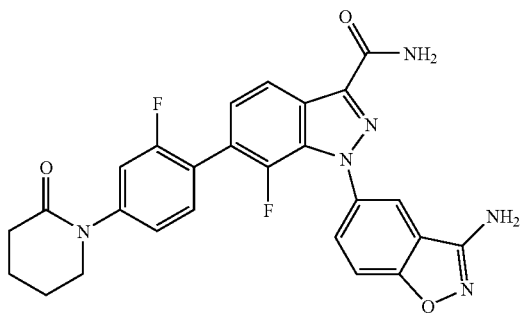

$^1$H-NMR (400 MHz, CDCl$_3$): 8.31 (d, J=8.4 Hz, 1H), 7.84-7.78 (m, 2H), 7.57 (d, J=8.8 Hz, 1H), 7.43 (t, J=8.3 Hz, 1H), 7.34 (dd, J=5.8, 8.4 Hz, 1H), 7.21-7.14 (m, 2H), 6.96 (br s, 1H), 5.55 (br s, 1H), 4.49. (br s, 2H), 3.69 (t, J=5.4 Hz, 2H), 2.59 (t, J=6.3 Hz, 2H), 2.02-1.92 (m, 4H). Mass Spectrum (LCMS, ESI, pos.) Calcd. for C$_{26}$H$_{21}$F$_2$N$_6$O$_3$: 503.16 (M+H). Found: 503.1.

EXAMPLE 52

1-{4-[1-(3-Amino-6-hydroxybenzo[d]isoxazol-5-yl)-7-fluoro-3-trifluoro methyl-1H-indazol-6-yl]-3-fluorophenyl}-piperidin-2-one

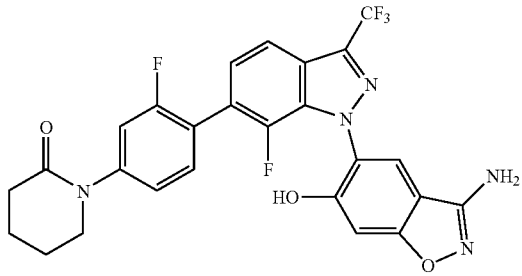

$^1$H-NMR (400 MHz, CDCl$_3$/d$_4$-MeOH): 7.70 (d, J=8.4 Hz, 1H), 7.58 (s, 1H), 7.45 (t, J=8.3 Hz, 1H), 7.29 (dd, J=5.6, 8.4 Hz, 1H), 7.15-6.95 (m, 2H), 6.75 (s, 1H), 3.69 (t, J=5.5 Hz, 2H), 2.57 (t, J=6.3 Hz, 2H), 2.03-1.93 (m, 4H). Mass Spectrum (LCMS, ESI, pos.) Calcd. for C$_{26}$H$_{19}$F$_5$N$_5$O$_3$: 544.14 (M+H). Found: 544.1.

EXAMPLE 53

1-(3-Aminobenzo[d]isoxazol-5-yl)-7-fluoro-6-[2-fluoro-4-(methyl-pyridin-4-yl-amino)-phenyl]-1H-indazole-3-carboxamide

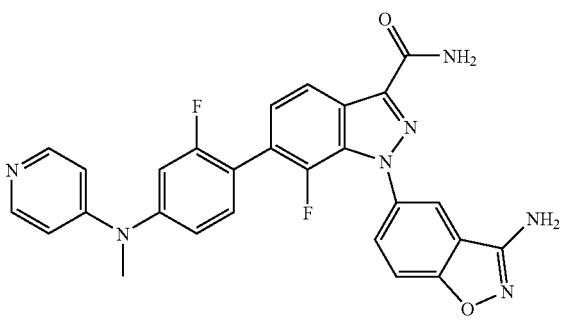

$^1$H-NMR (400 MHz, d$_6$-DMSO): 8.24-8.19 (m, 4H), 8.07 (br s, 1H), 7.94 (dt, J=2.2, 8.9 Hz, 1H), 7.69-7.65 (m, 2H), 7.60 (t, J=8.4 Hz, 1H), 7.44 (dd, J=5.6, 8.0 Hz, 1H), 7.34 (dd, J=2.1, 11.7 Hz, 1H), 7.26 (dd, J=2.2, 8.3 Hz, 1H), 6.83-6.80 (m, 2H), 6.59 (br s, 2H), 3.36 (s, 3H). Mass Spectrum (LCMS, ESI, pos.) Calcd. for C$_{27}$H$_{20}$F$_2$N$_7$O$_2$: 512.16 (M+H). Found: 512.2.

EXAMPLE 54

1-(3-Aminobenzo[d]isoxazol-5-yl)-7-fluoro-6-(2-oxo-3,4,5,6-tetrahydro-2H-[1,3']bipyridinyl-6'-yl)-1H-indazole-3-carboxamide

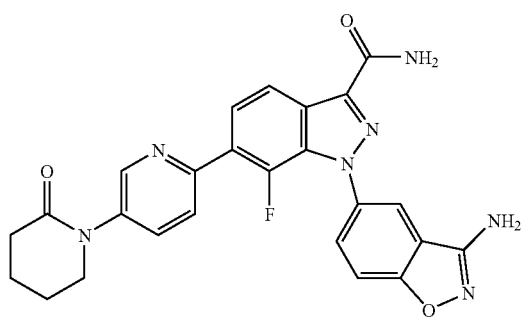

$^1$H-NMR (400 MHz, d$_6$-DDMSO): 8.72 (dd, J=0.8, 2.3 Hz, 1H), 8.22 (t, J=2.4 Hz, 1H), 8.20 (d, J=8.6 Hz, 1H), 8.06 (br s, 1H), 8.00 (dt, J=2.2, 8.9 Hz, 1H), 7.92-7.84 (m, 3H), 7.68 (d, J=8.7 Hz, 1H), 7.67 (br s, 1H), 6.60 (s, 2H), 3.71 (t, J=5.5 Hz, 2H), 2.45 (t, J=6.3 Hz, 2H), 1.94-1.83 (m, 4H). Mass Spectrum (LCMS, ESI, pos.) Calcd. for C$_{25}$H$_{21}$FN$_7$O$_3$: 486.17 (M+H). Found: 486.2.

EXAMPLE 55

1-(3-Amino-6-methoxybenzo[d]isoxazol-5-yl)-7-fluoro-6-[4-(2-oxo-piperidin-1-yl)-phenyl]-1H-indazole-3-carboxamide

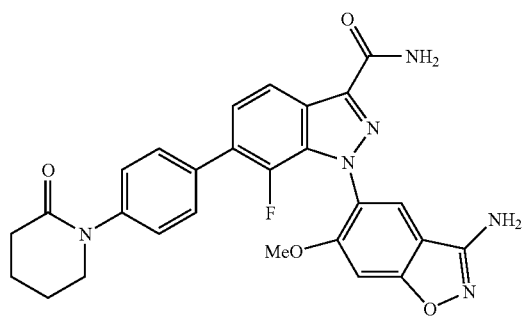

$^1$H-NMR (400 MHz, CDCl$_3$): 8.14 (d, J=8.4 Hz, 1H), 8.08 (s, 1H), 8.00 (br s, 1H), 7.59 (br s, 1H), 7.58 (d, J=8.6 Hz, 2H), 7.46 (dd, J=6.4, 8.4 Hz, 1H), 7.38 (d, J=8.7 Hz, 2H), 7.37 (s, 1H), 6.46 (s, 2H), 3.81 (s, 3H), 3.64 (t, J=5.4 Hz, 2H), 2.41 (t, J=6.3 Hz, 2H), 1.92-1.80 (m, 4H). Mass Spectrum (LCMS, ESI, pos.) Calcd. for C$_{27}$H$_{24}$FN$_6$O$_4$: 515.18 (M+H). Found: 515.1.

EXAMPLE 56

1-(3-Amino-6-methoxybenzo[d]isoxazol-5-yl)-7-fluoro-6-(2-oxo-3,4,5,6-tetrahydro-2H-[1,3']bipyridinyl-6'-yl)-1H-indazole-3-carboxamide

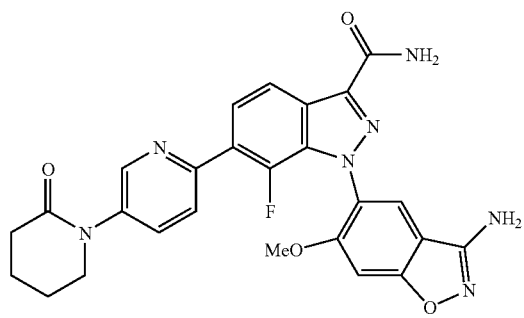

$^1$H-NMR (400 MHz, d$_6$-DDMSO): 8.71-8.69 (m, 1H), 8.16 (d, J=8.5 Hz, 1H), 8.10 (s, 1H), 8.02 (br s, 1H), 7.84 (dd, J=6.4, 8.5 Hz, 1H), 7.83-i.81 (m, 1H), 7.82 (br s, 1H), 7.61 (br s, 1H), 7.39 (s, 1H), 6.46 (s, 2H), 3.81 (s, 3H), 3.70 (t, J=5.5 Hz, 2H), 2.44 (t, J=6.4 Hz, 2H), 1.95-1.80 (m, 4H). Mass Spectrum (LCMS, ESI, pos.) Calcd. for C$_{26}$H$_{23}$FN$_7$O$_4$: 516.18 (M+H). Found: 516.1.

EXAMPLE 57

1-(3-Amino-6-methoxybenzo[d]isoxazol-5-yl)-7-fluoro-6-(2-oxo-2H-[1,3']bipyridinyl-6'-yl)-1H-indazole-3-carboxamide

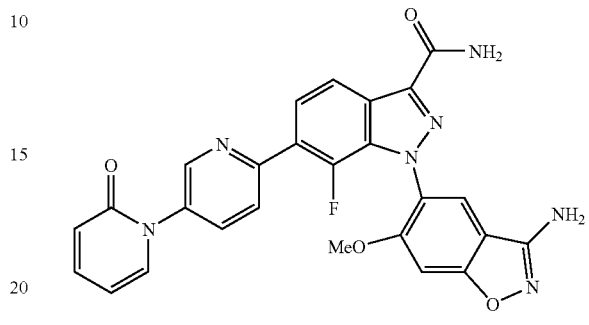

$^1$H-NMR (400 MHz, d$_6$-DDMSO): 8.81 (d, J=2.5 Hz, 1H), 8.20 (d, J=8.5 Hz, 1H), 8.12 (s, 1H), 8.03 (br s, 1H), 8.01 (dd, J=2.6, 8.6 Hz, 1H), 7.94 (dd, J=1.2, 8.4 Hz, 1H), 7.88 (dd, J=6.3, 8.4 Hz, 1H), 7.79 (dd, J=1.9, 6.9 Hz, 1H), 7.63 (br s, 1H), 7.56 (ddd, J=2.0, 6.6, 9.0 Hz, 1H), 7.39 (s, 1H), 6.54 (d, J=9.3 Hz, 1H), 6.47 (s, 2H), 6.39 (dt, J=1.1, 6.7 Hz, 1H), 3.82 (s, 3H). Mass Spectrum (LCMS, ESI, pos.) Calcd. for C$_{26}$H$_{19}$FN$_7$O$_4$: 512.15 (M+H). Found: 512.1.

EXAMPLE 58

1-(3-Amino-benzo[d]isoxazol-5-yl)-6-{4-[(2-dimethylamino-ethyl)-pyridin-4-yl-amino]-2-fluoro-phenyl}-7-fluoro-1H-indazole-3-carboxamide dimesylate salt

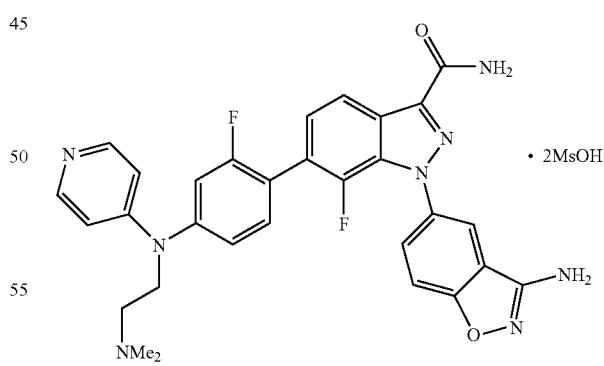

$^1$H-NMR (400 MHz, d$_4$-DMeOH): 8.27 (d, J=6.9 Hz, 2H), 8.28 (d, J=8.4 Hz, 1H), 8.11 (t, J=2.2 Hz, 1H), 7.89 (dt, J=2.3, 8.9 Hz, 1H), 7.79 (t, J=8.1 Hz, 1H), 7.59 (d, J=8.9 Hz, 1H), 7.49-7.38 (m, 3H), 7.09 (d, J=5.9 Hz, 2H), 4.36-4.29 (m, 2H), 3.40-3.34 (m, 2H), 2.84 (br s, 6H), 2.70 (s, 6H). Mass Spectrum (LCMS, ESI, pos.) Calcd. for C$_{30}$H$_{27}$F$_2$N$_8$O$_2$: 569.22 (M+H). Found: 569.1.

EXAMPLE 59

1-(3-Amino-benzo[d]isoxazol-5-yl)-6-{4-[(3-dimethylamino-propyl)-pyridin-4-yl-amino]-2-fluoro-phenyl}-7-fluoro-1H-indazole-3-carboxamide dimesylate salt

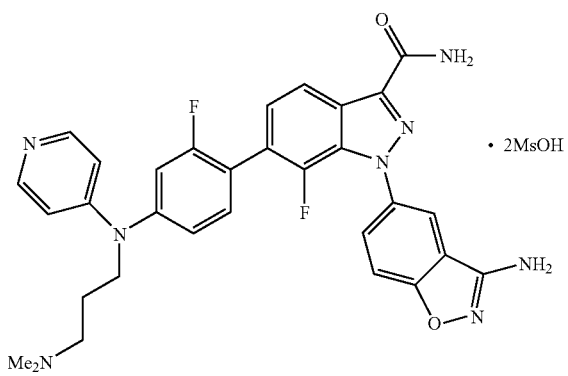

$^1$H-NMR (400 MHz, d$_4$-MeOH): 8.28 (d, J=8.4 Hz, 1H), 8.24 (d, J=7.3 Hz, 2H), 8.11 (t, J=2.2 Hz, 1H), 7.89 (dt, J=2.4, 8.9 Hz, 1H), 7.79 (t, J=8.1 Hz, 1H), 7.59 (d, J=8.9 Hz, 1H), 7.47 (dd, J=2.2, 10.0 Hz, 1H), 7.44-7.38 (m, 2H), 7.09 (br s, 2H), 4.09-4.03 (m, 2H), 3.27-3.21 (m, 2H), 2.90 (s, 6H), 2.70 (s, 6H), 2.23-2.13 (m, 2H). Mass Spectrum (LCMS, ESI, pos.) Calcd. for C$_{31}$H$_{29}$F$_2$N$_8$O$_2$: 583.24 (M+H). Found: 583.2.

EXAMPLE 60

1-(3-Amino-6-hydroxy-benzo[d]isoxazol-5-yl)-6-{4-[(3-dimethylamino-propyl)-pyridin-4-yl-amino]-2-fluoro-phenyl}-7-fluoro-1H-indazole-3-carbamide bis-(trifluoroacetate) salt

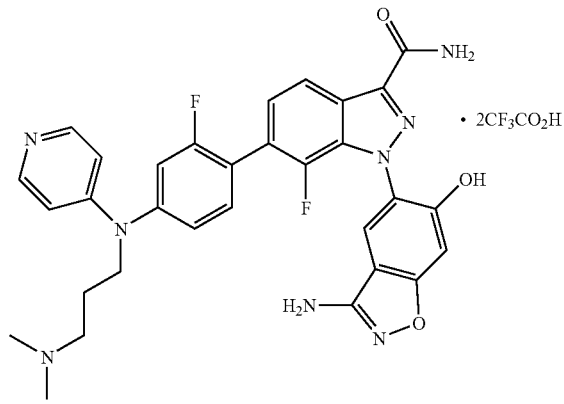

$^1$H-NMR (400 MHz, d$_4$-MeOH): 8.23 (d, J=8.4 Hz, 1H), 8.22 (d, J=7.4 Hz, 2H), 7.91 (s, 1H), 7.74 (t, J=8.1 Hz, 1H), 7.42 (dd, J=2.0, 10.2 Hz, 1H), 7.37 (d, J=8.3 Hz, 1H), 7.36 (dd, J=4.3, 8.2 Hz, 1H), 7.05 (br d, J=6.1 Hz, 1H), 6.94 (s, 1H), 4.07-4.01 (m, 2H), 3.25-3.20 (m, 2H), 2.88 (s, 6H), 2.22-2.13 (m, 2H). Mass Spectrum (LCMS, ESI, pos.) Calcd. for C$_{31}$H$_{29}$F$_2$N$_8$O$_3$: 599.23 (M+H). Found: 599.4.

EXAMPLE 61

1-(3-Amino-benzo[d]isoxazol-5-yl)-6-{4-[(2-dimethylamino-ethyl)-phenyl-amino]-2-fluoro-phenyl}-7-fluoro-1H-indazole-3-carboxamide mesylate salt

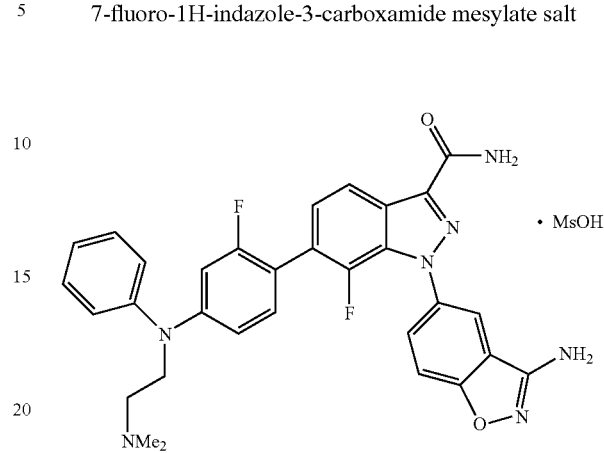

$^1$H-NMR (400 MHz, d$_6$-DDMSO): 9.48 (br s, 1H), 8.19 (br s, 1H), 8.17 (d, J=8.4 Hz, 1H), 8.03 (br s 1H), 7.91 (dt, J=2.1, 8.8 Hz, 1H), 7.66 (d, J=8.9 Hz, 1H), 7.64 (br s, 1H), 7.50-7.45 (m, 2H), 7.38-7.32 (m, 2H), 7.29 (d, J=7.8 Hz, 2H), 7.27 (t, J=7.8 Hz, 1H). 6.81 (dd, J=2.2, 13.3 Hz, 1H), 6.67 (dd, J=2.3, 8.6 Hz, 1H), 6.58 (br s, 2H), 4.12-4.05 (m, 2H), 3.37-3.31 (m, 2H), 2.85 (br s, 3H), 2.84 (br s, 3H), 2.30 (s, 3H).

Mass Spectrum (LCMS, ESI, pos.) Calcd. for C$_{31}$H$_{28}$F$_2$N$_7$O$_2$: 568.23 (M+H). Found: 568.1.

EXAMPLE 62

1-(3-Amino-benzo[d]isoxazol-5-yl)-6-{4-[(2-dimethylamino-ethyl)-pyridin-3-yl-amino]-2-fluoro-phenyl}-7-fluoro-1H-indazole-3-carboxamide dimesylate salt

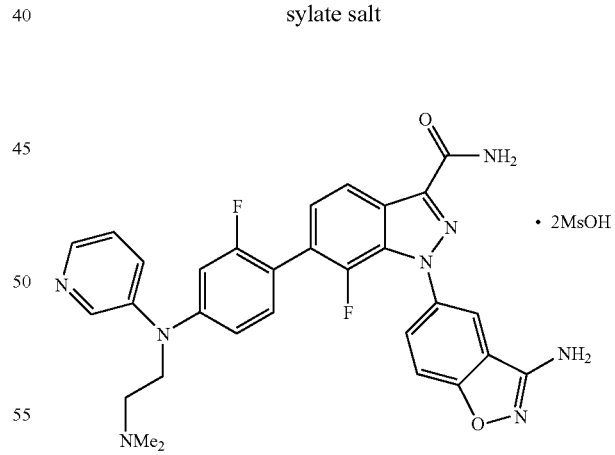

$^1$H-NMR (400 MHz, d$_6$-DDMSO): 9.64 (br s, 1H), 8.55 (d, J=2.0 Hz, 1H), 8.43 (d, J=4.8 Hz, 1H), 8.22 (d, J=8.3 Hz, 1H), 8.21 (br s, 1H), 8.06 (br s, 1H), 7.94-7.89 (m, 2H), 7.71 (dd, J=5.2, 8.4 Hz, 1H), 7.67 (d, J=8.7 Hz, 1H), 7.66 (br s, 1H), 7.56 (t, J=8.5 Hz, 1H), 7.39 (dd, J=6.0, 8.3 Hz, 1H), 7.23 (d, J=12.8 Hz, 1H), 7.07 (d, J=8.3 Hz, 1H), 6.58 (br s, 2H), 4.22-4.16 (m, 2H), 3.42-3.36 (m, 2H), 2.85 (br s, 3H), 2.84 (br s, 3H), 2.33 (s, 6H). Mass Spectrum (LCMS, ESI, pos.) Calcd. for C$_{30}$H$_{27}$F$_2$N$_8$O$_2$: 569.22 (M+H). Found: 569.2.

EXAMPLE 63

1-(3-Amino-benzo[d]isoxazol-5-yl)-6-{4-[(3-cyano-phenyl)-(2-dimethylamino-ethyl)-amino]-2-fluoro-phenyl}-7-fluoro-1H-indazole-3-carboxamide mesylate salt

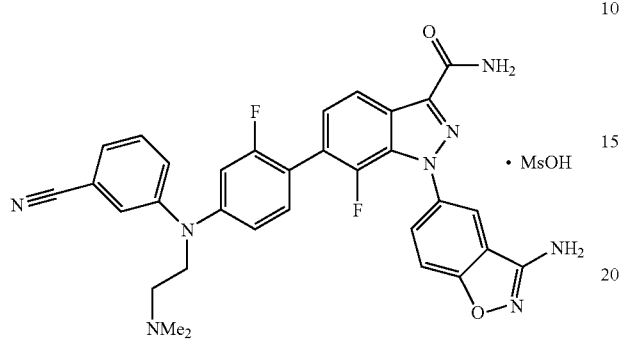

$^1$H-NMR (400 MHz, d$_6$-DDMSO): 9.41 (br s, 1H), 8.23-8.19 (m, 2H), 8.04 (br s, 1H), 7.92 (d, J=8.8 Hz, 1H), 7.66 (d, J=8.8 Hz, 2H), 7.66 (br s, 1H), 7.55 (d, J=5.1 Hz, 2H), 7.50-7.41 (m, 2H), 7.38 (dd, J=6.0, 7.9 Hz, 1H), 7.09 (dd, J=1.6, 12.6 Hz, 1H), 6.92 (dd, J=1.8, 8.5 Hz, 1H), 6.57 (br s, 2H), 4.17-4.09 (m, 2H), 3.36-3.30 (m, 2H), 2.85 (br s, 3H), 2.84 (br s, 3H), 2.29 (s, 3H). Mass Spectrum (LCMS, ESI, pos.) Calcd. for C$_{32}$H$_{27}$F$_2$N$_8$O$_2$: 593.22 (M+H). Found: 593.1.

EXAMPLE 64

1-(3-Amino-benzo[d]isoxazol-5-yl)-6-{4-[(3-carbamoyl-phenyl)-(2-dimethylamino-ethyl)-amino]-2-fluoro-phenyl}-7-fluoro-1H-indazole-3-carboxamide mesylate salt

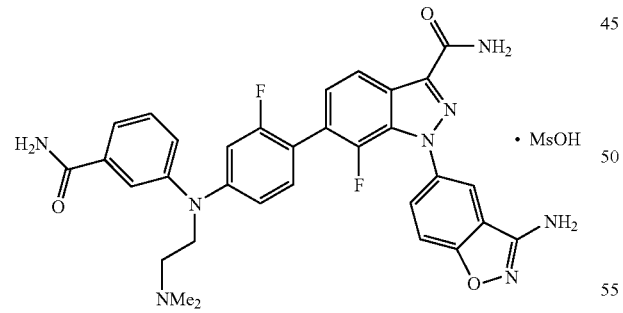

$^1$H-NMR (400 MHz, d$_6$-DDMSO): 9.45 (br s, 1H), 8.19 (br s, 1H), 8.17 (d, J=8.7 Hz, 1H), 8.02 (br s, 2H), 7.91 (d, J=9.0 Hz, 1H), 7.76-7.72 (m, 2H), 7.66 (d, J=9.0 Hz, 1H), 7.64 (br s, 1H), 7.54 (t, J=8.0 Hz, 1H), 7.48 (br s, 1H), 7.45-7.31 (m, 3H), 6.87 (d, J=13.4 Hz, 1H), 6.70 (d, J=9.5 Hz, 1H), 6.57 (br s, 2H), 4.15-4.08 (m, 2H), 3.38-3.32 (m, 2H), 2.85 (br s, 3H), 2.84 (br s, 3H), 2.29 (s, 3H). Mass Spectrum (LCMS, ESI, pos.) Calcd. for C$_{32}$H$_{29}$F$_2$N$_8$O$_3$: 611.23 (M+H). Found: 611.1.

EXAMPLE 65

1-(3-Amino-benzo[d]isoxazol-5-yl)-6-[4-(2-dimethylaminomethyl-pyridin-3-yl)-2-fluoro-phenyl]-7-fluoro-1H-indazole-3-carboxylic acid amide

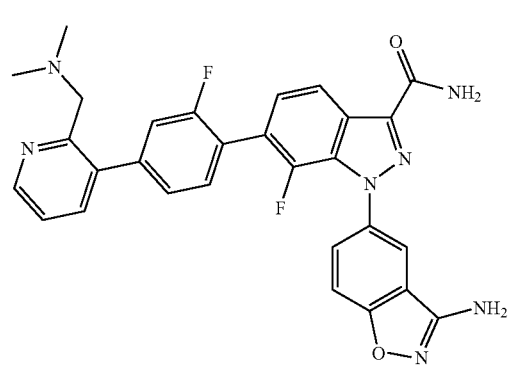

$^1$H-NMR (400 MHz, DDMSO-d$_6$) δ 8.59 (dt, J=4.75, 1.58 Hz), 8.25-8.20 (m, 2H), 8.07 (br s, 1H) 7.95 (dt, J=8.84, 1.71 Hz, 1H), 7.83 (dt J=7.76, 1.54 Hz, 1H), 7.74 (m, J=11.51 Hz, 1H), 7.69-7.64 (m, 3H), 7.56 (dt, J=7.94, 1.47 Hz, 1H), 7.50-7.44 (m, 2H), 6.59 (br s, 2H), 3.44 (s, 2H), 2.17 (s, 6H); Mass spectrum (LCMS, ESI pos.) calcd. for C$_{29}$H$_{23}$F$_2$N$_7$O$_2$: 540.2 (M+H). Found: 540.2.

EXAMPLE 66

1-(3-Amino-benzo[d]isoxazol-5-yl)-6-[4-(3-dimethylaminomethyl-pyridin-4-yl)-2-fluoro-phenyl]-7-fluoro-1H-indazole-3-carboxylic acid amide

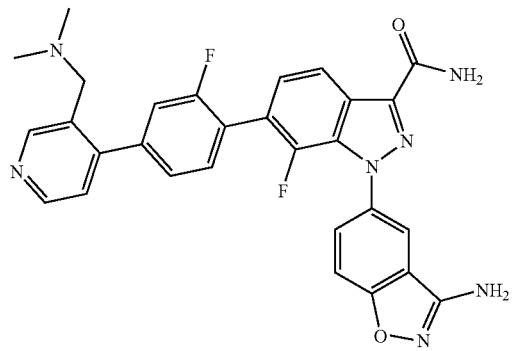

$^1$H-NMR (400 MHz, DDMSO-d6) δ 8.64 (br s, 1H), 8.56 (d; J=5.00 Hz, 1H), 8.24 (d, J=8.39 Hz, 1H), 8.22 (m, 1H), 8.07 (s, 1H), 7.95 (dt, J=8.92, 2.26 Hz), 7.72-7.66 (m, 4H), 7.53 (dd, J=1.52, 7.95 Hz, 2H), 7.48 (dd, J=5.81, 8.23 Hz, 1H), 7.41 (d, J=5.03 Hz, 1H), 6.59 (br s, 2H), 3.39 (s, 2H), 2.13 (s, 6H); Mass spectrum (LCMS, ESI pos.) calcd. for C$_{29}$H$_{23}$F$_2$N$_7$O$_2$: 540.2 (M+H). Found: 540.1.

EXAMPLE 67

1-(3-Amino-benzo[d]isoxazol-5-yl)-6-[4-(5-dimethylaminomethyl-1H-pyrazol-4-yl)-2-fluoro-phenyl]-7-fluoro-1H-indazole-3-carboxylic acid amide

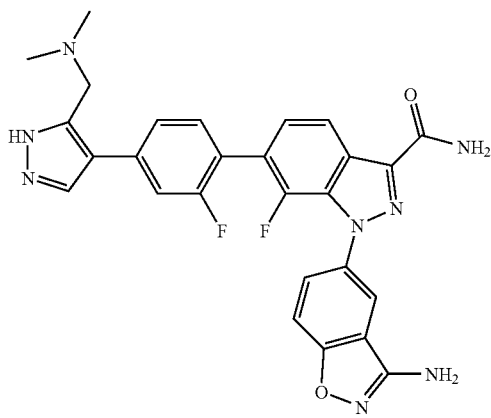

$^1$H-NMR (400 MHz, DMSO-d6) δ 8.23-8.20 (m, 2H), 8.06 (s, 1H), 7.93 (m, J=8.89 Hz, 1H), 7.68-7.66 (m, 3H), 7.59-7.53 (m, 2H), 7.44 (dd, J=6.29, 8.00 Hz, 1H), 7.29 (br s, 1H), 6.69 (br s, 1H), 6.59 (s, 2H), 3.35 (s, 2H), 1.76 (s, 6H); Mass spectrum (LCMS, ESI pos.) calcd. for $C_{27}H_{22}F_2N_8O_2$: 529.2 (M+H). Found: 529.1.

EXAMPLE 68

1-(3-Amino-benzo[d]isoxazol-5-yl)-6-[4-(3-dimethylaminomethyl-pyridin-2-yl)-2-fluoro-phenyl]-7-fluoro-1H-indazole-3-carboxylic acid amide

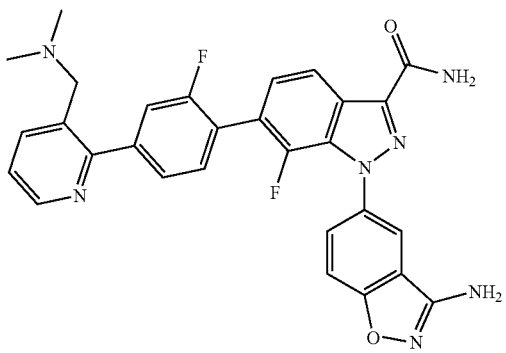

$^1$H-NMR (400 MHz, DMSO-d6) δ 8.59 (dd, J=1.6 Hz, J=4.7 Hz, 1H), 8.22 (d, J=8.4 Hz, 1H), 8.20 (t, J=1.9 Hz, 1H), 8.06 (br s, 1H), 7.93 (dt, J=8.75, 2.28 Hz, 1H), 7.89 (dd, J=1.53, 7.78 Hz, 1H), 7.75 (dd, J=10.55, 1.29 Hz, 1H), 7.66-7.61 (m, 4H), 7.47 (dd, J=5.83, 8.23 Hz, 1H), 7.42 (dd, J=4.71, 7.75 Hz, 1H), 6.57 (s, 2H), 3.40 (s, 2H), 2.13 (s, 6H); Mass spectrum (LCMS, ESI pos.) calcd. for $C_{29}H_{23}F_2N_7O_2$: 540.2 (M+H). Found: 540.1.

EXAMPLE 69

1-(3-Amino-benzo[d]isoxazol-5-yl)-6-[4-(4-dimethylaminomethyl-pyridin-3-yl)-2-fluoro-phenyl]-7-fluoro-1H-indazole-3-carboxylic acid amide

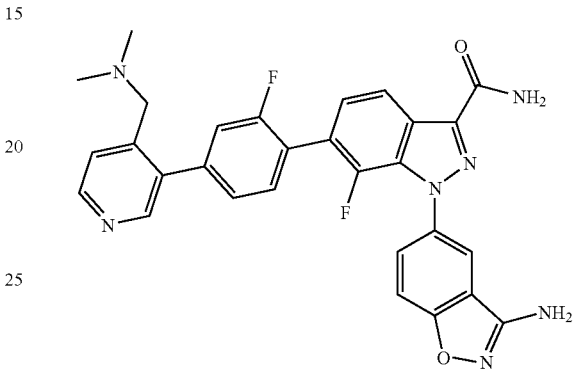

$^1$H-NMR (400 MHz, DMSO-d6) δ 8.57 (d, J=5.04 Hz, 1H), 8.49 (s, 1H), 8.22 (d, J=8.38 Hz, 1H), 8.20 (t, J=1.96 Hz, 1H), 8.06 (br s, 1H), 7.93 (dt, J=8.86, 2.28 Hz, 1H), 7.66-7.62 (m, 3H), 7.54 (m, 2H), 7.47 (dd, J=5.80, 8.23 Hz, 1H), 7.42 (dd, J=1.56, 7.91 Hz, 1H), 6.57 (s, 2H), 3.40 (s, 2H), 2.11 (s, 6H); Mass spectrum (LCMS, ESI pos.) calcd. for $C_{29}H_{23}F_2N_7O_2$: 540.2 (M+H). Found: 540.2.

EXAMPLE 70

1-{4-[1-(3-Amino-benzo[d]isoxazol-5-yl)-7-fluoro-3-hydroxymethyl-1H-indazol-6-yl]-3-fluoro-phenyl}-piperidin-2-one

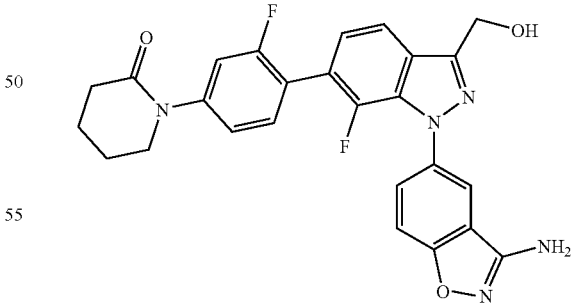

$^1$H-NMR (400 MHz, CDCl$_3$) δ 7.77-7.73 (m, 2H), 7.72 (d, J=8.34 Hz, 1H), 7.48 (d, J=8.67 Hz, 1H), 7.40 (t, J=8.27 Hz, 1H), 7.20 (dd, J=5.63, 8.19 Hz, 1H), 7.16 (dd, J=2.07, 5.87 Hz, 1H), 7.14 (dd, J=8.93, 1.93 Hz, 1H), 5.12 (s, 2H), 4.67 (s, 1H), 4.56 (s, 2H), 3.68 (t, J=5.53 Hz, 2H), 2.59 (t, J=6.28 Hz, 2H), 2.00-1.92 (m, 4H); Mass spectrum (LCMS, ESI pos.) calcd. for $C_{26}H_{21}F_2N_5O_3$: 490.2 (M+H). Found: 490.1.

EXAMPLE 71

1-(3-Amino-benzo[d]isoxazol-5-yl)-7-fluoro-6-[2-hydroxy-4-(2-oxo-piperidin-1-yl)-phenyl]-1H-indazole-3-carboxylic acid amide

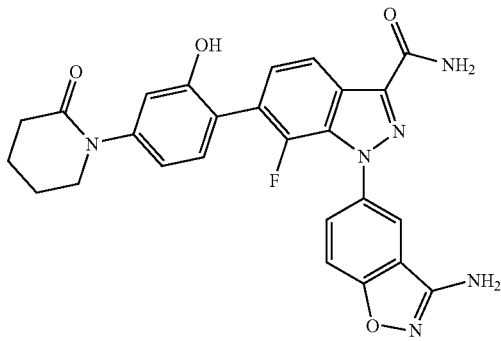

$^1$H-NMR (400 MHz, DMSO-d6) δ 9.78 (s, 1H), 8.18 (t, J=2.09 Hz, 1H), 8.12 (d, J=8.38 Hz, 1H), 8.02 (s, 1H), 7.90 (dt, J=9.20, 2.10 Hz, 1H), 7.65 (d, J=8.97 Hz, 1H), 7.63 (s, 1H), 7.35 (dd, J=5.76, 8.31 Hz, 1H), 7.26 (d, J=8.25 Hz, 1H), 6.87 (d, J=1.98 Hz, 1H), 6.81 (dd, J=2.00, 8.11 Hz, 1H), 6.58 (s, 2H), 3.60 (t, J=5.41 Hz, 2H), 2.40 (t, J=6.02 Hz), 1.85 (m, 4H); Mass spectrum (LCMS, ESI pos.) calcd. for $C_{26}H_{21}FN_6O_4$: 501.2 (M+H). Found: 501.1.

EXAMPLE 72

1-(3-Amino-benzo[d]isoxazol-5-yl)-6-[4-(2-dimethylaminomethyl-imidazol-1-yl)-2-fluoro-phenyl]-7-fluoro-1H-indazole-3-carboxylic acid amide

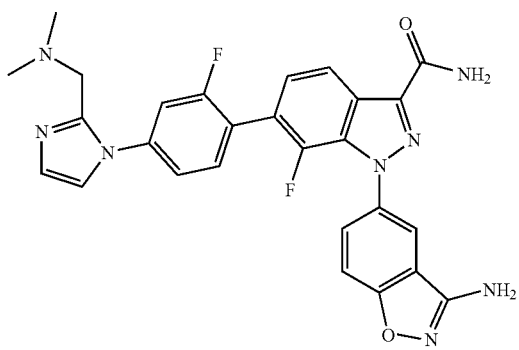

$^1$H-NMR (400 MHz, CD$_3$OD) δ 8.28 (d, J=8.40 Hz, 1H), 8.13 (t, J=2.28 Hz, 1H), 7.91 (dt, J=8.89, 2.32 Hz, 1H), 7.74 (dd, J=2.00, 10.78 Hz, 1H), 7.69 (t, J=8.06 Hz, 1H), 7.60 (d, J=8.79 Hz, 1H), 7.57 (td, J=6.44, 1.97 Hz, 1H), 7.44 (dd, J=8.15, 5.46 Hz, 1H), 4.23 (s, 1H), 3.52 (s, 2H), 2.25 (s, 6H); Mass spectrum (LCMS, ESI pos.) calcd. for $C_{27}H_{22}F_2N_8O_2$: 529.2 (M+H). Found: 529.1.

EXAMPLE 73

1-(3-Amino-benzo[d]isoxazol-5-yl)-7-fluoro-6-[2-methoxy-4-(2-oxo-piperidin-1-yl)-phenyl]-1H-indazole-3-carboxylic acid amide

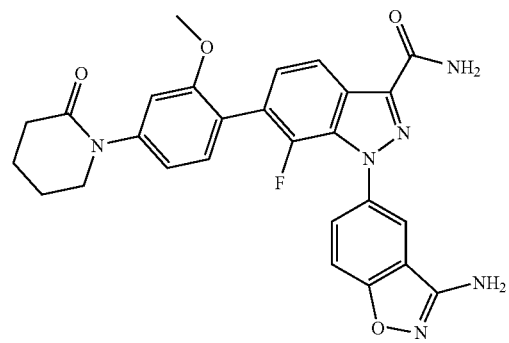

$^1$H-NMR (400 MHz, DMSO-d6) δ 8.17 (t, J=2.22 Hz, 1H), 8.13 (d, J=8.35 Hz, 1H), 8.02 (br s, 1H), 7.91 (dt, J=8.84, 2.28 Hz, 1H), 7.65 (d, J=8.94 Hz, 1H), 7.60 (s, 1H), 7.32 (dt, J=8.36, 2.93 Hz, 2H), 7.07 (d, J=1.78 Hz, 1H), 6.96 (dd, J=1.82, 8.07 Hz, 1H), 6.58 (s, 2H), 3.66 (t, J=5.58 Hz, 2H), 2.41 (t, J=6.35 Hz, 2H), 1.86 (m, 4H); Mass spectrum (LCMS, ESI pos.) calcd. for $C_{27}H_{23}FN_6O_4$: 515.2 (M+H). Found: 515.1.

EXAMPLE 74

1-(3-Amino-benzo[d]isoxazol-5-yl)-7-fluoro-6-[4-(2-oxo-2H-pyridin-1-yl)-phenyl]-1H-indazole-3-carboxylic acid amide

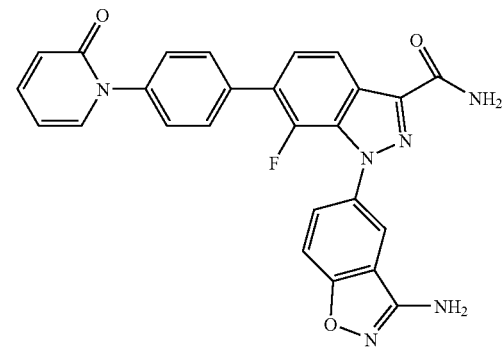

$^1$H-NMR (400 MHz, DMSO-d6) δ 8.22 (d, J=8.31 Hz, 1H), 8.22 (m, 1H), 8.06 (br s, 1H), 7.99 (dt, J=8.85, 2.09 Hz, 1H), 7.77 (d, J=7.85 Hz, 2H), 7.72 (dd, J=1.73, 6.89 Hz, 1H), 7.67 (d, J=8.73 Hz, 1H), 7.66 (s, 1H), 7.57-7.51 (m, 4H), 6.60 (s, 2H), 6.51 (d, J=9.13 Hz, 1H), 6.35 (td, J=6.75, 1.11 Hz, 1H) ; Mass spectrum (LCMS, ESI pos.) calcd. for $C_{26}H_{17}FN_6O_3$: 481.1 (M+H). Found: 481.2.

EXAMPLE 75

3-{7-Fluoro-6-[2-fluoro-4-(2-oxo-piperidin-1-yl)-phenyl]-3-methyl-indazol-1-yl}-benzamidine

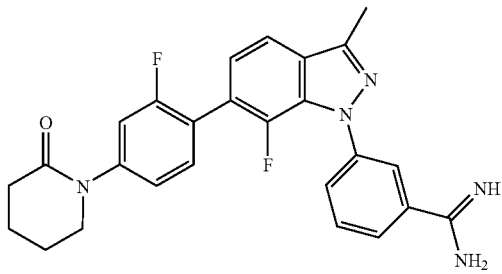

$^1$H-NMR (400 MHz, CD$_3$OD) δ 8.10 (m, J=1.77 Hz, 1H), 7.98 (m, J=7.47 Hz, 1H), 7.84 (dt, J=7.99, 1.00 Hz, 1H), 7.77 (d, J=7.91 Hz, 1H), 7.75 (d, J=8.25 Hz, 1H), 7.56 (t, J=8.28 Hz, 1H), 7.31 (dd, J=4.62, 7.20 Hz, 1H), 7.29 (s, 1H), 7.28 (d, J=10.47 Hz, 1H), 3.77 (t, J=5.58 Hz, 2H), 2.70 (s, 3H), 2.57 (t, J=6.33 Hz, 2H), 2.01 (m, 4H); Mass spectrum (LCMS, ESI pos.) calcd. for C$_{26}$H$_{23}$F$_2$N$_5$O: 460.2 (M+H). Found: 460.2.

EXAMPLE 76

3-(7-Fluoro-6-[4-(2-methanesulfonyl-phenyl)-piperazin-1-yl]-3-methyl-indazol-1-yl}-benzylamine

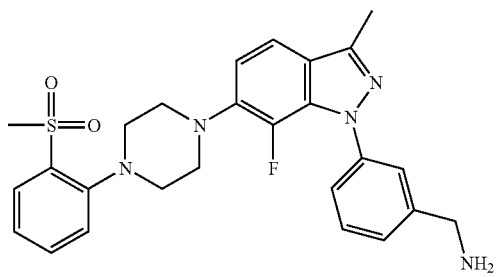

$^1$H-NMR (400 MHz, CDCl$_3$) δ 8.12 (dd, J=1.49, 7.93 Hz, 1H), 7.67 (ddd, J=1.53, 7.84, 7.81 Hz, 1H), 7.59 (s, 1H), 7.49-7.34 (m, 6H), 7.02 (dd, J=6.75, 8.51 Hz, 1H), 4.00 (s, 2H), 3.40 (s, 3H), 3.37 (br s, 1H), 2.61 (s, 3H), 2.27 (br s, 4H); Mass spectrum (LCMS, ESI pos.) calcd. for C$_{26}$H$_{28}$FN$_5$O$_2$S: 494.2 (M+H). Found: 494.1.

EXAMPLE 77

3-{7-Fluoro-6-[2-fluoro-4-(2-oxo-piperidin-1-yl)-phenyl]-3-methyl-indazol-1-yl}-benzamide

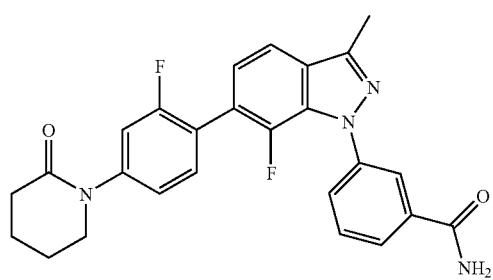

$^1$H-NMR (400 MHz, CDCl$_3$) δ 8.04 (dt, J=3.28, 1.72 Hz, 1H), 7.85 (dt, J=7.74, 1.07 Hz, 1H), 7.81 (m, J=8.03, Hz, 1H), 7.58 (d, J=6.88 Hz, 1H), 7.56 (d, J=8.20 Hz, 1H), 7.45 (t, J=8.28 Hz, 1H), 7.21 (dd, J=4.83, 7.44 Hz, 1H), 7.19 (d, J=6.03 Hz, 1H), 7.17 (dd, J=11.07, 1.99 Hz, 1H), 6.34 (br s, 1H), 5.82 (br s, 1H), 3.71 (t, J=5.54 Hz, 2H), 2.68 (s, 3H), 2.61 (t, J=6.29 Hz, 2H), 1.99 (m, 4H); Mass spectrum (LCMS, ESI pos.) calcd. for C$_{26}$H$_{22}$F$_2$N$_4$O$_2$: 461.2 (M+H). Found: 461.1.

EXAMPLE 78

6'-[1-(3-Amino-benzo[d]isoxazol-5-yl)-7-fluoro-3-methyl-1H-indazol-6-yl]-3,4,5,6-tetrahydro-[1,3']bipyridinyl-2-one

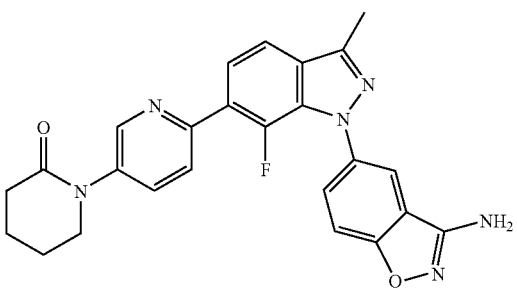

$^1$H-NMR (400 MHz, CDCl$_3$) δ 8.68 (d, J=2.04 Hz, 1H), 7.79-7.74 (m, 3H), 7.73-7.68 (m, 2H), 7.57 (d, J=8.38 Hz, 1H), 7.50 (d, J=8.82 Hz, 1H), 4.53 (s, 2H), 3.72 (t, J=5.46 Hz, 2H), 2.66 (s, 3H), 2.60 (t, J=6.29 Hz, 2H), 1.99 (m, 4H); Mass spectrum (LCMS, ESI pos.) calcd. for C$_{25}$H$_{21}$FN$_6$O$_2$: 457.2 (M+H). Found: 457.2.

EXAMPLE 79

1-{4-[1-(3-Amino-benzo[d]isoxazol-5-yl)-7-fluoro-3-methyl-1H-indazol-6-yl]-3-fluoro-phenyl}-azepan-2-one

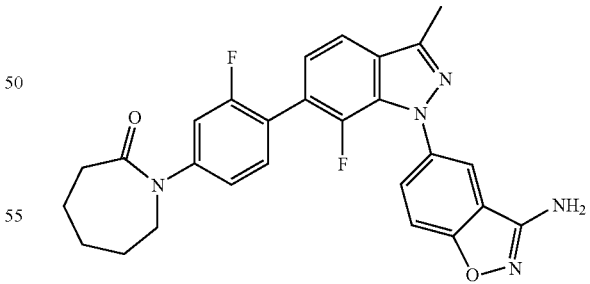

$^1$H-NMR (400 MHz, CDCl$_3$) δ 7.79 (dt, J=8.70, 2.53 Hz, 1H), 7.77 (m, 1H), 7.57 (d, J=8.18 Hz, 1H), 7.51 (d, J=8.79 Hz, 1H), 7.42 (t, J=8.28 Hz, 1H), 7.20 (dd, J=5.54, 8.15 Hz, 1H), 7.13 (dd, J=5.44, 2.13 Hz, 1H), 7.11 (d, J=1.72, 9.08 Hz, 1H), 4.55 (s, 2H), 3.81 (br s, 2H), 2.73 (m, 2H), 2.69 (s, 3H), 1.85 (br s, 6H); Mass spectrum (LCMS, ESI pos.) calcd. for C$_{27}$H$_{23}$F$_2$N$_5$O$_2$: 488.2 (M+H). Found: 488.2.

EXAMPLE 80

1-{4-[1-(3-Amino-benzo[d]isoxazol-5-yl)-7-fluoro-3-methyl-1H-indazol-6-yl]-3-fluoro-phenyl}-piperidin-2-one

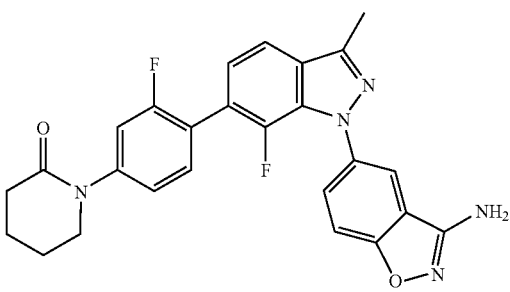

$^1$H-NMR (400 MHz, CDCl$_3$) δ 7.81 (ddd, J=2.36, 2.96, 8.92 Hz, 1H), 7.56 (t, J=2.1 Hz, 1H), 7.59 (d, J=8.24 Hz, 1H), 7.53 (d, J=8.88 Hz, 1H), 7.46 (t, J=8.27 Hz, 1H), 7.21 (ddd, J=5.44, 5.67, 7.79 Hz, 1H), 7.19 (s, 1H), 7.18 (dd, J=1.94, 9.34 Hz, 1H), 4.43 (s, 2H), 3.72 (t, J=5.35 Hz, 2H), 2.70 (s, 3H), 2.62 (t, J=6.22 Hz, 2H), 2.00 (m, 4H); Mass spectrum (LCMS, ESI pos.) calcd. for C$_{26}$H$_{21}$F$_2$N$_5$O$_2$: 474.2 (M+H). Found: 474.2.

EXAMPLE 81

5-[7-Fluoro-6-(3-fluoro-2'-methanesulfonyl-biphenyl-4-yl)-3-methyl-indazol-1-yl]-benzo[d]isoxazol-3-ylamine

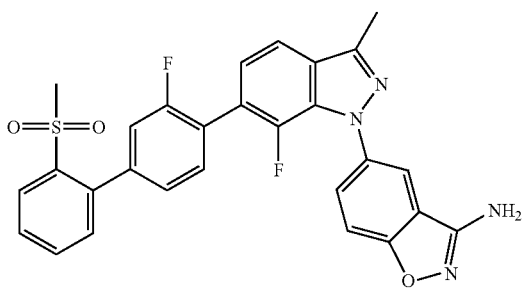

$^1$H-NMR (400 MHz, CDCl$_3$) δ 8.26 (dd, J=1.21, 7.92 Hz, 1H), 7.81 (ddd, J=2.17, 3.12, 8.89 Hz, 1H), 7.77 (t, J=2.20 Hz, 1H), 7.70 (td, J=7.50, 1.38 Hz, 1H), 7.65-7.59 (m, 2H), 7.54-7.50 (m, 2H), 7.42 (dd, J=1.36, 7.40 Hz, 1H), 7.38 (dd, J=1.73, 7.91 Hz, 1H), 7.32 (dd, J=1.64, 10.40 Hz, 1H), 7.28 (d, J=5.94 Hz, 1H), 4.42 (s, 2H), 2.78 (s, 3H), 2.70 (s, 3H); Mass spectrum (LCMS, ESI pos.) calcd. for C$_{28}$H$_{20}$F$_2$N$_4$O$_3$S 531.1 (M+H). Found: 531.1.

EXAMPLE 82

3-[7-Fluoro-6-(3-fluoro-2'-methanesulfonyl-biphenyl-4-yl)-3-methyl-indazol-1-yl]-benzylamine

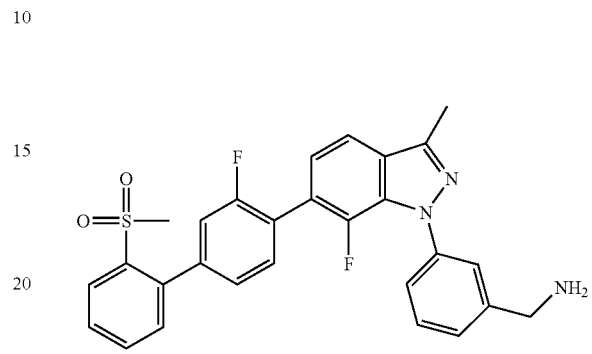

$^1$H-NMR (400 MHz, CDCl$_3$) δ 8.26 (dd, J=1.30, 7.92 Hz, 1H), 7.69 (td, J=7.50, 1.40 Hz, 1H), 7.61 (dt, J=7.69, 1.38 Hz, 1H), 7.61 (br s, 1H), 7.57 (d, J=8.21 Hz, 1H), 7.52 (t, J=7.69 Hz, 1H), 7.49 (m, 1H), 7.45 (d, J=7.58 Hz, 1H), 7.41 (dd, J=1.27, 7.45 Hz, 1H), 7.37 (dd, J=1.64, 7.85 Hz, 1H), 7.34 (m, 1H), 7.31 (dd, J=1.61, 10.41 Hz, 1H), 7.24 (dd, J=5.65, 7.80 Hz, 1H), 3.98 (s, 2H), 2.77 (s, 3H), 2.66 (s, 3H). Mass spectrum (LCMS, ESI pos.) calcd. for C$_{28}$H$_{23}$F$_2$N$_3$O$_2$S: 504.2 (M+H). Found: 504.0.

EXAMPLE 83

3-[7-Fluoro-6-(2'-methanesulfonyl-biphenyl-4-yl)-3-methyl-indazol-1-yl]-benzylamine

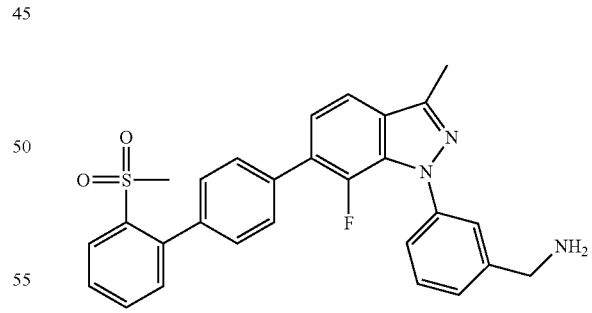

$^1$H-NMR (400 MHz, CDCl$_3$) δ 8.26 (dd, J=1.33, 7.93 Hz, 1H), 7.70-7.66 (m, 3H), 7.61-7.56 (m, 4H), 7.57 (d, J=8.20 Hz, 1H), 7.50 (m, J=7.90 Hz, 1H), 7.46 (d, J=7.43 Hz, 1H), 7.43 (dd, J=1.38, 7.51 Hz, 1H), 7.34 (m, J=7.23 Hz, 1H), 7.32 (dd, J=5.90, 8.20 Hz, 1H), 3.97 (s, 2H), 2.71 (s, 3H), 2.68 (s, 3H); Mass spectrum (LCMS, ESI pos.) calcd. for C$_{28}$H$_{24}$FN$_3$O$_2$S: 486.2 (M+H). Found: 486.0

EXAMPLE 84

3-{6-[4-(2-Dimethylaminomethyl-imidazol-1-yl)-phenyl]-7-fluoro-3-methyl-indazol-1-yl}-benzylamine

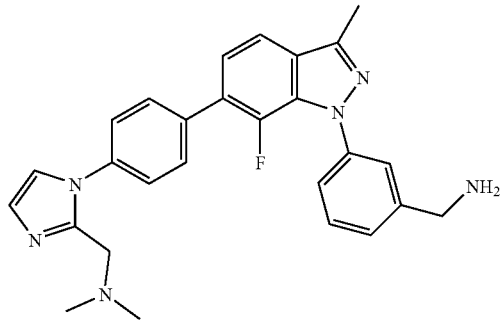

$^1$H-NMR (400 MHz, CDCl$_3$) δ 7.69 (d, J=8.58 Hz, 2H), 7.64 (d, J=8.61 Hz, 2H), 7.60 (br s, 1H), 7.57 (d, J=8.26 Hz, 1H), 7.49 (m, J=7.97 Hz, 1H), 7.45 (t, J=7.62 Hz, 2H), 7.35 (m, J=7.31 Hz, 1H), 7.28 (dd, J=5.94, 8.24 Hz, 1H), 7.13 (dd, J=1.22, 6.76 Hz, 1H), 3.98 (s, 2H), 3.46 (s, 2H), 2.67 (s, 3H), 2.29 (s, 6H); Mass spectrum (LCMS, ESI pos.) calcd. for C$_{27}$H$_{27}$FN$_6$: 455.2 (M+H). Found: 455.0.

EXAMPLE 85

4'-[1-(3-Aminomethyl-phenyl)-7-fluoro-3-methyl-1H-indazol-6-yl]-biphenyl-2-sulfonic acid amide

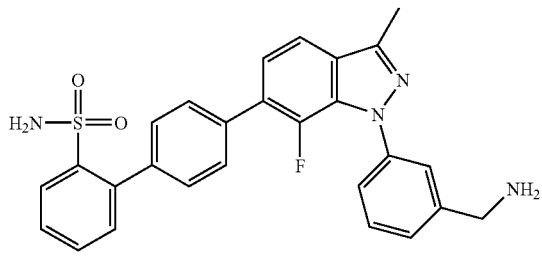

$^1$H-NMR (400 MHz, CDCl$_3$) δ 8.16 (dd, J=8.00, 0.67 Hz), 7.66-7.48 (m, 9H), 7.42 (t, J=7.60 Hz, 1H), 7.37 (dd, J=0.60, 7.48 Hz, 1H), 7.34 (d, J=7.57 Hz, 1H), 7.26 (dd, J=8.35, 5.92 Hz, 1H), 5.61 (br s, 1H), 5.48 (br s, 1H), 3.97 (s, 2H), 2.64 (s, 3H); Mass spectrum (LCMS, ESI pos.) calcd. for C$_{25}$H$_{21}$FN$_6$O$_2$: 457.2 (M+H). Found: 457.2.

EXAMPLE 86

1-{4-[1-(3-Amino-benzo[d]isoxazol-5-yl)-7-fluoro-3-methyl-1H-indazol-6-yl]-phenyl}-piperidin-2-one

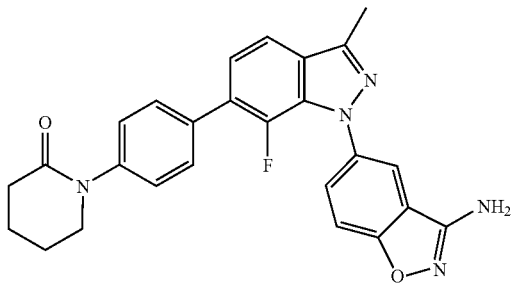

$^1$H-NMR (400 MHz, CDCl$_3$) δ 7.78 (ddd, J=2.18, 3.00, 8.80 Hz, 1H), 7.59 (dd, J=1.37, 8.38 Hz, 2H), 7.55 (d, J=8.27 Hz, 1H), 7.50 (d, J=8.83 Hz, 1H), 7.34 (m, J=8.53 Hz, 2H), 7.26 (dd, J=8.23, 6.02 Hz, 1H), 4.50 (s, 2H), 3.69 (t, J=5.66 Hz, 2H), 2.67 (s, 3H), 2.58 (t, J=6.22 Hz, 2H), 1.96 (m, 4H); Mass spectrum (LCMS, ESI pos.) calcd. for C$_{26}$H$_{22}$FN$_5$O$_2$: 456.2 (M+H). Found: 456.2.

EXAMPLE 87

3-[3-Methyl-6-(5-pyridin-2-yl-thiophen-2-yl)-indazol-1-yl]-benzylamine

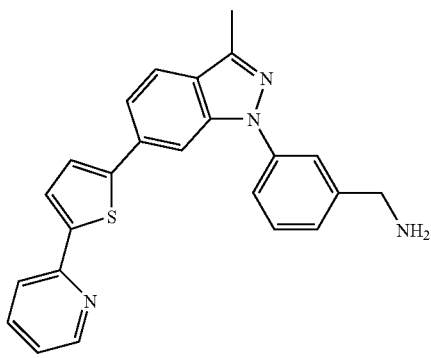

$^1$H-NMR (400 MHz, CDCl$_3$) δ 8.58 (dt, J=3.54, 1.22 Hz, 1H), 7.94 (s, 1H), 7.72 (d, J=8.38 Hz, 1H), 7.71 (dd, J=1.69, 8.00 Hz, 1H), 7.68-7.66 (m, 2H), 7.59 (m, J=7.98 Hz, 1H), 7.55 (d, J=3.80 Hz, 1H), 7.53 (dd, J=8.15, 1.37 Hz, 1H), 7.52 (t, J=7.73 Hz, 1H), 7.40 (d, J=3.86 Hz, 1H), 7.33 (d, J=7.44 Hz, 1H), 7.16 (ddd, J=2.12, 4.93, 6.76 Hz, 1H), 3.99 (s, 2H), 2.66 (s, 3H). Mass spectrum (LCMS, ESI pos.) calcd. for C$_{24}$H$_{20}$N$_4$S: 397.1 (M+H). Found: 397.1.

EXAMPLE 88

1-{4-[1-(3-Aminomethyl-phenyl)-3-methyl-1H-indazol-6-yl]-phenyl}-pyrrolidin-2-one

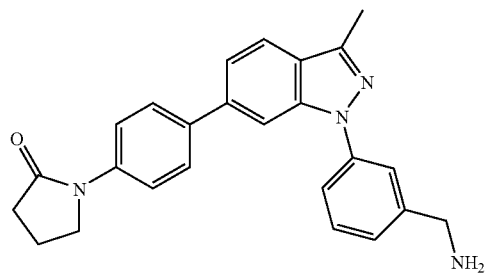

$^1$H-NMR (400 MHz, CDCl$_3$) δ 7.85 (s, 1H), 7.78 (d, J=8.34 Hz, 1H), 7.74 (d, J=8.85 Hz, 1H), 7.75-7.72 (m, 2H), 7.67 (m, J=8.80 Hz, 2H), 7.63 (m, J=8.32 Hz, 1H), 7.51 (t, J=7.78 Hz, 1H), 7.46 (dd, J=1.33, 8.35 Hz, 1H), 7.33 (d, J=7.57 Hz, 1H), 4.00 (s, 2H), 3.94 (t, J=7.03 Hz, 2H), 2.70 (s, 3H), 2.67 (t, J=8.11 Hz, 2H), 2.22 (quintet, J=7.59 Hz, 2H). Mass spectrum (LCMS, ESI pos.) calcd. for C$_{25}$H$_{24}$N$_4$O: 397.2 (M+H). Found: 397.1.

EXAMPLE 89

1-{4-[1-(3-Aminomethyl-phenyl)-3-methyl-1H-indazol-6-yl]-phenyl}-piperidin-2-one

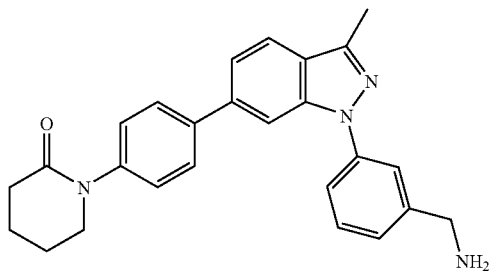

$^1$H-NMR (400 MHz, CDCl$_3$) δ 7.84, (s, 1H), 7.77 (d, J=8.33 Hz, 1H), 7.69 (s, 1H), 7.65 (d, J=8.39 Hz, 1H), 7.60 (m, J=8.31 Hz, 1H), 7.50 (t, J=7.76 Hz, 1H), 7.43 (dd, J=1.04, 8.32 Hz, 1H), 7.35 (m, J=8.39 Hz, 1H), 7.31 (d, J=7.58 Hz, 1H), 3.98 (s, 2H), 3.70 (t, J=5.30 Hz, 2H), 2.68 (s, 3H), 2.60 (t, J=6.13 Hz, 2H), 1.98 (m, 4H). Mass spectrum (LCMS, ESI pos.) calcd. for C$_{26}$H$_{26}$N$_4$O: 411.2 (M+H). Found: 411.2.

EXAMPLE 90

7-Fluoro-1-(4-methoxy-phenyl)-6-(2-oxo-2H-[1,3']bipyridinyl-6'-yl)-1H-indazole-3-cariboxylic acid amide mesylate

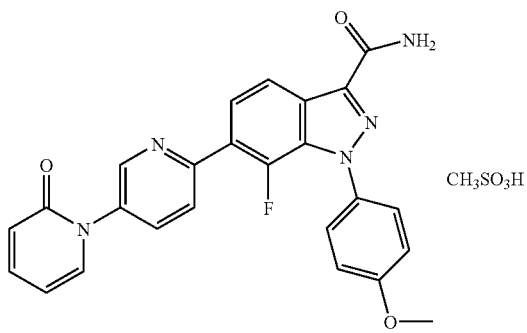

$^1$H-NMR (400 MHz, DMSO-d6) δ 8.84 (d, J=2.0 Hz, 1H), 8.32 (d, J=8.5 Hz, 1H) 8.03 (dd, J=1.4, 8.5 Hz, 2H), 7.67 (m, 1H), 7.57 (m, 6H), 7.07 (d, J=6.7 Hz, 2H), 6.72 (d, J=9.2 Hz, 1H), 6.46 (t, J=6.8 Hz, 1H), 3.92 (s, 3H), 2.85 (s, 3H). Mass Spectrum (LCMS, ESI, pos.) Calcd. for C$_{25}$H$_{18}$FN$_5$O$_3$: 456.1 (M+H); found: 456.2.

EXAMPLE 91

1-[4-(3'-Amino-7-fluoro-3-methyl-1'H-[1,5']biindazolyl-6-yl)-3-fluoro-phenyl]-piperidin-2-one

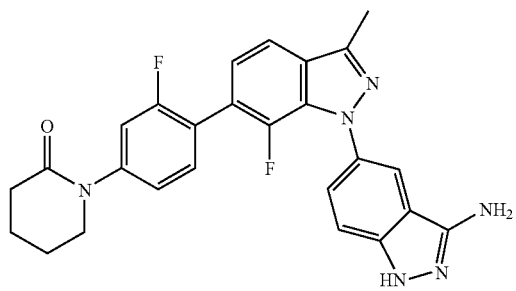

$^1$H-NMR (400 MHz, CDCl$_3$) δ 9.23 (s, 1H), 7.77 (t, J=2.2 Hz, 1H), 7.62 (m, 1H), 7.57 (d, J=8.8 Hz, 1H), 7.46 (t, J=8.3 Hz, 1H), 7.38 (d, J=8.8 Hz, 1H), 7.17 (m, 3H), 4.15 (br s, 2H), 3.70 (t, J=5.6 Hz, 2H), 2.73 (s, 3H), 2.62 (t, J=6.3 Hz, 2H), 1.99 (m, 4H).

Mass Spectrum (LCMS, ESI, pos.) Calcd. for C$_{26}$H$_{22}$FN$_6$O: 473.2 (M+H); Found: 473.3.

EXAMPLE 92

1-(4-[1-(1-Amino-isoquinolin-7-yl)-7-fluoro-3-methyl-1H-indazol-6-yl]-3-fluoro-phenyl}-piperidin-2-one

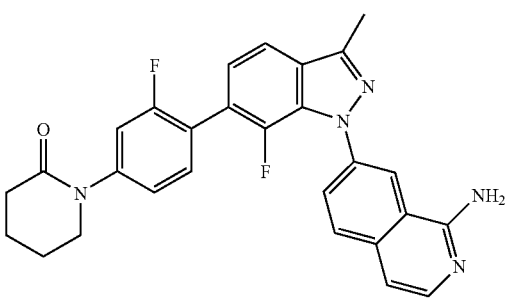

$^1$H-NMR (400 MHz, CDCl$_3$) δ 7.99 (m, 3H), 7.83 (d, J=8.7 Hz, 1H), 7.60 (d, J=8.2 Hz, 1H), 7.47 (t, J=8.3 Hz, 1H), 7.19 (m, 3H), 7.11 (d, J=5.8 Hz, 1H), 5.23 (s, 2H), 3.72 (t, J=5.5 Hz, 2H), 2.72 (s, 3H), 2.62 (t, J=6.3 Hz, 2H), 2.00 (m, 4H). Mass Spectrum (LCMS, ESI, pos.) Calcd. for C$_{28}$H$_{23}$F$_2$N$_5$O: 484.2 (M+H); Found: 484.3.

EXAMPLE 93

7-[7-Fluoro-6-(3-fluoro-2'-methanesulfonyl-biphenyl-4-yl)-3-methyl-indazol-1-yl]-isoquinolin-1-ylamine

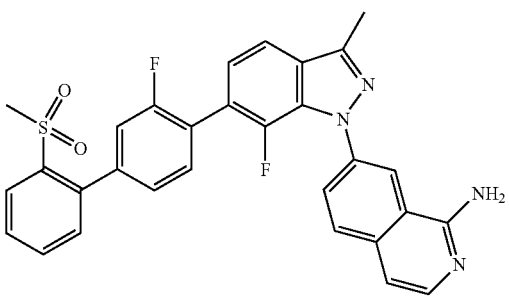

$^1$H-NMR (400 MHz, DMSO) δ 8.28 (dd, J=1.2, 8.0 Hz, 1H), 8.04 (m, 1H), 8.00 (d, J=5.9 Hz, 1H), 7.96 (m, 1H), 7.85, (d, J=8.7 Hz, 1H), 7.72 (dt, J=1.5, 7.5 Hz, 1H), 7.64 (m, 2H), 7.55 (t, J=7.6 Hz, 1H), 7.44 (d, J=1.2, 7.5 Hz, 1H), 7.40 (dd, J=1.7, 7.8 Hz, 1H), 7.33 (m, 2H), 7.13 (d, J=5.9 Hz, 1H), 5.2 (br s, 2H), 2.80 (s, 3H), 2.74 (s, 3H).

Mass Spectrum (LCMS, ESI, pos.) Calcd. for C$_{30}$H$_{22}$F$_2$N$_5$O$_2$S: 541.1 (M+H); Found: 541.2.

EXAMPLE 94

1-{4-[1-(1-Amino-isoquinolin-7-yl)-7-fluoro-3-trifluoromethyl-1H-indazol-6-yl]-3-fluoro-phenyl}-piperidin-2-one

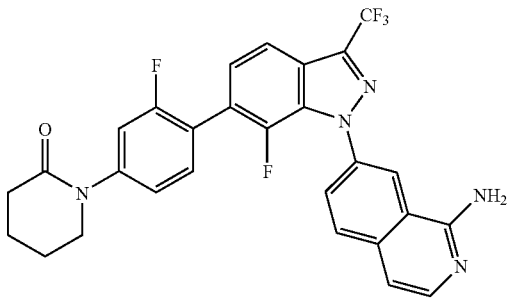

$^1$H-NMR (400 MHz, DMSO) δ 8.70 (s, 1H), 8.08 (d, J=8.8 Hz, 1H), 7.97 (m, 3H), 7.63 (m, 2H), 7.45 (d, J=11.8 Hz, 1H), 7.38 (d, J=8.3 Hz, 1H), 7.17 (s, 2H), 7.11 (d, J=5.8 Hz, 1H), 3.74 (t, J=5.5 Hz, 2H), 2.49 (t, J=6.33 Hz, 2H), 1.93 (m, 4H). Mass Spectrum (LCMS, ESI, pos.) Calcd. for $C_{28}H_{20}F_5N_5O$: 538.2 (M+H); Found: 538.2.

EXAMPLE 95

1-{4-[1-(3-Chloro-phenyl)-7-fluoro-3-trifluoromethyl-1H-indazol-6-yl]-3-fluoro-phenyl}-piperidin-2-one

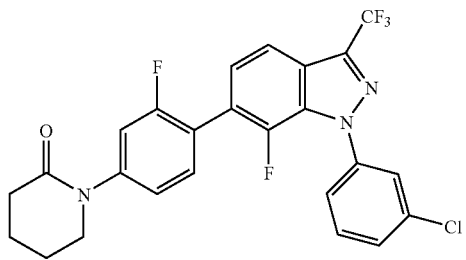

$^1$H-NMR (400 MHz, CDCl$_3$) δ 7.77 (d, J=8.4 Hz, 1H), 7.70 (m, 1H), 7.57 (m, 1H), 7.46 (m, 3H), 7.39 (dd, J=5.3, 8.1 Hz, 1H), 7.22 (m, 2H), 3.72 (t, J=5.8 Hz, 2H), 2.63 (t, J=6.6 Hz, 2H), 2.00 (m, 4H). Mass Spectrum (LCMS, ESI, pos.) Calcd. for $C_{25}H_{17}ClF_5N_3O$: 506.1 (M+H); Found: 506.2.

EXAMPLE 96

3-[7-Fluoro-3-methyl-6-(4-pyridin-4-ylphenyl)-indazol-1-yl]-benzylamine

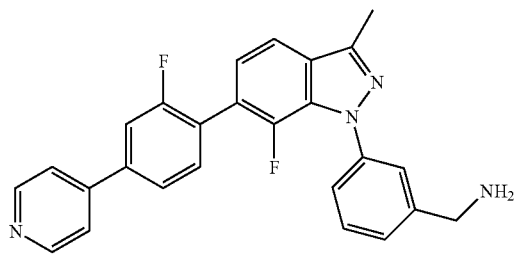

$^1$H NMR (400 MHz, CDCl$_3$): 8.69 (d, J=4.8 Hz, 2H), 7.75-7.73 (m, 4H), 7.61-7.53 (m, 4H), 7.50-7.42 (m, 2H), 7.34 (d, J=7.3 Hz, 1H), 7.29 (dd, J=7.3, 6.1 Hz, 1H), 3.96 (s, 2H), 2.68 (s, 3H). Mass Spectrum (LCMS, ESI, pos.) Calcd. for $C_{26}H_{22}FN_4$: 409.18 (M+H). Found: 409.1.

EXAMPLE 97

1-{4-[1-(3-Aminomethyl-phenyl)7-methoxy-3-methyl-1H-indazol-6-yl]-phenyl}-piperidin-2-one

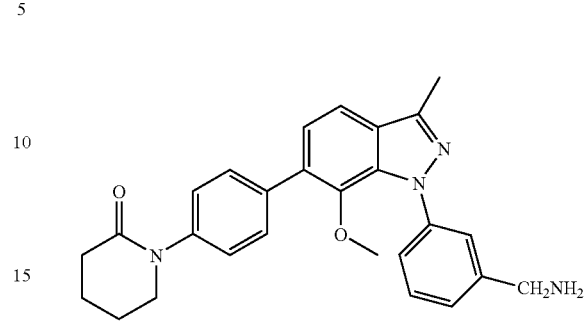

$^1$H-NMR (CDCl$_3$): δ 1.93-2.05 (m, 4H), 2.61 (t, 2H, J=6.04 Hz), 2.67 (s, 3H), 3.05 (s, 3H), 3.72 (t, 2H, J=5.65 Hz), 3.97 (bs, 2H), 7.22 (dd, 1H, J=8.26 Hz), 7.31-7.38 (m, 3H), 7.45 (t, 1H, J=7.82 Hz), 7.50-7.55 (m, 2H), 7.61-7.66 (m, 3H). Mass spectrum (LCMS, ESI pos.) calcd. for $C_{27}H_{28}N_4O_2$: 441.22 (M+H). Found: 441.1

EXAMPLE 98

1[1-(3-Aminomethyl-phenyl)-7-fluoro-3-methyl-1H-indazol-6-yl]-4-pyridin-2-yl-piperazin-2-one

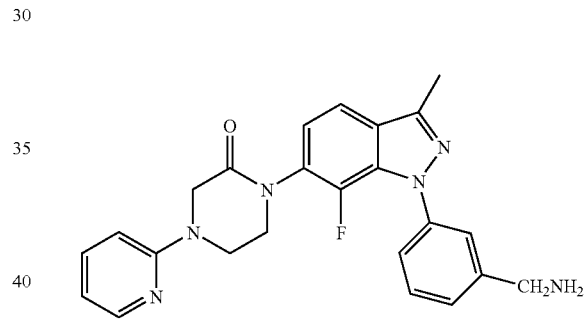

$^1$H-NMR (CDCl$_3$): δ 2.63 (s, 3H), 3.86 (t, 2H, J=4.84 Hz), 3.95 (s, 2H), 4.11 (t, 2H, J=4.62 Hz), 4.31 (s, 2H), 6.63 (d, 1H, J=8.59 Hz), 6.73 (dd, 1H, J=7.76 Hz, 5.58 Hz) 7.09 (dd, 1H, J=8.45 Hz, 5.80 Hz), 7.32-7.60 (m, 7H). Mass spectrum (LCMS, ESI pos.) calcd. for $C_{24}H_{23}FN_6O$: 431.19 (M+H). Found: 431.1

BIOLOGY ASSAY PROCEDURES

In vitro Inhibition of Purified Enzymes

Reagents: All buffer salts were obtained from Sigma Chemical Company (St. Louis, Mo.), and were of the highest purity available. The enzyme substrate, S-2765 (Z-D-Arg-Gly-Arg-p-nitroanilide) was obtained from DiaPharma (West Chester, Ohio). N-succinyl-Ala-Ala-Pro-Arg-p-nitroanilide (BACHEM L-1720) was obtained from BACHEM (King of Prussia, Pa.). N-p-Tosyl-Gly-Pro-Lys-p-nitroanilide (Sigma T6140), N-succinyl-Ala-Ala-Pro-Phe-p-nitroanilide (Sigma S7388), N-CBZ-Val-Gly-Arg-p-nitroanilide (Sigma C7271) was obtained from Sigma and N-succinyl-Ala-Ala-Pro-Val-p-nitroanilide (BACHEM L-1770) was obtained from BACHEM (King of Prussia, Pa.).

Human α-thrombin and human Factor Xa were obtained from Enzyme Research Laboratories (South Bend, Ind.).

Human trypsin was obtained from Calbiochem (La Jolla, Calif.). Human plasmin was obtained from Enzyme Research Laboratories (South Bend, Ind.). Bovine a-chymotrypsin (Sigma C4129) and human kidney cell urokinase (Sigma U5004) was obtained from Sigma. Human leukocyte elastase was obtained from Elastin Products (Pacific, Mo.).

Ki Determinations: All assays are based on the ability of the test compound to inhibit the enzyme-catalyzed hydrolysis of a peptide p-nitroanilide substrate. In a typical Ki determination, substrate is prepared in DMSO, and diluted into an assay buffer consisting of 50 mM HEPES, pH 7.5, 200 mM NaCl, 0.05% n-octyl b-d-glucopyranoside. The final concentrations for each of the substrates are listed below. In general, substrate concentrations are lower than the experimentally determined value for Km. Test compounds are prepared as 10 mM solutions in DMSO. Dilutions are prepared in DMSO yielding 7 final concentrations encompassing a 200-fold concentration range. Enzyme solutions are prepared at the concentrations listed below in assay buffer.

In a typical Ki determination, into each well of a 96 well plate is pipetted 280 mL of substrate solution, 10 mL of test compound solution, and the plate allowed to thermally equilibrate at 37° C. in a Molecular Devices plate reader for 15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined apparent Ki value (Ki app). The Ki is calculated from the Ki app using the Ki factor specific for the assay, where Ki=Ki app×Ki factor, or Ki=Ki app×(1/(1+[S]/Km)).

Thrombin: Thrombin activity was assessed as the ability to hydrolyze the substrate N-succinyl-Ala-Ala-Pro-Arg-p-nitroanilide (Km=320 mM, Ki factor=0.76). Substrate solutions were prepared at a concentration of 107 mM in assay buffer. Final DMSO concentration was 4.3%. Purified human a-thrombin was diluted into assay buffer to a concentration of 33 nM. Final reagent concentrations were: [thrombin]=1.1 nM, [substrate N-succinyl-Ala-Ala-Pro-Arg-p-nitroanilide] =100 mM.

Factor X [Factor Xa]: Factor Xa activity was assessed as the ability to hydrolyze the substrate S-2765 (Z-D-Arg-Gly-Arg-p-nitroanilide, Km=260 mM, Ki factor=0.72). Substrate solutions were prepared at a concentration of 107 mM in assay buffer. Final DMSO concentration was 3.3%. Purified activated human Factor X was diluted into assay buffer to a concentration of 16 nM. Final reagent concentrations were: [Factor Xa]=0.53 nM, [S-2765]=100 mM.

Trypsin: Trypsin activity was assessed as the ability to hydrolyze the substrate S-2765 (Z-D-Arg-Gly-Arg-p-nitroanilide, Km=61 mM, Ki factor=0.50). Substrate solutions were prepared at a concentration of 64 mM in assay buffer. Final DMSO concentration was 3.3%. Purified human trypsin was diluted into assay buffer to a concentration of 10 nM. Final reagent concentrations were: [Trypsin]=0.33 nM, [S-2765]=60 mM.

Plasmin: Plasmin activity is assessed as the ability to hydrolyze the N-p-Tosyl-Gly-Pro-Lys-p-nitroanilide. Substrate solutions are prepared at a concentration of 37 mM (37 mM<<Km=243 mM) in assay buffer. Final DMSO concentration is 4.3%. Purified human plasmin is diluted into assay buffer to a concentration of 240 nM. Final reagent concentrations are: [Plasmin]=8 nM, [N-p-Tosyl-Gly-Pro-Lys-p-nitroanilide]=37 mM.

Chymotrypsin: Chymotrypsin activity is assessed as the ability to hydrolyze N-succinyl-Ala-Ala-Pro-Phe-p-nitroanilide. Substrate solutions are prepared at a concentration of 14 mM (14 mM<<Km=62 mM) in assay buffer. Final DMSO concentration is 4.3%. Purified bovine chymotrypsin is diluted into assay buffer to a concentration of 81 nM. Final reagent concentrations are: [Chymotrypsin]=2.7 nM, [N-succinyl-Ala-Ala-Pro-Phe-p-nitroanilide]=14 mM.

TABLE 1

$K_I$ RESULTS

| Example # | FXa (μM) | Thrombin (μM) | Trypsin (μM) |
|---|---|---|---|
| 4 | 0.66 | — | — |
| 6 | 0.12 | >15.2 | >10 |
| 7 | 0.22 | >15.2 | 0.7 |
| 12 | 2.6 | >15.2 | 6.9 |
| 15 | 2.82 | >15.2 | 1.59 |
| 25 | 0.04 | >15.2 | >10 |
| 35 | 0.033 | >15.2 | 2.9 |
| 43 | 0.006 | >15.2 | >10 |
| 59 | 0.005 | >15.2 | >10 |
| 66 | 0.002 | >15.2 | >10 |
| 75 | 0.001 | 1.6 | 0.14 |
| 82 | 0.045 | >15.2 | 1.5 |
| 86 | 0.048 | >15.2 | >10 |
| 93 | 0.046 | >15.2 | >10 |
| 95 | 0.34 | >15.2 | >10 |

While the foregoing specification teaches the principles of the present invention, with examples provided for the purpose of illustration, it will be understood that the practice of the invention encompasses all of the usual variations, adaptations and modfications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound having Formula I,

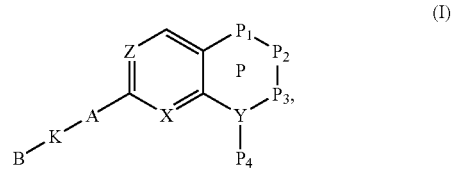

wherein

X is CF;

Z is CH;

A and B are independently selected from ethenyl, ethynyl, aryl, heteroaryl, 3-8 numbered carbocycle or 5-8 numbered heterocycle, each of which can be optionally substituted with 1, 2, 3 or 4 R groups;

K is selected from a bond, ethenyl, ethynyl, NR', O, S, $SO_2$ or CO;

Ring P is pyrazole follows:

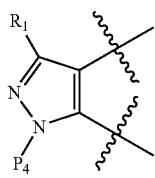

P₄ is substituted or unsubstituted benzene selected from:

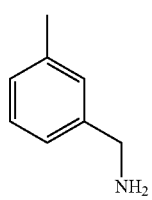 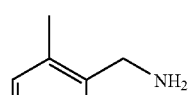 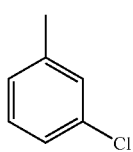

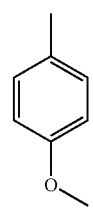 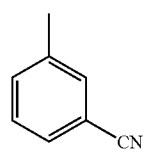 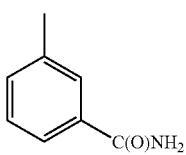

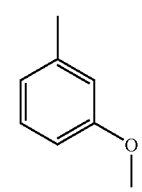 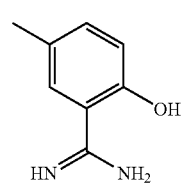

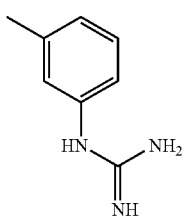 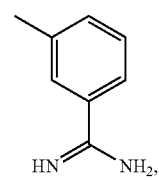

wherein P₄ is optionally substituted with 1, 2, 3 or 4 R groups;

$R_1$ is selected from hydrogen, halogen, alkyl, haloalkyl, haloalkoxy, alkenyl, alkynyl, cycloalkyl, NCH₂R, OCH₂R, SCH₂R, S(O)$_p$CH₂R, C(O)NR, OC(O)NR, NR$^a$C(O)NR$^a$CH₂R, NR$^a$C(O)OCH₂R, NR$^a$C(O)CH₂R, hydroxyalkyl, cyano, nitro, trifluoromethyl or -CO₂R;

provided that $R_1$ forms other than an N-halo, N-N, N-S, N-O, or N-CN bond;

R is selected from hydrogen, halogen, alkyl, alkenyl, alkynyl, cycloalkyl, hydroxy, alkoxy, haloalkyl, haloalkoxy, hydroxyalkyl, cyano, nitro, trifluoromethyl, —CO₂R$^x$, —CH₂OR$^x$ or —OR$^x$, $R^x$ is selected from hydrogen, $C_{1-6}$ alkyl; optionally substituted alkyl, optionally substituted cycloalkyl, optionally substituted aryl or optionally substituted heteroaryl, wherein optionally substituted alkyl, cycloalkyl, aryl and heteroaryl are each optionally substituted with one, two, three or four substituents selected from halogen, hydroxy, amino, mono or dialkyl amino, cyano, nitro, ester, acid or ether;

R' is selected from hydrogen, optionally substituted alkyl, optionally substituted alkenyl, optionally substituted alkynyl, optionally substituted cycloalkyl, optionally substituted $C_{6-10}$aryl, optionally substituted $C_{6-10}$ arylalkyl, optionally substituted heteroaryl or optionally substituted heteroaryl-alkyl, wherein optionally substituted alkyl, alkenyl, alkynyl, cycloalkyl, $C_{6-10}$aryl, the $C_{6-10}$aryl portion of $C_{6-10}$ arylalky, heteroaryl and the heteroaryl portion of heteroaryl-alkyl are each optionally substituted with one, two, three or four substituents selected from halogen. hydroxy, carboxy, amino, monoalkylamino, dialkylamino, cyano, nitro, ester, acid or ether; and $R^2$ is selected from hydrogen, $C_{1-4}$alkyl or $C_{6-10}$aryl; or a pharmaceutically acceptable salt or stereoisomer thereof.

2. The compound of claim wherein Ring P is:

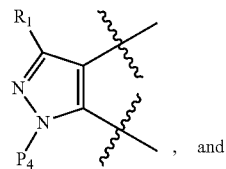 , and $R_1$ is selected from alkyl, haloalkyl, C(O)NR or hydroxyalkyl.

3. The compound of claim 1, wherein Ring P is:

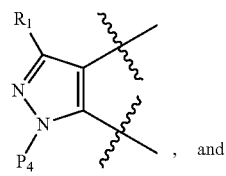 , and

P₄ is selected from:

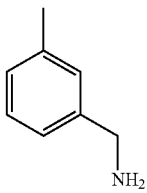 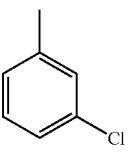 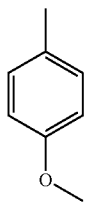

-continued

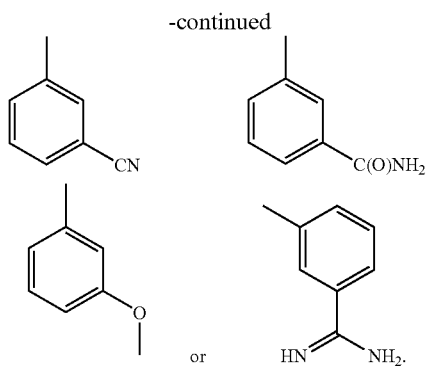

4. The compound of claim 1, wherein A is selected from aryl, heteroaryl, 3-8 numbered carbocycle or 5-8 numbered heterocycle.

5. The compound of claim 4, wherein A is selected from:

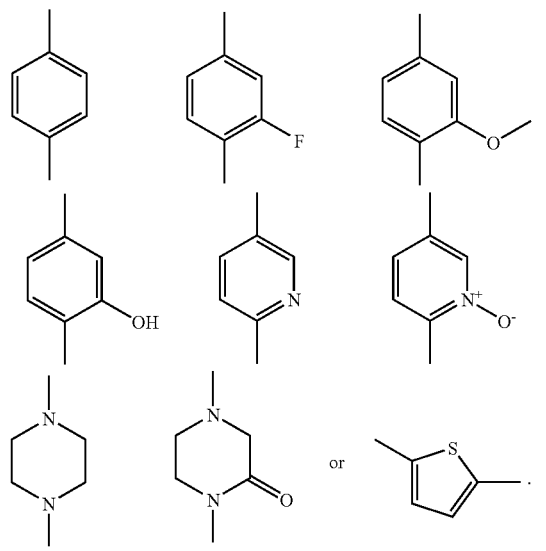

6. The compound of claim 1, wherein K is selected from a bond, ethynyl or NR'.

7. The compound of claim 1, wherein B is selected from aryl, heteroaryl, 3-8 numbered carbocycle or 5-8 numbered heterocycle.

8. The compound of claim 7, wherein B is selected from:

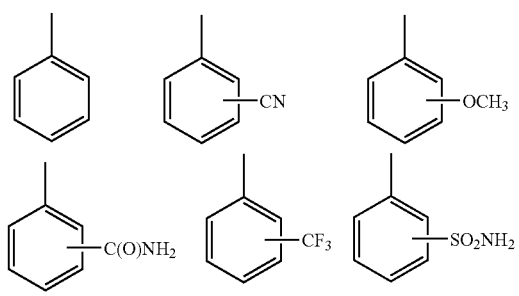

-continued

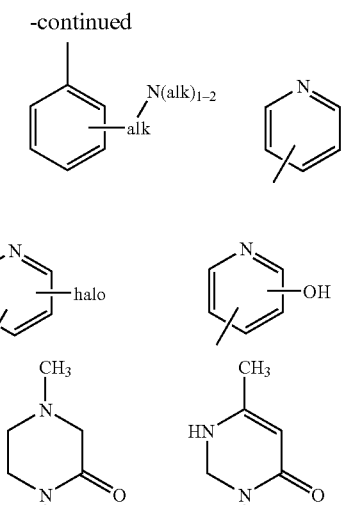

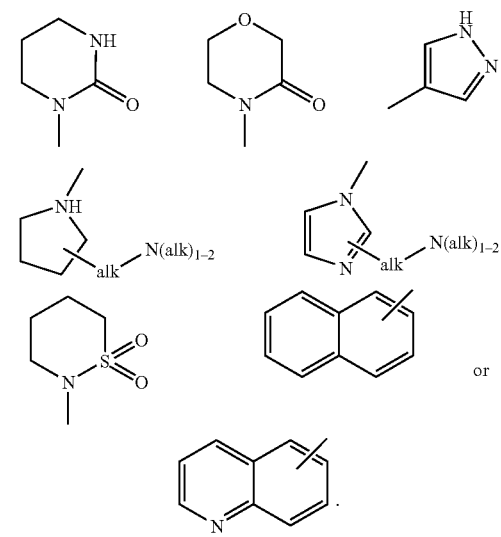

9. The compound of claim 1, wherein the compound is an isolated form thereof.

10. The compound of any-of-claim 1, wherein the form of said compound is a pharmaceutical composition or medicament comprising an effective amount of one or more of said compound.

11. The pharmaceutical composition of claim 10, wherein the composition further comprises an effective amount of the compound and a pharmaceutically acceptable carrier.

12. A process for preparing a pharmaceutical composition comprising the step of admixing a compound of claim 1 and a pharmaceutically acceptable carrier.

13. The pharmaceutical composition of claim 10, wherein the effective amount of the compound is in a range of from about 0.001 mg/kg to about 300 mg/kg of body weight per day.

* * * * *